(12) United States Patent
Klingler et al.

(10) Patent No.: US 7,166,609 B2
(45) Date of Patent: *Jan. 23, 2007

(54) PYRIMIDINE-4,6-DICARBOXYLIC ACID DIAMIDES FOR SELECTIVELY INHIBITING COLLAGENASES

(75) Inventors: Otmar Klingler, Rodgau (DE); Reinhard Kirsch, Braunschweig (DE); Joerg Habermann, Rome (IT); Klaus-Ulrich Weithmann, Hofheim (DE); Christian Engel, Frankfurt (DE); Bernard Pirard, Darmstadt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 324 days.

This patent is subject to a terminal disclaimer.

(21) Appl. No.: 10/700,273

(22) Filed: Nov. 3, 2003

(65) Prior Publication Data

US 2004/0167120 A1    Aug. 26, 2004

Related U.S. Application Data

(60) Provisional application No. 60/456,395, filed on Mar. 21, 2003, provisional application No. 60/458,316, filed on Mar. 28, 2003.

(30) Foreign Application Priority Data

Nov. 2, 2002  (DE) ................ 102 51 019
Nov. 20, 2002 (DE) ................ 102 54 092

(51) Int. Cl.
  C07D 239/54  (2006.01)
  C07D 403/12  (2006.01)
  C07D 403/14  (2006.01)
  C07D 413/12  (2006.01)
  C07D 417/12  (2006.01)
  A61K 31/506  (2006.01)
  A61P 19/02   (2006.01)

(52) U.S. Cl. ............ 514/256; 544/333; 544/335; 544/53; 544/56; 544/63; 544/88; 544/98; 544/106; 540/606; 514/217.06; 514/226.8; 514/227.5; 514/228.8; 514/231.5; 514/241

(58) Field of Classification Search ........ 544/333, 544/335; 514/256
See application file for complete search history.

(56) References Cited

U.S. PATENT DOCUMENTS 5,130,317 A   7/1992   Baader et al.
5,260,323 A   11/1993  Baader et al.

FOREIGN PATENT DOCUMENTS

EP   0606046        10/1997
WO   WO 94/28889    12/1994
WO   WO 02/064080   8/2002
WO   WO 02/064571   8/2002

OTHER PUBLICATIONS

Hoekstra et al. The Oncologist, 6:415-427, 2001.*
Poole et al. Biochem. Soc. Symp. 70:115-123, 2003.*
Massova, et al., Matrix Metalloproteinases: Structures, Evolution, and Diversification, The FASEB Journal, (1998), 12, 1075-1095.
Weithmann, et al., Effects of Tiaprofenic Acid On Urinary Pyridinium Crosslinks in Adjuvant Arthritic Rats: Compassion With Doxycycline, Inflamm Res., 46 (1997), S. 246-252.
Organikum, Organisch Chemisches Grundpratikum, 15. Aufl.., VEB Deutscher Verlag der Wissenschaften, 1976; Methodenregister, S. 822.

* cited by examiner

*Primary Examiner*—Venkataraman Balasubramanian
(74) *Attorney, Agent, or Firm*—Ronald G. Ort

(57) ABSTRACT

Pyrimidine-4,6-dicarboxylic acid diamides of the formula I

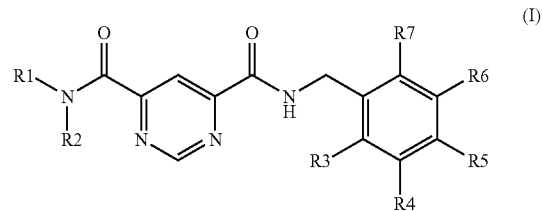

are suitable for selectively inhibiting collagenase (MMP 13). The pyrimidine-4,6-dicarboxylic acid diamides can therefore be used for treating degenerative joint diseases.

7 Claims, No Drawings

PYRIMIDINE-4,6-DICARBOXYLIC ACID DIAMIDES FOR SELECTIVELY INHIBITING COLLAGENASES

FIELD OF THE INVENTION

The invention relates to novel pyrimidine-4,6-dicarboxylic acid diamides and to their use for selectively inhibiting collagenase (MMP 13). The pyrimidine-4,6-dicarboxylic acid diamides can therefore be used for treating degenerative joint diseases.

BACKGROUND OF THE INVENTION

It is known that pyrimidine-4,6-dicarboxylic acid diamides and 2,4-substituted pyridine N-oxides inhibit the enzymes proline hydroxylase and lysine hydroxylase and thereby bring about an inhibition of collagen biosynthesis by exerting an influence on the collagen-specific hydroxylation reaction (EP 0418797; EP 0463592). This inhibition of collagen biosynthesis results in the formation of a nonfunctional, under-hydroxylated collagen molecule which the cells can only release into the extracellular space in small quantity. In addition, the under-hydroxylated collagen cannot be incorporated into the collagen matrix and is very readily degraded proteolytically. As a consequence of these effects, the overall quantity of collagen which is deposited extracellularly decreases. It is known from patent applications WO 02/064571 and WO 02/064080, that certain pyridine-2,4-dicarboxylic acid diamides and pyrimidine-4,6-dicarboxylic acid diamides can be allosteric inhibitors of MMP 13.

In diseases such as osteoarthritis and rheumatism, destruction of the joint takes place, with this destruction being caused, in particular, by the proteolytic breakdown of collagen due to collagenases. Collagenases belong to the metalloproteinase (MP) or matrix metalloproteinase (MMP) superfamily. Under physiological conditions, MMPs cleave collagen, laminin, proteoglycans, elastin or gelatin and therefore play an important role in bone and connective tissue. A large number of different inhibitors of the MMPs and/or collagenases have been disclosed (EP 0 606 046; WO 94/28889). Known MMP inhibitors frequently suffer from the disadvantage of lacking the specificity involved in inhibiting only one class of MMPs. As a result, most MMP inhibitors inhibit several MMPs simultaneously because the structure of the catalytic domain in the MMPs is similar. As a consequence, the inhibitors have the undesirable property of acting on many enzymes, including those which have a vital function (Massova I., et al., The FASEB Journal (1998) 12, 1075–1095).

Michael Murray showed that compounds which contain an unsubstituted benzo[1,3]dioxole ring as a radical inhibit the cytochrome P450 liver enzymes (Michael Murray, Current Drug Metabolism 2000, 67–84). Said radical is held to be responsible for these significant toxicological effects.

In an endeavor to find effective compounds for treating connective tissue diseases, it has now been found that the compounds which are employed in accordance with the invention are powerful inhibitors of matrix metalloproteinase 13 while essentially having no effect on MMPs 3 and 8.

SUMMARY OF THE INVENTION

The invention therefore relates to a compound of the formula I

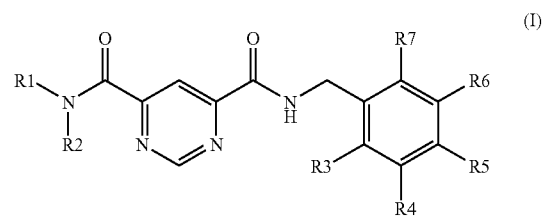

and/or all the stereoisomeric forms of the compound of the formula I and/or mixtures of these forms in any ratio, and/or a physiologically tolerated salt of the compound of the formula I, where for the case a)

R1 is hydrogen atom or —$(C_1-C_6)$-alkyl,

R2 is —$(C_1-C_6)$-alkyl, where alkyl is substituted, once, twice or three times, by 1. —$(C_1-C_6)$-alkyl-O—$(C_6-C_{14})$-aryl,
2. —$(C_0-C_6)$-alkyl-N(R8)-C(O)—O—$(C_1-C_6)$-alkyl, in which R8 is
   i) hydrogen atom or
   ii) —$(C_1-C_6)$-alkyl,
3. —C(O)—N(R9)-(R10), in which R9 and R10 are identical or different and are, independently of each other,
   i) hydrogen atom or
   ii) —$(C_1-C_6)$-alkyl, or
   R9 and R10 form, together with the nitrogen atom to which they are bonded, a 5-, 6- or 7-membered saturated ring, where a heteroatom from the series oxygen, sulfur and nitrogen can also replace one or two further carbon atoms and, in the case of nitrogen, the nitrogen atoms can, independently of each other, be unsubstituted or substituted by $(C_1-C_6)$-alkyl,
4. —$(C_6-C_{14})$-aryl, in which aryl is substituted, once, twice or three times, independently of each other, by
   4.1) —$CH_2$—C(O)—O—R8, in which R8 has the abovementioned meaning,
   4.2) —$(C_0-C_6)$-alkyl-C(O)—N(R9)-(R10), in which R9 and R10 have the abovementioned meaning,
   4.3) —$(C_0-C_6)$-alkyl-C(O)—NH—CN,
   4.4) —O—$(C_0-C_6)$-alkyl-C(O)—N(R9)-(R10), in which R9 and R10 have the abovementioned meaning,
   4.5) —$S(O)_y$—$(C_1-C_6)$-alkyl-C(O)—O—R8, in which R8 has the abovementioned meaning and y is 1 or 2,
   4.6) —$S(O)_z$—$(C_1-C_6)$-alkyl-C(O)—N(R9)-(R10), in which R9 and R10 have the abovementioned meaning and z is 0, 1 or 2,
   4.7) —$(C_0-C_6)$-alkyl-C(O)—N(R8)-$(C_0-C_6)$-alkyl-N(R9)-(R10), in which R8, R9 and R10 have the abovementioned meaning, 4.8) —C(O)—N(R8)-($C_0$–$C_6$)-alkyl-Het, where R8 has the abovementioned meaning and Het is a saturated or unsaturated monocyclic or bicyclic, 3- to 10-membered heterocyclic ring system which contains 1, 2 or 3 identical or different ring heteroatoms from the series nitrogen, oxygen and sulfur and is unsubstituted or substituted, once, twice or three times, independently of each other, by
  a) halogen,
  b) cyano,
  c) nitro
  d) hydroxyl,
  e) amino,
  f) —C(O)—O—($C_1$–$C_6$)-alkyl,
  g) —C(O)—OH,
  h) —($C_1$–$C_6$)-alkyl, where alkyl is unsubstituted or substituted, once, twice or three times, by halogen,
  i) —O—($C_1$–$C_6$)-alkyl, where alkyl is unsubstituted or substituted, once, twice or three times, by halogen,
4.9) —C(O)—N(R8)-($C_0$–$C_6$)-alkyl-($C_6$–$C_{14}$)-aryl, where aryl is unsubstituted or substituted, once, twice or three times, independently of each other, by the abovementioned radicals a) to i),
4.10) —$CH_2$—N(R9)-(R10), in which R9 and R10 have the abovementioned meaning,
4.11) —$(CH_2)_y$—N(R8)-C(O)—($C_1$–$C_6$)-alkyl in which alkyl is unsubstituted or substituted, once, twice or three times, independently of each other, by the abovementioned radicals a) to i) and y is 1 or 2,
4.12) —$(CH_2)_x$—N(R8)-C(O)—($C_0$–$C_6$)-alkyl-($C_6$–$C_{14}$)-aryl in which aryl is unsubstituted or substituted, once, twice or three times, independently of each other, by the abovementioned radicals a) to i) and x is 0, 1, 2, 3 or 4,
4.13) —$(CH_2)_x$—N(R8)-C(O)—($C_0$–$C_6$)-alkyl-Het in which Het is unsubstituted or substituted, once, twice or three times, independently of each other, by the abovementioned radicals a) to i), and x is 0, 1, 2, 3 or 4,
4.14) —$(CH_2)_x$—N(R8)-C(O)—O—($C_1$–$C_6$)-alkyl in which alkyl is unsubstituted or substituted, once, twice or three times, independently of each other, by the abovementioned radicals a) to i) and x is 0, 1, 2, 3 or 4,
4.15) —$(CH_2)_x$—N(R8)-C(O)—O—($C_0$–$C_6$)-alkyl-($C_6$–$C_{14}$)-aryl in which aryl is unsubstituted or substituted, once, twice or three times, independently of each other, by the abovementioned radicals a) to i), and x is 0, 1, 2, 3 or 4,
4.16) —$(CH_2)_x$—N(R8)-C(O)—O—($C_0$–$C_6$)-alkyl-Het in which Het is unsubstituted or substituted, once, twice or three times, independently of each other, by the abovementioned radicals a) to i), and x is 0, 1, 2, 3 or 4,
4.17) —$(CH_2)_x$—N(R8)-C(O)—N(R11)-R12 in which R8 and x have the abovementioned meaning and R11 and R12 are identical or different and are, independently of each other,
  4.17.1) hydrogen atom,
  4.17.2) —($C_1$–$C_6$)-alkyl,
  4.17.3) —($C_0$–$C_6$)-alkyl-($C_6$–$C_{14}$)-aryl in which aryl is unsubstituted or substituted, once, twice or three times, independently of each other, by the abovementioned radicals a) to i),
  4.17.4) —($C_0$–$C_6$)-alkyl-Het in which Het is unsubstituted or substituted, once, twice or three times, independently of each other, by the abovementioned radicals a) to i),
  4.17.5) —C(O)—($C_1$–$C_6$)-alkyl,
  4.17.6) —C(O)—($C_0$–$C_6$)-alkyl-($C_6$–$C_{14}$)-aryl,
  4.17.7) —C(O)—($C_0$–$C_6$)-alkyl-Het,
  4.17.8) —$SO_2$—($C_1$–$C_6$)-alkyl,
  4.17.9) —$SO_2$—($C_0$–$C_6$)-alkyl-($C_6$–$C_{14}$)-aryl,
  4.17.10) —$SO_2$—($C_0$–$C_6$)-alkyl-Het
4.18) —$(CH_2)_x$—N(R8)-S(O)$_2$—($C_0$–$C_6$)-alkyl-($C_6$–$C_{14}$)-aryl in which aryl is unsubstituted or substituted, once, twice or three times, independently of each other, by the abovementioned radicals a) to i) and x and R8 have the abovementioned meaning,
4.19) —$(CH_2)_x$—N(R8)-S(O)$_2$—($C_0$–$C_6$)-alkyl-Het, in which Het is unsubstituted or substituted, once, twice or three times, independently of each other, by the abovementioned radicals a) to i), and x and R8 have the abovementioned meaning,
4.20) —$(CH_2)_x$—N(R8)-S(O)$_2$—N(R8)-($C_1$–$C_6$)-alkyl in which alkyl is unsubstituted or substituted, once, twice or three times, independently of each other, by the abovementioned radicals a) to i) and x and R8 have the abovementioned meaning, independently of each other,
4.21) —$(CH_2)_x$—N(R8)-S(O)$_2$—N(R8)-($C_0$–$C_6$)-alkyl-($C_6$–$C_{14}$)-aryl in which aryl is unsubstituted or substituted, once, twice or three times, independently of each other, by the abovementioned radicals a) to i) and x and R8 have the abovementioned meaning, independently of each other,
4.22) —$(CH_2)_x$—N(R8)-S(O)$_2$—N(R8)-($C_0$–$C_6$)-alkyl-Het in which Het is unsubstituted or substituted, once, twice or three times, independently of each other, by the abovementioned radicals a) to i) and x and R8, independently of each other, have the abovementioned meaning,
4.23) —$(CH_2)_x$—N(R8)-C(O)—N(R8)-$SO_2$—R13, where x and R8, independently of each other, have the abovementioned meaning and R13 is —($C_1$–$C_6$)-alkyl or —($C_0$–$C_6$)-alkyl-($C_6$–$C_{14}$)-aryl,
4.24) —S(O)$_2$—N(R8)-($C_0$–$C_6$)-alkyl-($C_6$–$C_{14}$)-aryl in which aryl is unsubstituted or substituted, once, twice or three times, independently of each other, by the abovementioned radicals a) to i) and R8 has the abovementioned meaning,
4.25) S(O)$_2$—N(R8)-($C_0$–$C_6$)-alkyl-Het in which Het is unsubstituted or substituted, once, twice or three times, independently of each other, by the abovementioned radicals a) to i) and R8 has the abovementioned meaning,
4.26) —S(O)$_2$—N(R8)-($C_1$–$C_6$)-alkyl in which alkyl is unsubstituted or substituted, once, twice or three times, independently of each other, by the abovementioned radicals a) to i) and R8 has the abovementioned meaning,
4.27) —S(O)$_2$—($C_0$–$C_6$)-alkyl-($C_6$–$C_{14}$)-aryl in which aryl is unsubstituted or substituted, once, twice or three times, independently of each other, by the abovementioned radicals a) to i), 4.28) —S(O)$_2$—(C$_0$–C$_6$)-alkyl-Het in which Het is unsubstituted or substituted, once, twice or three times, independently of each other, by the abovementioned radicals a) to i), 4.29) —O-Het in which Het is unsubstituted or substituted, once, twice or three times, independently of each other, by the abovementioned radicals a) to i), or 4.30) -Het in which Het is unsubstituted or substituted, once, twice or three times, independently of each other, by the abovementioned radicals a) to i), or 4.31) -phenyl where the phenyl ring is unsubstituted or substituted, once, twice or three times, by
    4.31.1) halogen,
    4.31.2) —(C$_1$–C$_6$)-alkyl,
    4.31.3) —O—(C$_1$–C$_6$)-alkyl,
    4.31.4) —S(O)$_2$—R16 where R16 is (C$_1$–C$_6$)-alkyl or —NH$_2$, 5. —C(O)—N(R8)-(C$_0$–C$_6$)-alkyl-(C$_6$–C$_{14}$)-aryl in which aryl is unsubstituted or substituted, once, twice or three times, independently of each other, by the abovementioned radicals 4.1) to 4.31) or 4.8) a) to 4.8) i) and R8 has the abovementioned meaning, or 6. —C(O)—N(R8)-(C$_0$–C$_6$)-alkyl-Het in which Het has the abovementioned meaning and is unsubstituted or substituted, once, twice or three times, independently of each other, by the abovementioned radicals 4.1) to 4.31) or 4.8) a) to 4.8) i) and R8 has the abovementioned meaning, or 7. —NH—(C$_6$–C$_{14}$)-aryl in which aryl is unsubstituted or substituted, once, twice or three times, independently of each other, by the abovementioned radicals 4.1) to 4.30) or 4.8) a) to 4.8) i), or 8. —NH-Het in which Het has the abovementioned meaning and is unsubstituted or substituted, once, twice or three times, independently of each other, by the abovementioned radicals 4.1) to 4.31) or 4.8) a) to 4.8) i), R3, R4, R5, R6 and R7 are identical or different and are, independently of each other,
1. hydrogen atom,
2. halogen,
3. —(C$_1$–C$_6$)-alkyl in which alkyl is unsubstituted or substituted, once, twice or three times, by halogen,
4. —O—(C$_1$–C$_6$)-alkyl in which alkyl is unsubstituted or substituted, once, twice or three times, by halogen, or
5. —S—(C$_1$–C$_6$)-alkyl, or R4 and R5 or R5 and R6 form, together with the carbon atoms to which they are in each case bonded, independently of each other, a 5- or 6-membered ring which is aromatic or saturated and contains zero, one or two heteroatoms from the series oxygen, nitrogen or sulfur, where the ring is unsubstituted or is substituted, at one or at several carbon atoms, once or twice, by halogen and the other radicals R3, R6 and R7 or R3, R4 and R7 have the abovementioned meaning of 1. to 5.

or for the case b)

R1 is hydrogen atom or —(C$_1$–C$_6$)-alkyl,

R2 is —(C$_1$–C$_6$)-alkyl, where alkyl is substituted, once, twice or three times, by
1. —C(O)—O—R8', in which R8' is
    1.1) hydrogen atom or
    1.2) —(C$_1$–C$_6$)-alkyl,
2. —(C$_1$–C$_6$)-alkyl-O—R8', in which R8' has the abovementioned meaning, 3. —(C$_6$–C$_{14}$)-aryl in which aryl is substituted, once, twice or three times, independently of each other, by 3.1) —(C$_2$–C$_6$)-alkyl-C(O)—O—R8' in which R8' has the abovementioned meaning, 3.2) —O—(C$_1$–C$_6$)-alkyl-C(O)—O—R8' in which R8' has the abovementioned meaning, 3.3) —N(R14)-(R15) in which R14 and R15 form, together with the nitrogen atom to which they are bonded, a 5-, 6- or 7-membered saturated ring, where a heteroatom from the series oxygen, sulfur and nitrogen can also replace one or two further carbon atoms and, in the case of nitrogen, the nitrogen atoms can, independently of each other, be unsubstituted or substituted by (C$_1$–C$_6$)-alkyl, 3.4) —(CH$_2$)$_k$—N(R9')-(R10') in which k is 2, 3, 4 or 5 and R9' and R10' are identical or different and are, independently of each other,
    3.4.1) hydrogen or
    3.4.2) —(C$_1$–C$_6$)-alkyl, or
R9' and R10' form, together with the nitrogen atom to which they are bonded, a 5-, 6- or 7-membered saturated ring, where a heteroatom from the series oxygen, sulfur and nitrogen can also replace one or two further carbon atoms and, in the case of nitrogen, the nitrogen atoms can, independently of each other, be unsubstituted or substituted by (C$_1$–C$_6$)-alkyl, 3.5) —O—(C$_2$–C$_6$)-alkyl-N(R9')-R10', where R9' and R10' have the abovementioned meaning, 3.6) —N(R8')-C(O)—(C$_1$–C$_6$)-alkyl in which alkyl is unsubstituted or substituted, once, twice or three times, by
    3.6.1) halogen,
    3.6.2) cyano,
    3.6.3) nitro
    3.6.4) hydroxyl,
    3.6.5) amino,
    3.6.6) —C(O)—O—(C$_1$–C$_6$)-alkyl, or
    3.6.7) —C(O)—OH, and R8' has the abovementioned meaning, 3.7) -phenyl, where the phenyl ring is unsubstituted or substituted, once, twice or three times, by
    3.7.1) halogen,
    3.7.2) —(C$_1$–C$_6$)-alkyl,
    3.7.3) —O—(C$_1$–C$_6$)-alkyl,
    3.7.4) —S(O)$_2$—R16', where R16' is (C$_1$–C$_6$)-alkyl or —NH$_2$, 4. Het, where Het is a saturated or unsaturated monocyclic or bicyclic, 3- to 10-membered heterocyclic ring system which contains 1, 2 or 3 identical or different ring heteroatoms from the series nitrogen, oxygen and sulfur and is unsubstituted or substituted, once, twice or three times, by
    4.1) halogen,
    4.2) cyano,
    4.3) nitro,
    4.4) hydroxyl,
    4.5) amino,
    4.6) —C(O)—O(C$_1$–C$_6$)-alkyl,
    4.7) —C(O)—OH,
    4.8) —(C$_1$–C$_6$)-alkyl, where alkyl is unsubstituted or substituted, once, twice or three times, by halogen,
    4.9) —O—(C$_1$–C$_6$)-alkyl, where alkyl is unsubstituted or substituted, once, twice or three times, by halogen,
    4.10) pyridyl, or 4.11) phenyl, where phenyl is unsubstituted or substituted, once or more than once and independently of each other, by a radical from the series halogen, —$(C_1$–$C_6)$-alkoxy and —$(C_1$–$C_6)$-alkyl, and R4 and R5 or R5 and R6 form, together with the carbon atoms to which they are in each case bonded, independently of each other, a 5- or 6-membered ring which is saturated and contains one or two heteroatoms from the series oxygen, nitrogen or sulfur, where the ring is unsubstituted or substituted, at one or at several carbon atoms, once or twice, by halogen, and the other radicals R3, R6 and R7 or R3, R4 and R7 are hydrogen, with the proviso that the unsubstituted benzo[1,3]dioxole ring is excluded.

The invention also relates to a compound of the formula I where, for the case a)

R1 is hydrogen atom or —$(C_1$–$C_6)$-alkyl,

R2 is —$(C_1$–$C_6)$-alkyl, where alkyl is substituted, once, twice or three times, by
1. —$(C_1$–$C_6)$-alkyl-O—$(C_6$–$C_{14})$-aryl,
2. —$(C_0$–$C_6)$-alkyl-N(R8)-C(O)—O—$(C_1$–$C_6)$-alkyl, in which R8 is
    i) hydrogen atom
    ii) —$(C_1$–$C_6)$-alkyl, in which alkyl is unsubstituted or substituted, once, twice or three times, independently of each other, by —$NH_2$, —CN, —OH, —C(O)—OH, —C(O)—O—$C_1$–$C_6$)-alkyl, —C(O)—NH—OH, $NO_2$ or halogen, or
    iii) OH,
3. —C(O)—N(R9)-(R10), in which R9 and R10 are identical or different and are, independently of each other,
    i) hydrogen atom or
    ii) —$(C_1$–$C_6)$-alkyl, or R9 and R10 form, together with the nitrogen atom to which they are bonded, a 5-, 6- or 7-membered saturated ring where a heteroatom from the series oxygen, sulfur and nitrogen can also replace one or two further carbon atoms and, in the case of nitrogen, the nitrogen atoms can, independently of each other, be unsubstituted or substituted by $(C_1$–$C_6)$-alkyl,
4. phenyl, in which phenyl is substituted, once, twice or three times, independently of each other, by
    4.1) —$(C_0$–$C_6)$-alkyl-C(O)—O—R8, in which R8 has the abovementioned meaning,
    4.2) —$(C_0$–$C_6)$-alkyl-C(O)—N(R9)-(R10), in which R9 and R10 have the abovementioned meaning,
    4.3) —$(C_0$–$C_6)$-alkyl-C(O)—NH—CN,
    4.4) —$(C_0$–$C_6)$-alkyl-C(O)—$(C_0$–$C_6)$-alkyl-Het, where Het is a radical from the group: azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxiran, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole, and in which Het is unsubstituted or substituted, once, twice or three times, independently of each other, by
    a) halogen,
    b) cyano,
    c) nitro,
    d) hydroxyl,
    e) amino,
    f) —C(O)—O—$(C_1$–$C_6)$-alkyl,
    g) —C(O)—OH,
    h) —$(C_1$–$C_6)$-alkyl, where alkyl is unsubstituted or substituted, once, twice or three times, by halogen,
    i) —O—$(C_1$–$C_6)$-alkyl, where alkyl is unsubstituted or substituted, once, twice or three times, by halogen, or —N(R9)-(R10),
    j) =O,
    k) -Het, in which Het is defined as above,
    l) —$(C_2$–$C_6)$-alkenyl, where alkenyl is unsubstituted or substituted, once, twice or three times, by halogen, or —N(R9)-(R10), or
    m) —$(C_2$–$C_6)$-alkynyl, where alkynyl is unsubstituted or substituted, once, twice or three times, by halogen or —N(R9)-(R10),
    4.5) —$(C_0$–$C_6)$-alkyl-C(O)—$(C_0$–$C_6)$-alkyl-OH,
    4.6) —O—$(C_0$–$C_6)$-alkyl-C(O)—N(R9)-(R10), in which R9 and R10 have the abovementioned meaning,
    4.7) —$(C_0$–$C_6)$-alkyl-C(O)—N(R8)-$(C_0$–$C_6)$-alkyl-N(R9)-(R10), in which R8, R9 and R10 have the abovementioned meaning,
    4.8) —$(C_0$–$C_4)$-alkyl-N(R8)-$S(O)_2$—$(C_0$–$C_6)$-alkyl-Het, in which Het is defined as above and is unsubstituted or substituted, once, twice or three times, independently of each other, by the abovementioned radicals a) to m) and R8 has the abovementioned meaning,
    4.9) —$(C_0$–$C_4)$-alkyl-$S(O)_2$—$(C_0$–$C_6)$-alkyl-$(C_6$–$C_{14})$-phenyl, in which phenyl is unsubstituted or substituted, once, twice or three times, independently of each other, by the abovementioned radicals a) to m),
    4.10) —$(C_0$–$C_6)$-alkyl-C(O)—N(R8)-$(C_0$–$C_6)$-alkyl-Het, where R8 has the abovementioned meaning and Het has the abovementioned meaning and is unsubstituted or substituted, once, twice or three times, independently of each other, by the abovementioned radicals a) to m),
    4.11) —$(C_0$–$C_6)$-alkyl-C(O)—N(R8)-$(C_0$–$C_6)$-alkyl-$(C_6$–$C_{14})$-phenyl, where phenyl is unsubstituted or substituted, once, twice or three times, independently of each other, by the abovementioned radicals a) to m),
    4.12) —$(C_0$–$C_6)$-alkyl-N(R9)-(R10), in which R9 and R10 have the abovementioned meaning,
    4.13) —$(CH_2)_y$—N(R8)-C(O)—$(C_1$–$C_6)$-alkyl, in which alkyl is unsubstituted or substituted, once, twice or three times, independently of each other, by the abovementioned radicals a) to m) and y is 1 or 2,
    4.14) —$(C_0$–$C_4)$-alkyl-N(R8)-C(O)—$(C_0$–$C_6)$-alkyl-$(C_6$–$C_{14})$-phenyl, in which phenyl is unsubstituted or substituted, once, twice or three times, independently of each other, by the abovementioned radicals a) to m), 4.15) —$(C_0$–$C_4)$-alkyl-N(R8)-C(O)—$(C_0$–$C_6)$-alkyl-Het, in which Het is unsubstituted or substi tuted, once, twice or three times, independently of each other, by the abovementioned radicals a) to m), 4.16) —($C_0$–$C_4$)-alkyl-N(R8)-C(O)—O—($C_1$–$C_6$)-alkyl, in which alkyl is unsubstituted or substituted, once, twice or three times, independently of each other, by the abovementioned radicals a) to m), 4.17) —($C_0$–$C_4$)-alkyl-N(R8)-C(O)—O—($C_1$–$C_6$)-alkenyl, in which alkenyl is unsubstituted or substituted, once, twice or three times, independently of each other, by the abovementioned radicals a) to m), 4.18) —($C_0$–$C_4$)-alkyl-N(R8)-C(O)—O—($C_1$–$C_6$)-alkynyl, in which alkynyl is unsubstituted or substituted, once, twice or three times, independently of each other, by the abovementioned radicals a) to m), 4.19) —($C_0$–$C_4$)-alkyl-N(R8)-C(O)—O—($C_0$–$C_6$)-alkyl-($C_6$–$C_{14}$)-phenyl, in which phenyl is unsubstituted or substituted, once, twice or three times, independently of each other, by the abovementioned radicals a) to m), 4.20) —($C_0$–$C_4$)-alkyl-N(R8)-C(O)—O—($C_0$–$C_6$)-alkyl-Het, in which Het is defined as above and is unsubstituted or substituted, once, twice or three times, independently of each other, by the abovementioned radicals a) to m), 4.21) —($C_0$–$C_4$)-alkyl-N(R8)-C(O)—($C_0$–$C_6$)-alkyl-N(R11)-R12, in which R8 has the abovementioned meaning and R11 and R12 are identical or different and are, independently of each other, 4.21.1) a hydrogen atom, 4.21.2) —($C_1$–$C_6$)-alkyl, 4.21.3) —($C_0$–$C_6$)-alkyl-($C_6$–$C_{14}$)-phenyl, in which phenyl is unsubstituted or substituted, once, twice or three times, independently of each other, by the abovementioned radicals a) to m), 4.21.4) —($C_0$–$C_6$)-alkyl-Het, in which Het is defined as above and is unsubstituted or substituted, once, twice or three times, independently of each other, by the abovementioned radicals a) to m), 4.21.5) —C(O)—($C_1$–$C_6$)-alkyl, in which alkyl is unsubstituted or substituted, once, twice or three times, independently of each other, by the abovementioned radicals a) to m), 4.21.6) —C(O)—($C_3$–$C_6$)-cycloalkyl, in which cycloalkyl is unsubstituted or substituted, once, twice or three times, independently of each other, by the abovementioned radicals a) to m), 4.21.7) —C(O)—($C_0$–$C_6$)-alkyl-($C_6$–$C_{14}$)-phenyl, in which phenyl is unsubstituted or substituted, once, twice or three times, independently of each other, by the abovementioned radicals a) to m), 4.21.8) —C(O)—($C_0$–$C_6$)-alkyl-Het, in which Het is defined as above and is unsubstituted or substituted, once, twice or three times, independently of each other, by the abovementioned radicals a) to m), 4.21.9) —$SO_2$—($C_0$–$C_6$)-alkyl, in which alkyl is unsubstituted or substituted, once, twice or three times, independently of each other, by the abovementioned radicals a) to m), 4.21.10) —NH—$SO_2$—($C_0$–$C_6$)-alkyl, in which alkyl is unsubstituted or substituted, once, twice or three times, independently of each other, by the abovementioned radicals a) to m), 4.21.11) —$SO_2$—($C_0$–$C_6$)-alkyl-($C_6$–$C_{14}$)-phenyl-($C_0$–$C_6$)-alkyl, in which phenyl is unsubstituted or substituted, once, twice or three times, independently of each other, by the abovementioned radicals a) to m), 4.21.12) —$SO_2$—($C_0$–$C_6$)-alkyl-Het, in which Het is defined as above and is unsubstituted or substituted, once, twice or three times, independently of each other, by the abovementioned radicals a) to m), 4.22) —O—($C_0$–$C_6$)-alkyl-Het, in which Het is defined as above and is unsubstituted or substituted, once, twice or three times, independently of each other, by the abovementioned radicals a) to m), or 4.23) —($C_0$–$C_4$)-alkyl-Het, in which Het is defined as above and is unsubstituted or substituted, once, twice or three times, independently of each other, by the abovementioned radicals a) to m), 5. —C(O)—N(R8)-($C_0$–$C_6$)-alkyl-phenyl, in which phenyl is unsubstituted or substituted, once, twice or three times, independently of each other, by the abovementioned radicals 4.1) to 4.23) or 4.4) a) to 4.4) m) and R8 has the abovementioned meaning, or 6. —C(O)—N(R8)-($C_0$–$C_6$)-alkyl-Het, in which Het is azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazol or 1,2,4-triazole, and Het is unsubstituted or substituted, once, twice or three times, independently of each other, by the abovementioned radicals 4.1) to 4.4) or 4.4) a) to 4.4) m) and R8 has the abovementioned meaning, R3, R4, R5, R6 and R7 are identical or different and are, independently of each other, 1. hydrogen atom,
2. halogen,
3. —($C_1$–$C_6$)-alkyl, in which alkyl is unsubstituted or substituted, once, twice or three times, by halogen, or
4. —O—($C_1$–$C_6$)-alkyl, in which alkyl is unsubstituted or substituted, once, twice or three times, by halogen, or R4 and R5 or R5 and R6 form, together with the carbon atoms to which they are in each case bonded, independently of each other, a dioxane, dioxole, dihydrofuran or furan ring, where the ring is unsubstituted or substituted, at one or at several carbon atoms, once or twice, by halogen and the other radicals R3, R6 and R7 or R3, R4 and R7 have the abovementioned meaning of 1. to 4, or for the case b)

R1 is hydrogen atom or —($C_1$–$C_4$)-alkyl,

R2 is —($C_1$–$C_4$)-alkyl, where alkyl is substituted, once, twice or three times, by 1. —C(O)—O—R8', in which R8' is
  1.1) hydrogen atom or
  1.2) —($C_1$–$C_4$)-alkyl,
2. —($C_1$–$C_4$)-alkyl-O—R8', in which R8' has the abovementioned meaning,
3. phenyl, in which phenyl is substituted, once, twice or three times, independently of each other, by 3.1) —($C_2$–$C_4$)-alkyl-C(O)—O—R8', in which R8' has the abovementioned meaning, 3.2) —O—($C_1$–$C_4$)-alkyl-C(O)—O—R8', in which R8' has the abovementioned meaning, 3.3) —N(R14)-(R15) in which R14 and R15 form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by ($C_1$–$C_4$)-alkyl, 3.4) —($CH_2$)$_k$—N(R9')-(R10') in which k is 2, 3, 4 or 5 and R9' and R10' are identical or different and are, independently of each other, 3.4.1) hydrogen atom or 3.4.2) —($C_1$–$C_6$)-alkyl, or R9' and R10' form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by ($C_1$–$C_4$)-alkyl, 3.5) —O—($C_2$–$C_6$)-alkyl-N(R9')-R10', where R9' and R10' have the abovementioned meaning, 3.6) —N(R8')-C(O)—($C_1$–$C_6$)-alkyl, in which alkyl is unsubstituted or substituted, once, twice or three times, by 3.6.1) halogen, 3.6.2) cyano, 3.6.3) nitro 3.6.4) hydroxyl, 3.6.5) amino, 3.6.7) —C(O)—O—($C_1$–$C_6$)-alkyl, or 3.6.8) —C(O)—OH, and R8' has the abovementioned meaning, 3.7) -phenyl, where the phenyl ring is unsubstituted or substituted, once, twice or three times, by 3.7.1) halogen, 3.7.2) —($C_1$–$C_6$)-alkyl, 3.7.3) —O—($C_1$–$C_6$)-alkyl, or 3.7.4) —S(O)$_2$—R16', where R16' is ($C_1$–$C_6$)-alkyl or —$NH_2$, 4. Het, where Het is azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole, and Het is unsubstituted or substituted, once, twice or three times, independently of each other, by 4.1) halogen, 4.2) cyano, 4.3) nitro, 4.4) hydroxyl, 4.5) amino, 4.6) —C(O)—O($C_1$–$C_6$)-alkyl, 4.7) —C(O)—OH, 4.8) —($C_1$–$C_6$)-alkyl, where alkyl is unsubstituted or substituted, once, twice or three times, by halogen, 4.9) —O—($C_1$–$C_6$)-alkyl, where alkyl is unsubstituted or substituted, once, twice or three times, by halogen, 4.10) pyridyl, or 4.11) phenyl, where phenyl is unsubstituted or substituted, once, twice or three times, independently of each other, by a radical from the series halogen, —($C_1$–$C_6$)-alkoxy and —($C_1$–$C_6$)-alkyl, and R4 and R5 or R5 and R6 form, together with the phenyl ring and the carbon atoms to which they are in each case bonded, independently of each other, a ring system from the series benzo[1,4]dioxane, 2,3-dihydrobenzofuran and 2,2-difluorobenzo[1,3]dioxole, and the other radicals R3, R6 and R7 or R3, R4 and R7 are hydrogen atom.

The invention also relates to a compound of the formula I where, for the case a), R1 is hydrogen atom, R2 is —($C_1$–$C_3$)-alkyl, where alkyl is substituted by 1. phenyl, in which phenyl is substituted, once, twice or three times, independently of each other, by 1.1) —$CH_2$—C(O)—O—R8, in which R8 is hydrogen, methyl, ethyl, propyl or butyl, 1.2) —($C_0$–$C_6$)-alkyl-C(O)—N(R9)-(R10), in which R9 and R10 are hydrogen atom, methyl, ethyl, propyl or butyl, or R9 and R10 form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by ($C_1$–$C_4$)-alkyl, 1.3) —($C_0$–$C_4$)-alkyl-C(O)—NH—CN, 1.4) —O—($C_0$–$C_6$)-alkyl-C(O)—N(R9)-(R10), in which R9 and R10 have the meaning mentioned above under 1.2), 1.5) —($C_0$–$C_6$)-alkyl-C(O)—N(R8)-($C_0$–$C_6$)-alkyl-N(R9)-(R10), in which R8, R9 and R10 have the abovementioned meaning, 1.6) —C(O)—N(R8)-($C_0$–$C_2$)-alkyl-Het, where R8 has the abovementioned meaning and Het is azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole and Het is unsubstituted or substituted, once, twice or three times, independently of each other, by a) halogen b) cyano, c) nitro,
d) hydroxyl,
e) amino,
f) —C(O)—O—($C_1$–$C_4$)-alkyl,
g) —C(O)—OH,
h) —($C_1$–$C_4$)-alkyl, where alkyl is unsubstituted or substituted, once, twice or three times, by halogen,
i) —O—($C_1$–$C_4$)-alkyl, where alkyl is unsubstituted or substituted, once, twice or three times, by halogen, or
1.7) —C(O)—N(R8)-($C_0$–$C_4$)-alkyl-phenyl, where phenyl is unsubstituted or substituted, once, twice or three times, independently of each other, by the abovementioned radicals a) to i),
1.8) —$CH_2$—N(R9)-(R10), in which R9 and R10 have the abovementioned meaning,
1.9) —$(CH_2)_y$—N(R8)-C(O)—($C_1$–$C_4$)-alkyl in which alkyl is unsubstituted or substituted, once, twice or three times, independently of each other, by the abovementioned radicals a) to i), and y is 1 or 2,
1.10) —$(CH_2)_x$—N(R8)-C(O)—($C_0$–$C_2$)-alkyl-phenyl, in which phenyl is unsubstituted or substituted, once, twice or three times, independently of each other, by the abovementioned radicals a) to i), and x is 0, 1 or 2,
1.11) —$(CH_2)_x$—N(R8)-C(O)—($C_0$–$C_2$)-alkyl-Het, in which Het is unsubstituted or substituted, once, twice or three times, independently of each other, by the abovementioned radicals a) to i), and x is 0, 1 or 2,
1.12) —$(CH_2)_x$—N(R8)-C(O)—O—($C_1$–$C_4$)-alkyl, in which alkyl is unsubstituted or substituted, once, twice or three times, independently of each other, by the abovementioned radicals a) to i), and x is 0, 1 or 2,
1.13) —$(CH_2)_x$—N(R8)-C(O)—O—($C_0$–$C_4$)-alkyl-phenyl, in which phenyl is unsubstituted or substituted, once, twice or three times, independently of each other, by the abovementioned radicals a) to i), and x is 0, 1 or 2,
1.14) —$(CH_2)_x$—N(R8)-C(O)—O—($C_0$–$C_4$)-alkyl-Het in which Het is unsubstituted or substituted, once, twice or three times, independently of each other, by the abovementioned radicals a) to i), and x is 0, 1 or 2,
1.15) —$(CH_2)_x$—N(R8)-C(O)—N(R11)-R12, in which R8 and x have the abovementioned meaning and R11 and R12 are identical or different and are, independently of each other,
1.15.1) hydrogen atom,
1.15.2) methyl, ethyl, propyl or butyl,
1.15.3) —($C_0$–$C_2$)-alkyl-phenyl, in which phenyl is unsubstituted or substituted, once, twice or three times, independently of each other, by the abovementioned radicals a) to i),
1.15.4) —($C_0$–$C_2$)-alkyl-Het, in which Het is unsubstituted or substituted, once, twice or three times, independently of each other, by the abovementioned radicals a) to i),
1.15.5) —C(O)—($C_1$–$C_4$)-alkyl,
1.15.6) —C(O)—($C_0$–$C_2$)-alkyl-phenyl,
1.15.7) —C(O)—($C_0$–$C_2$)-alkyl-Het,
1.15.8) —$SO_2$—($C_1$–$C_4$)-alkyl,
1.15.9) —$SO_2$—($C_0$–$C_4$)-alkyl-phenyl, or
1.15.10) —$SO_2$—($C_0$–$C_2$)-alkyl-Het, R3, R4, R5, R6 and R7 are identical or different and are, independently of each other,
1. hydrogen atom,
2. halogen,
3. —($C_1$–$C_6$)-alkyl, in which alkyl is unsubstituted or substituted, once, twice or three times, by halogen,
4. —O—($C_1$–$C_6$)-alkyl in which alkyl is unsubstituted or substituted, once, twice or three times, by halogen, or R4 and R5 or R5 and R6 form, together with the carbon atoms to which they are bonded, independently of each other, a dioxane, dioxole, dihydrofuran or furan ring and the other radicals R3, R6 and R7 or R3, R4 and R7 have the abovementioned meaning of 1. to 4., or, for the case b), R1 is hydrogen atom,
R2 is —($C_1$–$C_2$)-alkyl, where alkyl is substituted, once, twice or three times, by
1. —C(O)—O—R8', in which R8' is
  1.1) hydrogen atom or
  1.2) —($C_1$–$C_2$)-alkyl,
2. phenyl, in which phenyl is substituted, once, twice or three times, independently of each other, by
  2.1) —O—($C_2$–$C_4$)-alkyl-N(R9')-R10', where R9' and R10' are, independently of each other, hydrogen atom, methyl or ethyl, or R9' and R10' form, together with the nitrogen atom to which they are bonded, a radical which can be derived from pyrrolidine, piperidine, piperazine, morpholine or thiomorpholine, and, in the case of piperazine, the second nitrogen atom can be substituted by methyl or ethyl,
  2.2) —O—($C_1$–$C_2$)-alkyl-C(O)—O—R8', in which R8' is, independently of each other, hydrogen atom, methyl or ethyl, or
  2.3) —N(R14)-(R15) in which R14 and R15 form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by methyl or ethyl,
  2.4) —$(CH_2)_k$—N(R9')-(R10') in which k is 2, 3 or 4 and R9' and R10' are identical or different and are, independently of each other, hydrogen atom, methyl or ethyl, or R9' and R10' form, together with the nitrogen atom to which they are bonded, a radical which can be derived from pyrrolidine, piperidine, piperazine, morpholine or thiomorpholine, and, in the case of piperazine, the second nitrogen atom can be substituted by methyl or ethyl, and R4 and R5 or R5 and R6 form, together with the phenyl ring and the carbon atoms to which they are in each case bonded, independently of each other, a ring system from the series benzo[1,4]dioxane, 2,3-dihydrobenzofuran and 2,2-difluorobenzo[1,3]dioxole, and the other radicals R3, R6 and R7 or R3, R4 and R7 are hydrogen atom.

The invention also relates to the use of a compound of the formula I,

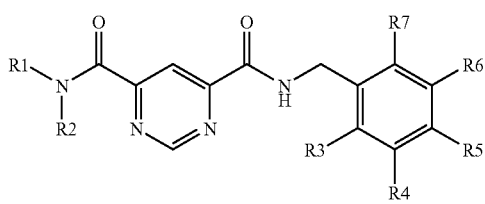

and/or all the stereoisomeric forms of the compound of the formula I and/or mixtures of these forms in any ratio, and/or a physiologically tolerated salt of the compound of the formula I, for producing a pharmaceutical for the prophylaxes and therapy of diseases in whose course an increase in the activity of matrix metalloproteinase 13 is involved.

Definition of Terms

As used above, and throughout the description of the invention, the following terms, unless otherwise indicated, shall be understood to have the following meanings.

The term "halogen" is understood as meaning fluorine, chlorine, bromine or iodine.

The term "alkyl" is understood as meaning, in the widest possible sense, hydrocarbon radicals whose carbon chain is straight-chain or branched or which are composed of cyclic hydrocarbon groups or of combinations of linear and cyclic groups. For example, linear and branched hydrocarbon radicals can be methyl, ethyl, propyl, i-propyl, butyl, tert-butyl, pentyl or hexyl, while cyclic groups can be cyclopropyl, cyclobutyl, cyclopentyl or cyclohexyl and a combination of linear and cyclic radicals can be cyclopropylmethyl, cyclobutylmethyl or cyclopentylmethyl. However, alkyl can also be singly or multiply unsaturated, such as $(C_2–C_6)$-alkenyl, e.g. ethylene, propylene, butene, methylpropene, isobutylene, 1,3-butadiene or 1,3-pentadiene, or $(C_2–C_6)$-alkynyl, e.g. acetylene, propylyne, butyne, 2-methyl-3-hexyne, 1,4-pentadiyne or 2-hexen-4-yne.

The term "—$(C_0–C_6)$-alkyl" is understood as meaning hydrocarbon radicals whose carbon chain is straight-chain or branched and contains from 1 to 6 carbon atoms, for example methyl, ethyl, propyl, i-propyl, butyl, tert-butyl, pentyl or hexyl. "—$C_0$-alkyl" is a covalent bond.

The term "—$(C_6–C_{14})$-aryl" is understood as meaning aromatic carbon radicals having from 6 to 14 carbon atoms in the ring. Examples of —$(C_6–C_{14})$-aryl radicals are phenyl, naphthyl, for example 1-naphthyl and 2-naphthyl, biphenylyl, for example 2-biphenylyl, 3-biphenylyl and 4-biphenylyl, anthryl and fluorenyl. Biphenylyl radicals, naphthyl radicals and, in particular, phenyl radicals are preferred aryl radicals.

The term "R4 and R5 or R5 and R6 form, together with the carbon atoms to which they are in each case bonded, independently of each other, a 5- or 6-membered ring which is aromatic or saturated and contains zero, one or two heteroatoms from the series oxygen, nitrogen or sulfur" is understood as meaning ring systems which can be derived from dioxole, pyrrole, pyrrolidine, pyridine, piperidine, dioxane, tetrahydropyridine, pyrazole, imidazole, pyrazoline, imidazoline, pyrazolidine, imidazolidine, pyridazine, pyrimidine, pyrazine, piperazine, pyran, furan, dihydrofuran, tetrahydrofuran, oxazole, isoxazole, 2-isoxazoline, isoxazolidine, morpholine, oxothiolane, thiopyran, thiazole, isothiazole, 2-isothiazoline, isothiazolidine or thiomorpholine.

The term "Het" is understood as meaning a saturated or unsaturated monocyclic or bicyclic, 3- to 10-membered heterocyclic ring system which contains 1, 2 or 3 identical or different ring heteroatoms from the series nitrogen, oxygen and sulfur. In the underlying monocyclic or bicyclic heterocyclic ring system, Het contains 3, 4, 5, 6, 7, 8, 9, or 10 ring atoms. The monocyclic ring system can be a 3-, 4-, 5-, 6- or 7-membered ring. In the bicyclic Het, two rings can be linked to each other, with it being possible for one of the rings to be a 5-membered or 6-membered heterocyclic ring and the other to be a 5- or 6-membered heterocyclic or carbocyclic ring. A bicyclic Het group can be composed, for example, of 8, 9 or 10 ring atoms.

Het comprises saturated heterocyclic ring systems which do not possess any double bond in the rings and also unsaturated heterocyclic ring systems, including monounsaturated and polyunsaturated heterocyclic ring systems, which possess one or more double bonds and form a stable ring system. Unsaturated rings can be partially unsaturated or form an aromatic system. The Het group contains identical or different heteroatoms from the series nitrogen, oxygen and sulfur. Examples of heterocycles from which the Het group can be derived are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H-6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl and xanthenyl.

Preference is given to azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole etc. and also to ring systems which result from the listed heterocycles by the latter being linked to, or fused with, a carbocyclic ring, for example benzo fused, cyclopenta fused, cyclohexa fused or cyclohepta fused derivatives of these heterocycles. Suitable nitrogen heterocycles can also be present as N-oxides or as quaternary salts in which a suitable nitrogen atom is alkylated with $(C_1–C_4)$-alkyl radicals. The Het groups can be unsubstituted or substituted in accordance with the listed definitions.

The term "R9 and R10 or R14 and R15 form, together with the nitrogen atom to which they are bonded, a 5-, 6- or 7-membered saturated ring, where a heteroatom from the series oxygen, sulfur and nitrogen can also replace one or two further carbon atoms" is understood as meaning radicals which can be derived from imidazolidine, isothiazolidine, isoxazolidine, morpholine, piperazine, piperidine, pyrazine, pyrazolidine, pyrrolidine, tetrazine or thiomorpholine.

The term "patient" includes both human and other mammals.

"Pharmaceutically effective amount" is meant to describe an amount of a compound, composition, medicament or other active ingredient effective in producing the desired therapeutic effect.

"Optionally substituted" means either unsubstituted or substituted one or more times by substituents, which may be the same, or different.

DETAILED DESCRIPTION OF THE INVENTION

The invention also relates to a compound of the formula I such as pyrimidine-4,6-carboxylic acid 4-(3-methoxybenzylamide) 6-(4-propylcarbamoyl benzylamide), pyrimidine-4,6-carboxylic acid 4-(4-isopropylcarbamoylbenzylamide) 6-(3-methoxybenzylamide),

[4-({[6-(3-methoxybenzylcarbamoyl)pyrimidine-4-carbonyl]amino}methyl)phenyl]carboxyamino isopropyl ester, pyrimidine-4,6-carboxylic acid 4-(3-methoxybenzylamide) 6-[(2-phenoxy-ethyl)amide], (5-{[6-(3-methoxybenzylcarbamoyl)pyrimidine-4-carbonyl]amino}pentyl)carboxyamino methyl ester, pyrimidine-4,6-carboxylic acid 4-[4-(2-dimethylaminoethylcarbamoyl)benzylamide] 6-(3-methoxybenzylamide), pyrimidine-4,6-carboxylic acid 4-[(2,3-dihydrobenzo[1,4]dioxin-6-ylmethyl)amide] 6-[4-(2-dimethylaminoethylcarbamoyl)benzylamide], pyrimidine-4,6-carboxylic acid 4-(3-chloro-4-fluorobenzylamide) 6-[4-(2-dimethylaminoethylcarbamoyl)benzylamide], pyrimidine-4,6-carboxylic acid 4-dimethylcarbamoylmethylamide 6-(3-methoxybenzylamide),

[4-({[6-(3-aminobenzylcarbamoyl)pyrimidine-4-carbonyl]amino}methyl)phenyl]carboxyamino tert-butyl ester, pyrimidine-4,6-dicarboxylic acid 4-(3-chlorobenzylamide) 6-(4-fluoro-3-methylbenzylamide), pyrimidine-4,6-dicarboxylic acid 4-[(2-chloropyridin-4-ylmethyl)amide] 6-(4-fluoro-3-methylbenzylamide), pyrimidine-4,6-dicarboxylic acid 4-benzylamide 6-(4-fluoro-3-methylbenzylamide), pyrimidine-4,6-dicarboxylic acid 4-(4-fluoro-3-methylbenzylamide) 6-[(pyridin-4-ylmethyl)amide], pyrimidine-4,6-dicarboxylic acid 4-(4-fluoro-3-methylbenzylamide) 6-(pyridin-3-ylmethyl)amide], pyrimidine-4,6-carboxylic acid 4-(4-fluoro-3-methylbenzylamide) 6-{4-[2-(4-methylpiperazin-1-yl)-2-oxoethyl]benzylamide}, pyrimidine-4,6-carboxylic acid 4-(4-fluoro-3-methylbenzylamide) 6-[4(2-morpholin-4-yl-2-oxoethoxy)benzylamide], pyrimidine-4,6-carboxylic acid 4-(4-diethylcarbamoylmethoxybenzylamide) 6-(4-fluoro-3-methylbenzylamide), pyrimidine-4,6-carboxylic acid 4-(4-fluoro-3-methylbenzylamide) 6-[4-(isopropylcarbamoylmethyl)benzylamide], pyrimidine-4,6-carboxylic acid 4-(4-fluoro-3-methylbenzylamide) 6-{4-[(2-morpholin-4-ylethylcarbamoyl)methyl]benzylamide}, pyrimidine-4,6-carboxylic acid 4-(4-diethylcarbamoylmethylbenzylamide) 6-(4-fluoro-3-methylbenzylamide), pyrimidine-4,6-carboxylic acid 4-(4-fluoro-3-methylbenzylamide) 6-[4-(2-morpholin-4-yl-2-oxoethyl)benzylamide], pyrimidine-4,6-carboxylic acid 4-(4-fluoro-3-methylbenzylamide) 6-[4-(isopropylcarbamoylmethoxy)benzylamide], pyrimidine-4,6-dicarboxylic acid 4-(3-methoxybenzylamide) 6-[(pyridin-3-ylmethyl) amide], pyrimidine-4,6-carboxylic acid 4-(3-methoxybenzylamide) 6-({[(pyridin-4-ylmethyl) carbamoyl]methyl}amide), pyrimidine-4,6-carboxylic acid 4-({[(2-chloropyridin-4-ylmethyl)carbamoyl]-methyl}amide) 6-(3-methoxybenzylamide), pyrimidine-4,6-carboxylic acid 4-(3-chloro-4-fluorobenzylamide) 6-({[(2-chloropyridin-4-ylmethyl)carbamoyl]methyl}amide),

[4-({[6-(3-methoxybenzylcarbamoyl)pyrimidine-4-carbonyl]amino}methyl)-phenyl]carboxyamino isobutyl ester,

[4-({[6-(3-methoxybenzylcarbamoyl)pyrimidine-4-carbonyl]amino}methyl)-phenyl]carboxyamino ethyl ester,

[4-({[6-(3-methoxybenzylcarbamoyl)pyrimidine-4-carbonyl]amino}methyl)-phenyl]carboxyamino allyl ester, pyrimidine-4,6-carboxylic acid 4-(3-chloro-4-fluorobenzylamide) 6-[4-(1-methylpiperidin-3-yloxy)benzylamide], pyrimidine-4,6-carboxylic acid 4-(3-chloro-4-fluorobenzylamide) 6-({[(pyridin-3-ylmethyl)carbamoyl]methyl}amide), pyrimidine-4,6-carboxylic acid 4-(3-methoxybenzylamide) 6-[4-(2-morpholin-4-ylethylcarbamoyl)benzylamide], pyrimidine-4,6-carboxylic acid 4-(3-methoxybenzylamide) 6-[4-(2-pyrrolidin-1-yl-ethylcarbamoyl)benzylamide], pyrimidine-4,6-carboxylic acid 4-[(2,3-dihydrobenzo[1,4]dioxin-6-ylmethyl)amide] 6-[(2'-sulfamoylbiphenyl-2-ylmethyl)amide], pyrimidine-4,6-carboxylic acid 4-[(2,3-dihydrobenzofuran-5-ylmethyl)amide] 6-[(thiophen-2-ylmethyl)amide], pyrimidine-4,6-carboxylic acid 4-[(2,3-dihydrobenzofuran-5-ylmethyl)amide] 6-[(5-methylfuran-2-ylmethyl)amide], pyrimidine-4,6-carboxylic acid 4-[(2,3-dihydrobenzofuran-5-ylmethyl)amide] 6-[(5-methylfuran-2-ylmethyl)amide], pyrimidine-4,6-carboxylic acid 4-[(2,3-dihydrobenzofuran-5-ylmethyl)amide] 6-[(5-pyridin-2-ylthiophen-2-ylmethyl)amide], pyrimidine-4,6-carboxylic acid 4-[(2,3-dihydrobenzofuran-5-ylmethyl)amide] 6-[(pyridin-3-ylmethyl)amide], pyrimidine-4,6-carboxylic acid 4-[(2,3-dihydrobenzo[1,4]dioxin-6-ylmethyl)amide] 6-[(pyridin-3-ylmethyl) amide], pyrimidine-4,6-carboxylic acid 4-[(2,3-dihydrobenzo[1,4]dioxin-6-ylmethyl)amide] 6-[(5-methylfuran-2-ylmethyl) amide], pyrimidine-4,6-carboxylic acid 4-[(2,3-dihydrobenzo[1,4]dioxin-6-ylmethyl)amide] 6-[(thiophen-2-ylmethyl) amide];

pyrimidine-4,6-carboxylic acid 4-[(2,3-dihydrobenzofuran-5-ylmethyl)amide] 6-[(5-methylisoxazol-3-ylmethyl) amide], pyrimidine-4,6-carboxylic acid 4-[(2,3-dihydrobenzofuran-5-ylmethyl)amide] 6-[(1-methyl-1H-pyrazol-4-ylmethyl)amide],
pyrimidine-4,6-carboxylic acid 4-[(2,3-dihydrobenzofuran-5-ylmethyl)amide] 6-[(2,5-dimethylfuran-3-ylmethyl)amide],
pyrimidine-4,6-carboxylic acid 4-[(6-aminopyridin-3-ylmethyl)amide] 6-[(2,3-dihydrobenzofuran-5-ylmethyl)amide],
pyrimidine-4,6-carboxylic acid 4-[(2,3-dihydrobenzofuran-5-ylmethyl)amide] 6-[(1-methyl-1H-pyrrol-2-ylmethyl)amide],
pyrimidine-4,6-carboxylic acid 4-[(1H-benzoimidazol-2-ylmethyl)amide] 6-[(2,3-dihydrobenzofuran-5-ylmethyl)amide],
pyrimidine-4,6-carboxylic acid 4-[(2,3-dihydrobenzofuran-5-ylmethyl)amide] 6-[(pyrazin-2-ylmethyl)amide],
pyrimidine-4,6-carboxylic acid 4-[(2,2-difluorobenzo[1,3]dioxol-5-ylmethyl)amide] 6-[(pyridin-4-ylmethyl)amide],
({6-[(2,3-dihydrobenzo[1,4]dioxin-6-ylmethyl)carbamoyl]pyrimidine-4-carbonyl}amino)acetic acid methyl ester,
pyrimidine-4,6-carboxylic acid 4-[(2,3-dihydrobenzofuran-5-ylmethyl)amide] 6-[(2-methyl-1H-imidazol-4-ylmethyl)amide],
pyrimidine-4,6-carboxylic acid 4-[(2,3-dihydrobenzofuran-5-ylmethyl)amide] 6-[(2-pyridin-2-ylethyl)amide],
pyrimidine-4,6-carboxylic acid 4-[(2,3-dihydrobenzofuran-5-ylmethyl)amide] 6-{[3-(4-fluorophenyl)-1H-pyrazol-4-ylmethyl]amide},
pyrimidine-4,6-carboxylic acid 4-[(2,3-dihydrobenzo[1,4]dioxin-6-ylmethyl)amide] 6-[4-(3-dimethylaminopropoxy)benzylamide],
pyrimidine-4,6-carboxylic acid 4-[(2,3-dihydrobenzo[1,4]dioxin-6-ylmethyl)amide] 6-[4-(2-dimethylaminoethoxy)benzylamide],
pyrimidine-4,6-carboxylic acid 4-[(2,3-dihydrobenzo[1,4]dioxin-6-ylmethyl)amide] 6-[3-(2-dimethylaminoethoxy)benzylamide],
pyrimidine-4,6-carboxylic acid 4-[(2,3-dihydrobenzofuran-5-ylmethyl)amide] 6-[(pyridin-4-ylmethyl)amide],
pyrimidine-4,6-dicarboxylic acid 4-(3-chloro-4-fluorobenzylamide) 6-(4-[3'-methylsulfonyl]ureidobenzylamide),
pyrimidine-4,6-dicarboxylic acid 4-(3-methoxybenzylamide) 6-[4-(4-oxopiperidine-1-carbonyl)benzylamide],
pyrimidine-4,6-dicarboxylic acid 4-(4-fluoro-3-methylbenzylamide) 6-[4-(4-oxopiperidine-1-carbonyl)benzylamide],
pyrimidine-4,6-dicarboxylic acid 4-[(2,3-dihydrobenzofuran-5-ylmethyl)amide] 6-[4-(4-oxopiperidine-1-carbonyl)benzylamide],
pyrimidine-4,6-dicarboxylic acid 4-[4-(4-hydroxypiperidine-1-carbonyl)benzylamide] 6-(3-methoxybenzylamide),
pyrimidine-4,6-dicarboxylic acid 4-[(2,3-dihydrobenzofuran-5-ylmethyl)amide] 6-[4-(4-hydroxypiperidine-1-carbonyl)benzylamide],
pyrimidine-4,6-dicarboxylic acid 4-(4-fluoro-3-methylbenzylamide) 6-[4-(4-hydroxypiperidine-1-carbonyl)benzylamide],
pyrimidine-4,6-dicarboxylic acid 4-(4-fluoro-3-methylbenzylamide) 6-[4-(thiomorpholine-4-carbonyl)benzylamide],
pyrimidine-4,6-dicarboxylic acid 4-(3-methoxybenzylamide) 6-[4-(thiomorpholine-4-carbonyl)benzylamide],
pyrimidine-4,6-dicarboxylic acid 4-[(2,3-dihydrobenzofuran-5-ylmethyl)amide] 6-[4-(thiomorpholine-4-carbonyl)benzylamide],
pyrimidine-4,6-dicarboxylic acid 4-(3-methoxybenzylamide) 6-[4-(3-oxopiperazine-1-carbonyl)benzylamide],
pyrimidine-4,6-dicarboxylic acid 4-[(2,3-dihydrobenzofuran-5-ylmethyl)amide] 6-[4-(3-oxopiperazine-1-carbonyl)benzylamide],
pyrimidine-4,6-dicarboxylic acid 4-(4-fluoro-3-methylbenzylamide) 6-[4-(3-oxopiperazine-1-carbonyl)benzylamide],
pyrimidine-4,6-dicarboxylic acid 4-[(2,3-dihydrobenzofuran-5-ylmethyl)amide] 6-[4-(2-hydroxyethylcarbamoyl)benzylamide],
pyrimidine-4,6-dicarboxylic acid 4-(4-fluoro-3-methylbenzylamide) 6-[4-(2-hydroxyethylcarbamoyl)benzylamide],
pyrimidine-4,6-dicarboxylic acid 4-(4-fluoro-3-methylbenzylamide) 6-{4-[(pyridin-4-ylmethyl)carbamoyl]benzylamide},
pyrimidine-4,6-dicarboxylic acid 4-(4-cyanocarbamoylbenzylamide) 6-(4-fluoro-3-methylbenzylamide),
pyrimidine-4,6-dicarboxylic acid 4-(3-methoxybenzylamide) 6-[4-(3-morpholin-4-ylpropylcarbamoyl)benzylamide],
pyrimidine-4,6-dicarboxylic acid 4-[(2,3-dihydrobenzofuran-5-ylmethyl)amide] 6-[4-(3-morpholin-4-yl-propylcarbamoyl)benzylamide],
pyrimidine-4,6-dicarboxylic acid 4-(4-fluoro-3-methylbenzylamide) 6-[4-(4-methylpiperazine-1-carbonyl)benzylamide],
pyrimidine-4,6-dicarboxylic acid 4-[(2,3-dihydrobenzofuran-5-ylmethyl)amide] 6-{4-[(pyridin-4-ylmethyl)carbamoyl]benzylamide},
pyrimidine-4,6-dicarboxylic acid 4-(4-fluoro-3-methylbenzylamide) 6-(4-[3'-methylsulfonyl]ureidobenzylamide),
pyrimidine-4,6-dicarboxylic acid 4-[(2,3-dihydrobenzofuran-5-ylmethyl)amide] 6-(4-[3-methylsulfonyl]ureidobenzylamide),
pyrimidine-4,6-dicarboxylic acid 4-(4-N-cyanocarbamoylbenzylamide) 6-[(2,3-dihydrobenzofuran-5-ylmethyl)amide],
pyrimidine-4,6-dicarboxylic acid 4-(4-N-cyanocarbamoylbenzylamide) 6-(3-methoxybenzylamide),
pyrimidine-4,6-dicarboxylic acid 4-(4-fluoro-3-methylbenzylamide) 6-[4-(morpholine-4-carbonyl)benzylamide],
pyrimidine-4,6-dicarboxylic acid 4-(3-methoxybenzylamide) 6-(3-[3'-methylsulfonyl]ureidobenzylamide),
pyrimidine-4,6-dicarboxylic acid 4-(4-hydroxycarbamoylbenzylamide) 6-(3-methoxybenzylamide),
pyrimidine-4,6-dicarboxylic acid 4-[(2,3-dihydrobenzofuran-5-ylmethyl)amide] 6-[4-(hydroxycarbamoylmethylcarbamoyl)benzylamide],
pyrimidine-4,6-dicarboxylic acid 4-[(2,3-dihydrobenzofuran-5-ylmethyl)amide] 6-[4-(1-methylpiperidin-3-yloxy)benzylamide],
pyrimidine-4,6-dicarboxylic acid 4-(4-fluoro-3-methylbenzylamide) 6-[4-(2-piperazin-1-ylethylcarbamoyl)benzylamide],
pyrimidine-4,6-dicarboxylic acid 4-(4-fluoro-3-methylbenzylamide) 6-(4-hydroxycarbamoylbenzylamide),
pyrimidine-4,6-dicarboxylic acid 4-[(2,3-dihydrobenzofuran-5-ylmethyl)amide] 6-(4-hydroxycarbamoylbenzylamide),
pyrimidine-4,6-dicarboxylic acid 4-(4-fluoro-3-methylbenzylamide) 6-[4-(1-methylpiperidin-3-yloxy)benzylamide], pyrimidine-4,6-dicarboxylic acid 4-(4-tert-butylcarbamoyl-benzylamide) 6-(3-methoxybenzylamide), pyrimidine-4,6-dicarboxylic acid 4-(3-methoxybenzylamide) 6-{4-[methyl-(1-methylpiperidin-4-yl)carbamoyl]benzylamide}, {4-[({6-[(2,3-dihydrobenzofuran-5-ylmethyl)carbamoyl]pyrimidin-4-carbonyl}amino)methyl]benzoylamino}acetic acid, pyrimidine-4,6-dicarboxylic acid 4-(4-fluoro-3-methylbenzylamide) 6-[4-(2-pyrrolidin-1-yl-ethylcarbamoyl)benzylamide], pyrimidine-4,6-dicarboxylic acid 4-{4-[4-(2-dimethylaminoethyl)piperazine-1-carbonyl]benzylamide} 6-(3-methoxybenzylamide), pyrimidine-4,6-dicarboxylic acid 4-(3-methoxybenzylamide) 6-(4-[3'-methylsulfonyl]ureidobenzylamide), pyrimidine-4,6-dicarboxylic acid 4-(3-methoxybenzylamide) 6-[3-(2-morpholin-4-ylethylcarbamoyl)benzylamide],

[4-({[6-(4-fluoro-3-methylbenzylcarbamoyl)pyrimidin-4-carbonyl]amino}methyl) benzoylamino]acetic acid, pyrimidine-4,6-dicarboxylic acid 4-(3-methoxybenzylamide) 6-[4-(2-piperazin-1-ylacetylamino)benzylamide], pyrimidine-4,6-dicarboxylic acid 4-(4-fluoro-3-methylbenzylamide) 6-[4-(2-morpholin-4-yl-ethylcarbamoyl)benzylamide],

[4-({[6-(4-fluoro-3-methylbenzylcarbamoyl)pyrimidin-4-carbonyl]amino}methyl) benzoylamino]acetic acid methyl ester, pyrimidine-4,6-dicarboxylic acid 4-(3-methoxybenzylamide) 6-[3-(morpholine-4-carbonyl)benzylamide], pyrimidine-4,6-dicarboxylic acid 4-(3-methoxybenzylamide) 6-{4-[(piperidin-4-ylmethyl)carbamoyl]benzylamide}, pyrimidine-4,6-dicarboxylic acid 4-(3-methoxybenzylamide) 6-[4-(piperidin-4-ylcarbamoyl)benzylamide], pyrimidine-4,6-dicarboxylic acid 4-(4-fluoro-3-methylbenzylamide) 6-[4-(piperidin-4-ylcarbamoyl)benzylamide], pyrimidine-4,6-dicarboxylic acid 4-(4-fluoro-3-methylbenzylamide) 6-{4-[methyl-(1-methylpiperidin-4-yl)carbamoyl]benzylamide}, pyrimidine-4,6-dicarboxylic acid 4-(4-fluoro-3-methylbenzylamide) 6-[(4-methyl-3,4-dihydro-2H-benzo[1,4]oxazin-7-ylmethyl)amide], pyrimidine-4,6-dicarboxylic acid 4-(4-fluoro-3-methylbenzylamide) 6-{4-[(piperidin-4-ylmethyl)carbamoyl]benzylamide}, pyrimidine-4,6-dicarboxylic acid 4-(3-methoxybenzylamide) 6-[4-(4-methylpiperazine-1-carbonyl)benzylamide], pyrimidine-4,6-dicarboxylic acid 4-(3-methoxybenzylamide) 6-[4-(4-pyridin-4-ylpiperazine-1-carbonyl)benzylamide], pyrimidine-4,6-dicarboxylic acid 4-(3-methoxybenzylamide) 6-[4-(2-morpholin-4-ylacetylamino)benzylamide], pyrimidine-4,6-dicarboxylic acid 4-[(2,3-dihydrobenzofuran-5-ylmethyl)amide] 6-[4-(morpholine-4-carbonyl)benzylamide], pyrimidine-4,6-dicarboxylic acid 4-(3-methoxybenzylamide) 6-(4-[p-toluenesulfonyl]ureidobenzylamide), pyrimidine-4,6-dicarboxylic acid 4-[(2,3-dihydrobenzofuran-5-ylmethyl)amide] 6-[4-(4-methylpiperazine-1-carbonyl)benzylamide], pyrimidine-4,6-dicarboxylic acid 4-[(2,3-dihydrobenzofuran-5-ylmethyl)amide] 6-[4-(2-pyrrolidin-1-yl-ethylcarbamoyl)benzylamide], pyrimidine-4,6-dicarboxylic acid 4-(3-methoxybenzylamide) 6-(4-[3'-phenylsulfonyl]ureidobenzylamide), pyrimidine-4,6-dicarboxylic acid 4-[(2,3-dihydrobenzofuran-5-ylmethyl)amide] 6-[4-(2-morpholin-4-yl-ethylcarbamoyl)benzylamide], pyrimidine-4,6-dicarboxylic acid 4-[(2,3-dihydrobenzofuran-5-ylmethyl)amide] 6-[4-(2-pyrrolidin-1-ylethoxy)benzylamide], pyrimidine-4,6-dicarboxylic acid 4-[4-(3-cyclohexanecarbonylureido)benzylamide] 6-(3-methoxybenzylamide), pyrimidine-4,6-dicarboxylic acid 4-(3-methoxybenzylamide) 6-{4-[3-(pyridine-3-carbonyl)ureido]benzylamide}, pyrimidine-4,6-dicarboxylic acid 4-[4-(3-isobutyrylureido)benzylamide] 6-(3-methoxybenzylamide), pyrimidine-4,6-dicarboxylic acid 4-(3-methoxybenzylamide) 6-[4-(2-pyrrolidin-1-ylacetylamino)benzylamide], pyrimidine-4,6-dicarboxylic acid 4-[(4-chlorothiophen-2-ylmethyl)amide] 6-[(2,3-dihydrobenzofuran-5-ylmethyl) amide], pyrimidine-4,6-dicarboxylic acid 4-(3-methoxybenzylamide) 6-{4-[2-(2-oxopyrrolidin-1-yl)acetylamino]benzylamide}, pyrimidine-4,6-dicarboxylic acid 4-[(2,3-dihydrobenzofuran-5-ylmethyl)amide] 6-[(thiophen-3-ylmethyl)amide], pyrimidine-4,6-dicarboxylic acid 4-[(2,3-dihydrobenzofuran-5-ylmethyl)amide] 6-[(3-methylthiophen-2-ylmethyl) amide], pyrimidine-4,6-dicarboxylic acid 4-[(2,3-dihydrobenzofuran-5-ylmethyl)amide] 6-[(5-methylthiophen-2-ylmethyl) amide], pyrimidine-4,6-dicarboxylic acid 4-[4-(2-dimethylaminoacetylamino)benzylamide] 6-(3-methoxybenzylamide), pyrimidine-4,6-dicarboxylic acid 4-[(2,3-dihydrobenzofuran-5-ylmethyl)amide] 6-[4-(2-morpholin-4-ylethoxy)benzylamide], pyrimidine-4,6-dicarboxylic acid 4-[4-(3-cyclohexylureido)benzylamide] 6-(3-methoxybenzylamide), pyrimidine-4,6-dicarboxylic acid 4-{4-[3-(2,6-dichloropyridin-4-yl)ureido]benzylamide} 6-(3-methoxybenzylamide), pyrimidine-4,6-dicarboxylic acid 4-[4-(3-tert-butylureido)benzylamide] 6-(3-methoxybenzylamide),

[4-({[6-(3-methoxybenzylcarbamoyl)pyrimidine-4-carbonyl]amino}methyl)-phenyl]carboxyamino but-2-ynyl ester, pyrimidine-4,6-dicarboxylic acid 4-(4-ethanesulfonylaminobenzylamide) 6-(3-methoxy benzylamide), pyrimidine-4,6-dicarboxylic acid 4-(3-methoxybenzylamide) 6-[4-(thiophene-2-sulfonylamino)benzylamide], pyrimidine-4,6-dicarboxylic acid 4-(3-methoxybenzylamide) 6-[4-(2,2,2-trifluoroethanesulfonylamino)benzylamide],

[4-({[6-(3-methoxybenzylcarbamoyl)pyrimidin-4-carbonyl]amino}methyl)-phenyl]carboxyamino methyl ester,

[4-({[6-(3-methoxybenzylcarbamoyl)pyrimidine-4-carbonyl]amino}methyl)-phenyl]carboxyamino prop-2-ynyl ester,

[4-({[6-(3-methoxybenzylcarbamoyl)pyrimidin-4-carbonyl]amino }methyl)-phenyl]carboxyamino 2-methoxyethyl ester,

[4-({[6-(3-methoxybenzylcarbamoyl)pyrimidine-4-carbonyl]amino}methyl)-phenyl]carboxyamino 4-fluorophenyl ester, pyrimidine-4,6-dicarboxylic acid 4-[4-(3-benzoylureido)benzylamide] 6-(3-methoxy benzylamide),

[3-({[6-(3-methoxybenzylcarbamoyl)pyrimidine-4-carbonyl]amino}methyl)-phenyl]carboxyamino but-2-ynyl ester,

[3-({[6-(3-methoxybenzylcarbamoyl)pyrimidine-4-carbonyl]amino}methyl)-phenyl]carboxyamino prop-2-ynyl ester,

[3-({[6-(3-methoxybenzylcarbamoyl)pyrimidine-4-carbonyl]amino}methyl)-phenyl]carboxyamino isopropyl ester, pyrimidine-4,6dicarboxylic acid 4-(3-chloro-4-fluorobenzylamide) 6-[4-(2-pyrrolidin-1-ylethylcarbamoyl)benzylamide], pyrimidine-4,6-dicarboxylic acid 4-(3-methoxybenzylamide) 6-[4-(morpholine-4-carbonyl)benzylamide], pyrimidine-4,6-dicarboxylic acid 4-(3-methoxybenzylamide) 6-{4-[(pyridin-4-ylmethyl) carbamoyl]benzylamide}, pyrimidine-4,6-dicarboxylic acid 4-(3-chloro-4-fluorobenzylamide) 6-(4-diethyl carbamoylbenzylamide), pyrimidine-4,6-dicarboxylic acid 4-(3-chloro-4-fluorobenzylamide) 6-[4-(morpholine-4-carbonyl)benzylamide], pyrimidine-4,6-dicarboxylic acid 4-(3-chloro-4-fluorobenzylamide) 6-[4-(2-morpholin-4-ylethylcarbamoyl)benzylamide], pyrimidine-4,6-dicarboxylic acid 4-{4-[2-(2,6-dimethylpiperidin-1-yl)-2-oxoethyl] benzylamide} 6-(4-fluoro-3-methylbenzylamide), pyrimidine-4,6-dicarboxylic acid 4-(3-methoxybenzylamide) 6-[4-(1-methylpiperidin-3-yloxy)benzylamide], pyrimidine-4,6-dicarboxylic acid 4-(4-diethylcarbamoylbenzylamide) 6-(3-methoxybenzylamide), pyrimidine-4,6-dicarboxylic acid 4-[(2-chloropyridin-4-ylmethyl)amide] 6-[(2,3-dihydrobenzofuran-5-ylmethyl)amide], pyrimidine-4,6-dicarboxylic acid 4-(3-chloro-4-fluorobenzylamide) 6-(4-methanesulfonylaminobenzylamide), or pyrimidine-4,6-dicarboxylic acid 4-(4-methanesulfonylbenzylamide) 6-(3-methoxybenzylamide).

The compounds of the formula I can be prepared, for example, by reacting a compound of the formula II

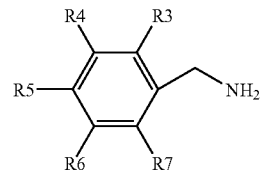
(II)

a) with a compound of the formula IIIa or IIIb

IIIa

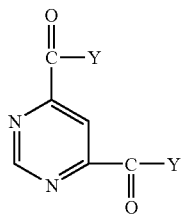
IIIb where R1, R2, R3, R4, R5, R6 and R7 have the meanings given in formula I and Y is halogen, hydroxyl or $C_1$–$C_4$-alkoxy or, together with the carbonyl group, forms an active ester or a mixed anhydride, with a compound of the formula I being formed and the reaction products being converted, where appropriate, into their physiologically tolerated salts, or b) reacting a compound of the formula II with a compound of the formula IIIa or IIIb to give a compound of the formula IVa or IVb

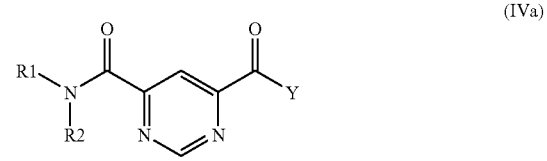
(IVa)

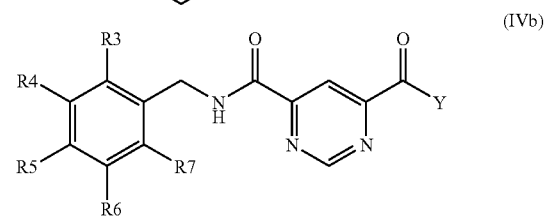
(IVb)

where R1 to R7 have the meanings given in formula I and Y is halogen, hydroxyl or $C_1$–$C_4$-alkoxy or, together with the carbonyl group, forms an active ester or a mixed anhydride, and purifying the compound of the formula IVa or IVb, where appropriate, and then converting it, with a compound of the formula IIIa or IIIb, into a compound of the formula I.

The preparation of compounds according to formula I, and the preparation of the starting substances which are required for this purpose, insofar as the substances are not commercially available, is described in more detail below.

The compounds according to the invention are most readily prepared by mixing the two components, i.e. the pyrimidine derivative according to formula (II) and the amine according to formula IIIa or IIIb, in equimolar quantities and reacting them, at temperatures of between –30° C. and 150° C., preferably at from 20° C. to 100° C., to give compound of the formula IVa or IVb and then reacting the compounds of the formula IVa or IVb, in an analogous manner, with up to an equimolar quantity of amine according to formula IIIb or IIIa. The end of the reaction can be determined, for example, by means of thin layer chromatography or HPLC-MS. A variant of this method comprises carrying out the reaction in a suitable solvent, such as diethyl ether, dimethoxyethane or tetrahydrofuran, chlorinated hydrocarbons, such as methylene chloride, chloroform, trichloroethylene or tetrachloroethylene, benzene or toluene, or else polar solvents such as dimethylformamide, acetone or dimethyl sulfoxide. In this case, the reaction temperatures are between room temperature and the boiling point of the solvent, with temperatures in the range from room temperature to 130° C. being particularly preferred.

The reaction can also take place by way of a mixed anhydride, such as ethyl chloroformate, or by way of an active ester, such as paranitrophenyl ester (Y=ClCH$_2$—COO or NO$_2$—C$_6$H$_4$—O). Appropriate methods are known and described in the literature.

A compound of the formula II or a compound of the formula IVa or IVb can also react with an amine of the formula IIIa or IIIb if Y is OH and the corresponding carboxylic acid is activated in situ using customary coupling reagents. Examples of these coupling reagents are carbodiimides, such as dicyclohexylcarbodiimide (DCC) or diisopropylcarbodiimide (DCI), or N,N'-carbonyldiazoles, such as N,N'-carbonyldiimidazole, or a uronium salt, such as O-((cyano(ethoxycarbonyl)methylene)amino)-1,1,3,3-tetramethyluronium tetrafluoroborate (TOTU) or O-(7-azabenzotriazol-1-yl)-1,1,3,3-tetramethyluronium hexafluorophosphate (HATU). Appropriate methods are known.

If amines of the formula IIIa or IIIb are not commercially available, they can be prepared from appropriate commercially available starting compounds using methods known from the literature. Examples of suitable starting compounds for amines are nitriles, nitro compounds, carboxamides, carboxylic acid esters, carboxylic acids, aldehydes and bromides. Nitriles, nitro compounds and carboxamides can be reduced to amines using known methods. Carboxylic acids and carboxylic acid esters can be converted into the carboxamides. Aldehydes can be converted directly into the amines by way of reductive amination using NH$_4$Ac/NaBH$_4$, or else initially converted into the oximes using hydroxylamine and then converted into the amines by reduction.

Where appropriate, the reaction can also take place in the presence of bases. Examples of suitable additional bases are carbonates or hydrogen carbonates, such as sodium carbonate or potassium carbonate or sodium hydrogen carbonate or potassium hydrogen carbonate, or tertiary amines, such as triethylamine, tributylamine or ethyl diisopropylamine, or heterocyclic amines, such as N-alkylmorpholine, pyridine or quinoline, or dialkylanilines.

Where appropriate, the products, in particular the compound of the formula IVa or IVb, can be worked up, for example, by extraction or chromatography, e.g. through silica gel. The isolated product can be recrystallized and, where appropriate, reacted with a suitable acid to give a physiologically tolerated salt. Examples of suitable acids are:

mineral acids, such as hydrochloric acid and hydrobromic acid and also sulfuric acid, phosphoric acid, nitric acid and perchloric acid, or organic acids, such as formic acid, acetic acid, propionic acid, succinic acid, glycolic acid, lactic acid, malic acid, tartaric acid, citric acid, maleic acid, fumaric acid, phenylacetic acid, benzoic acid, methanesulfonic acid, toluenesulfonic acid, oxalic acid, 4-aminobenzoic acid, naphthalene-1,5-disulfonic acid or ascorbic acid.

Insofar as they are not commercially available, the starting compounds of the formula IIIa or IIIb can be synthesized readily (e.g. Organikum, Organisch Chemisches Grundpraktikum [Organicum, basic practical course in organic chemistry], 15th Edition, VEB Deutscher Verlag der Wissenschaften, 1976; an overview of the different possibilities can be found on p. 822 in the methods index, the content of which is incorporated by reference).

The starting compounds of the formula (II) are obtained, for example, by using methods which are known from the literature to convert pyrimidine-4,6-dicarboxylic acid into the corresponding pyrimidine-4,6-dicarbonyl halide, preferably dicarbonyl chloride, preferably in the presence of a catalyst such as dimethylformamide. This acid halide can then, for example, be reacted either with a suitable alcohol, for example paranitrobenzyl alcohol, to give the corresponding active ester or else with lower alcohols, such as methanol or ethanol, to give the corresponding esters. The pyrimidine-4,6-dicarboxylic acid can also initially be converted, in the added presence of a suitable carboxylic acid or of a carboxylic acid ester such as ethyl chloroformate, into a mixed anhydride, which is then reacted with the amines of the compound of the formulae IIIa or IIIb and IVa or IVb to give the products according to the invention. An appropriate method is likewise described in the literature.

The pyrimidine-4,6-dicarboxylic acid is prepared using methods known from the literature, for example by oxidizing 4,6-dimethylpyrimidine which, for its part, can be obtained, for example, by the catalytic hydrogenation of commercially available 2-mercapto-4,6-dimethylpyrimidine.

Insofar as compounds of the formula I permit diastereoisomeric or enantiomeric forms and accrue as their mixtures in the synthesis which is selected, separation into the pure stereoisomers is achieved either by chromatography on an optionally chiral support material or, provided the racemic compound of the formula I is capable of salt formation, by fractionally crystallizing the diastereomeric salts which are formed using an optically active base or acid as auxiliary substance. Examples of suitable chiral stationary phases for the thin-layer or column chromatographic separation of enantiomers are modified silica gel supports (what are termed Pirkle phases) and also high molecular weight carbohydrates, such as triacetyl cellulose. Following appropriate derivatization, which is known to the skilled person, gas-chromatographic methods on chiral stationary phases can also be used for analytical purposes. In order to separate the enantiomers of the racemic carboxylic acids, the diastereomeric salts, which differ in solubility, are formed using an optically active, as a rule commercially available, base such as (−)-nicotine, (+)- and (−)-phenylethylamine, quinine bases, L-lysine or L- and D-arginine, the more sparingly soluble component is isolated as a solid, the more readily soluble diastereomer is separated out from the mother liquor, and the pure enantiomers are isolated from the diastereomer salts which have been obtained in this way. The racemic compounds of the formula I which contain a basic group, such as amino group, can, in what is in principle the same manner, be converted into the pure enantiomers using optically active acids, such as (+)-camphor-10-sulfonic acid, D- and L-tartaric acid, D- and L-lactic acid and (+) and (−)-mandelic acid. Chiral compounds which contain alcohol or amine functions can also be converted into the corresponding esters or amides using appropriately activated or optionally N-protected enantiomerically pure amino acids or, conversely, chiral carboxylic acids can be converted into the amides using carboxyl-protected enatiomerically pure amino acids or into the corresponding chiral esters using enantiomerically pure hydroxyl carboxylic acids such as lactic acid. The chirality of the amino acid or alcohol radical which has been introduced in enantiomerically pure form can then be used for separating the isomers by the diastereomers, which are now present, being separated by means of crystallization or chromatography on suitable stationary phases and, after that, using suitable methods to once again eliminate the entrained chiral molecule moiety.

Acidic or basic products of the compound of the formula I may be present in the form of their salts or in free form. Preference is given to pharmacologically tolerated salts, e.g. alkali metal salts or alkaline earth metal salts or hydrochlorides, hydrobromides, sulfates, hemisulfates, all possible phosphates and also salts of the amino acids, natural bases or carboxylic acids.

Physiologically tolerated salts are prepared in a manner known per se from compounds of the formula I, including their stereoisomeric forms, which are capable of salt formation. The carboxylic acids form stable alkali metal salts, alkaline earth metal salts or optionally substituted ammonium salts with basic reagents such as hydroxides, carbonates, hydrogen carbonates, alkoxides and ammonia or organic bases, for example trimethylamine, triethylamine, ethanolamine or triethanolamine, or else basic amino acids, for example lysine, ornithine or arginine. Insofar as the compounds of the formula I possess basic groups, stable acid addition salts can also be prepared using strong acids. Both inorganic and organic acids, such as hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, acetic acid, oxalic acid, tartaric acid, succinic acid and trifluoroacetic acid are suitable for this purpose.

The invention also relates to a process for producing a pharmaceutical, wherein at least one compound of the formula I is brought, together with a pharmaceutically suitable and physiologically tolerated carrier and, where appropriate, other suitable active compounds, additives or auxiliary substances, into a suitable form for administration.

The compounds of the formula I are mixed with the additives, such as carrier substances, stabilizers or inert diluents, which are suitable for the purpose and brought into suitable administration forms, such as tablets, sugar-coated tablets, hard gelatine capsules, aqueous, alcoholic or oily suspensions or aqueous or oily solutions, using the customary methods. The examples of inert carrier substances which can be used are gum Arabic, magnesium oxide, magnesium carbonate, potassium phosphate, lactose, glucose or starch, in particular corn starch. In this connection, the preparation can be effected either as dry granules or as wet granules. The examples of suitable oily carrier substances or solvents are vegetable or animal oils, such as sunflower oil or cod liver oil.

For subcutaneous, intraarticular, intraperitoneal or intravenous administration, the active compounds are, if desired, brought into solution, suspension or emulsion using the substances which are suitable for this purpose, such as solubilizers, emulsifiers or other auxiliary substances. Examples of suitable solvents are physiological sodium chloride solution or alcohols, e.g. ethanol, propanol or glycerol, and, in addition, sugar solutions, such as solutions of glucose or mannitol, or else a mixture which is composed of the different solvents mentioned.

Customary adjuvants, such as carrier substances, disintegrants, binding agents, coating agents, swelling agents, glidants or lubricants, flavorings, sweeteners and solubilizers are also used. Auxiliary substances which are frequently employed and which may be mentioned are magnesium carbonate, titanium dioxide, lactose, mannitol and other sugars, talc, milk protein, gelatine, starch, cellulose and its derivatives, animal and vegetable oils, such as cod liver oil, sunflower oil, peanut oil or sesame seed oil, polyethylene glycol and solvents such as sterile water and monohydric or polyhydric alcohols, such as glycerol.

The compounds of the formula I are preferably prepared as pharmaceutical preparations and administered in dosage units, with each unit containing a defined dose of the compound of the formula I as the active constituent. For this purpose, the compounds of the formula I can be administered orally in doses of from 0.01 mg/kg/day to 25.0 mg/kg/day, preferably from 0.01 mg/kg/day to 5.0 mg/kg/day, or parenterally in doses of from 0.001 mg/kg/day to 5 mg/kg/day, preferably of from 0.001 mg/kg/day to 2.5 mg/kg/day. The dosage can also be increased in severe cases. However, smaller doses are also adequate in many cases. These figures relate to the treatment of an adult.

Embodiments

As a result of their pharmacological properties, the compounds of the formula I are suitable for the prophylaxis and therapy of all those diseases in whose course an increase in the activity of matrix metalloproteinase 13 is involved.

These diseases include degenerative joint diseases, such as osteoarthroses, spondyloses or cartilage loss following joint trauma or a relatively long period of joint immobilization following meniscus injuries or patella injuries or ligament rupture. They also include diseases of the connective tissue such as collagenoses, periodontal diseases, wound healing disturbances and chronic diseases of the locomotory apparatus, such as inflammatory, immunologically determined or metabolism-determined, acute and chronic arthritides, arthropathies, myalgias and disturbances of bone metabolism or cancer diseases such as breast cancer.

The pharmaceuticals according to the invention can be administered by subcutaneous, intraarticular, intraperitoneal or intravenous injection. Intraarticular injection is preferred. Rectal, oral, inhalative or transdermal administration is also possible.

The invention is explained in more detail below with the aid of examples.

EXAMPLES

Example 1

Ethyl [4-({[6-(4-fluoro-3-methylbenzylcarbamoyl)pyrimidine-4-carbonyl]-amino}methyl)phenyl]acetate

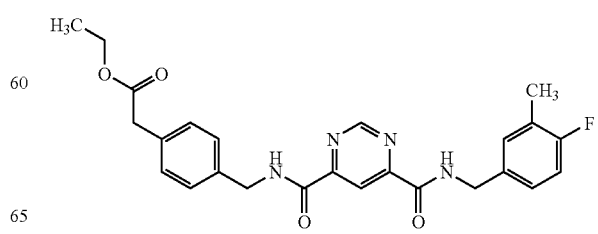

a) Methyl 6-(4-fluoro-3-methylbenzylcarbamoyl)pyrimdine-4-carboxylate 8.81 g (0.045 mol) of dimethyl pyrimidine-4,6-dicarboxylate were dissolved in 200 ml of DMF, after which 6.25 g (0.045 mol) of 4-fluoro-3-methylbenzylamine were added and the mixture was stirred at 60° C. for 48 hours (h). The solvent was removed in vacuo and the residue was taken up in ethyl acetate. The organic phase was washed with a saturated solution of sodium hydrogen carbonate and 0.5 N HCl and then dried (MgSO4). After filtering, and evaporating the solvent in vacuo, the residue was stirred up in isopropanol. This resulted in 8.75 g of product, which was subjected to further reaction without any further purification.

b) 6-(4-Fluoro-3-methylbenzylcarbamoyl)pyrimdine-4-carboxylic acid 8.75 g (0.02 mol) of methyl 6-(4-fluoro-3-methylbenzylcarbamoyl)pyrimidine-4-carboxylate (70%) were taken up in 150 ml of ethanol, after which 1.89 g (0.022 mol) ofNaOH in 6 ml of water were added. After 3 hours (h) at room temperature, the solvent was removed under reduced pressure and water was added to the residue; the solution was then brought to pH <2 with conc. HCl. The precipitate was filtered off with suction and dried. This resulted in 5.5 g (94%) of 6-(4-fluoro-3-methylbenzylcarbamoyl)pyrimidine-4-carboxylic acid. MS (ES$^+$): m/e=289.09.

c) Ethyl (4-aminomethylphenyl)acetate 0.5 g (2.6 mmol) of ethyl (4-cyanophenyl)acetate was dissolved in 70 ml of ethanolic ammonia solution and hydrogenated, at room temperature and under standard pressure, over Raney nickel. After 45 minutes, the mixture was filtered and evaporated. This resulted in 0.42 g (82%) of ethyl (4-aminomethylphenyl)acetate. MS (ES$^+$): m/e=194.11 d) Ethyl [4-({[6-(4-fluoro-3-methylbenzylcarbamoyl)pyrimidine-4-carbonyl]amino}methyl)phenyl]acetate 1.3 g (4.5 mmol) of 6-(4-fluoro-3-methylbenzylcarbamoyl)pyrimidine-4-carboxylic acid and 1.042 g (5.4 mmol) of ethyl (4-aminomethylphenyl)acetate were dissolved in 30 ml of DMF, after which 1.02 g (4.9 mmol) of dicyclohexylcarbodiimide and 0.607 g (4.5 mmol) of hydroxybenzotriazole were added at 5° C. The mixture was stirred for 5 hours (h) and filtered with suction. The solvent was removed in vacuo and the residue was taken up in ethyl acetate; this solution was washed with a saturated aqueous solution of NaHCO3. The organic phase was dried (MgSO4), filtered and evaporated under reduced pressure. This resulted in 2.66 g of product, which was further purified by means of preparative HPLC. MS (ES$^+$): m/e=464.19.

Example 2

[4-({[6-(4-Fluoro-3-methylbenzylcarbamoyl)pyrimidine-4-carbonyl]amino}-methyl)phenyl]acetic acid

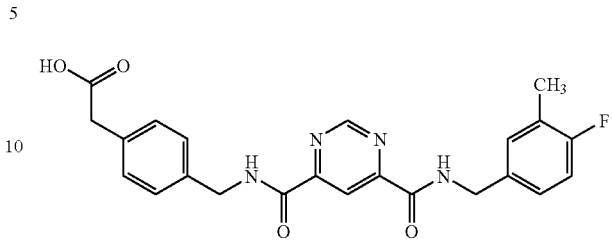

2.4 g (5.2 mmol) of ethyl [4-({[6-(4-fluoro-3-methylbenzylcarbamoyl)pyrimidine-4-carbonyl]amino}methyl)phenyl] acetate were taken up in 150 ml of water, after which 10 ml of water and 0.227 g (5.7 mmol) of NaOH were added. After 5 days of stirring at room temperature, the solvent was removed under reduced pressure and the residue was stirred up with ethanol and filtered off. This resulted in 1.51 g (67%) of [4-({[6-(4-fluoro-3-methylbenzylcarbamoyl)pyrimidine-4-carbonyl]amino}methyl)phenyl]acetic acid. MS (ES$^+$): m/e=436.15.

Example 3

Pyrimidine-4,6-dicarboxylic acid
4-(4-diethylcarbamoylbenzylamide)
6-(3-methoxybenzylamide)

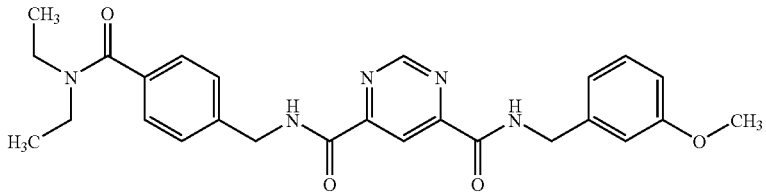

a) Synthesizing 6-(3-methoxybenzylcarbamoyl)pyrimdine-4-carboxylic acid 26 g (88 mmol) of methyl 6-(3-methoxybenzylcarbamoyl)pyrimidine-4-carboxylate (prepared by reacting dimethyl pyrimidine-4,6-dicarboxylate with 3-methoxybenzylamine) were dissolved in 100 ml of tetrahydrofuran, after which 104 ml (1.2 equivalents) of a 1 molar aqueous solution of lithium hydroxide were added and the reaction mixture was then stirred at room temperature for 18 hours.

The majority of the solvent employed was then distilled off under reduced pressure and insoluble by-products were filtered off from the residue; the filtrate was then acidified with a 20% aqueous solution of citric acid. In connection with this, 6-(3-methoxybenzylcarbamoyl)pyrimidine-4-carboxylic acid crystallized out in the form of pale yellow crystals, which were filtered off.

This resulted in 19 g (66.2 mmol) of 6-(3-methoxybenzylcarbamoyl)pyrimidine-4-carboxylic acid (yield 75% of theory; MS (ES$^+$): m/e=287.8).

b) Methyl 4-({[6-(3-methoxybenzylcarbamoyl)pyrimdine-4-carbonyl]amino}methyl)benzoate 4.3 g of 6-(3-methoxybenzylcarbamoyl)pyrimidine-4-carboxylic acid (15 mmol) from a) were dissolved in 50 ml of absolute N,N-dimethylformamide, after which 3.3 g (16.5 mmol) of methyl 4-(aminomethyl)benzoate hydrochloride, 5.4 g (16.5 mmol) of O-[(cyanoethoxycarbonylmethylene)amino]-N,N,N',N'-tetramethyluronium tetrafluoroborate (TOTU) and 4.6 ml of triethylamine (33 mmol) were added consecutively, at 0° C. and while stirring. The reaction mixture was stirred at 0° C. for 1 hour and then stirred at room temperature for 12 hours.

For the working up, the solvent was distilled off under reduced pressure and the residue was taken up in 100 ml of dichloromethane. The organic phase was washed with 100 ml of a saturated aqueous solution of sodium hydrogen carbonate and then washed three times with in each case 100 ml of water. After the organic phase had been dried with Na$_2$SO$_4$, the solvent was distilled off under reduced pressure. The oily residue was triturated with a little diethyl ether, during which colorless crystals crystallized out. After the reaction product had been filtered off and washed with n-pentane, 6.6 g of methyl 4-({[6-(3-methoxybenzylcarbamoyl)pyrimidine-4-carbonyl]amino}methyl)benzoate (pale yellow crystals) were obtained. According to LC-MS analysis, the purity of the reaction product is 88% (MS (ES$^+$): m/e=435.2).

c) 4-({[6-(3-Methoxybenzylcarbamoyl)pyrimidine-4-carbonyl]amino}-methyl)benzoic acid 6.6 g of the methyl ester prepared in b) were dissolved in 100 ml of tetrahydrofuran, after which 36 ml (2.4 equivalents) of a 1 molar solution of lithium hydroxide were added and the reaction mixture was then stirred for 4 hours while refluxing the solvent.

After that, the solvent was distilled off under reduced pressure. After 50 ml of water had been added, the mixture was filtered through Celite® filter aid and the filtrate was acidified with 2 n aqueous hydrochloric acid. The reaction product precipitated out on acidification and was filtered off.

This resulted in 3.05 g of 4-({[6-(3-methoxybenzylcarbamoyl)pyrimidine-4-carbonyl]amino}methyl)benzoic acid, pale yellow crystals [yield 48% of theory; MS (ES$^+$): m/e=421.31].

d) Pyrimidine-4,6-dicarboxylic acid 4-(4-diethylcarbamoylbenzylamide) 6-(3-methoxybenzylamide)

420 mg of 4-({[6-(3-methoxybenzylcarbamoyl)pyrimidine-4-carbonyl]amino}methyl)benzoic acid from c) were dissolved in 5 ml of absolute N,N-dimethylformamide, after which 115 µl of diethylamine, 361 mg of O-[(cyanoethoxycarbonylmethylene)amino]-N,N,N',N'-tetramethyluronium tetrafluoroborate (TOTU) and 153 µl of triethylamine were added consecutively, at 0° C. and while stirring, and the reaction mixture was stirred at 0° C. for 1 hour and then at room temperature for 12 hours.

For the working up, the solvent was distilled off under reduced pressure and the residue was taken up in 100 ml of dichloromethane. The organic phase was washed with 30 ml of a saturated aqueous solution of sodium hydrogen carbonate and then washed three times with in each case 30 ml of water. After the organic phase had been dried with Na$_2$SO$_4$, the solvent was distilled-off under reduced pressure. The oily residue was purified by column chromatography on silica gel (40–63µ) using ethyl acetate/n-heptane, mixing ratio 2:1, as the mobile phase. After the solvent had been distilled off, an oily residue was obtained, with this residue slowly crystallizing after a little diethyl ether had been added.

This resulted in 270 mg of pyrimidine-4,6-dicarboxylic acid 4-(4-diethylcarbamoylbenzylamide) 6-(3-methoxybenzylamide), colorless crystals (yield 57% of theory [MS (ES$^+$): m/e=476.40]).

Example 4

Pyrimidine-4,6-dicarboxylic acid4-[(2,3-dihydrobenzofuran-5-ylmethyl)amide] 6-[(pyridin-4-ylmethyl)amide]

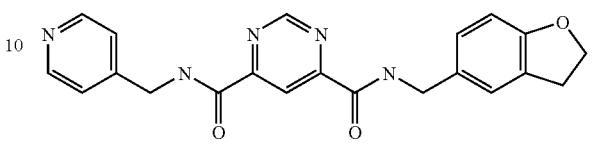

a) Synthesizing 6-[(pyridin-4-ylmethyl)carbamoyl]pyrimidine-4-carboxylic acid 9.7 g (35.7 mmol) of methyl 6-[(pyridin-4-ylmethyl)carbamoyl]pyrimidine-4-carboxylate (prepared by reacting dimethyl pyrimidine-4,6-dicarboxylate with pyridin-4-ylmethylamine) were dissolved in 80 ml of tetrahydrofuran and 40 ml of water, after which 40 ml of a 1 molar aqueous solution of NaOH were added and the reaction mixture was subsequently stirred at room temperature for 2 hours.

For the working-up, the reaction mixture was concentrated down, on a rotary evaporator and under reduced pressure, to half the original volume. The residue was then acidified with 22 ml of an aqueous 2 N solution of hydrochloric acid and the reaction mixture was concentrated down to dryness on the rotary evaporator.

This resulted in 12.2 g of a colorless solid product, which was further reacted directly as described in 4 b).

b) Pyrimidin-4,6-dicarboxylic acid 4-[(2,3-dihydrobenzofuran-5-ylmethyl)amide]6-[(pyridin-4-ylmethyl)amide]

12.2 g of the compound prepared under 4a) were dissolved in 150 ml of absolute DMF, after which 6.63 g (35.7 mmol) of 5-aminomethyl-2,3-dihydrobenzofuran hydrochloride, 11.7 g (35.7 mmol) of O-[(cyanoethoxycarbonylmethylene)amino]-N,N,N',N'-tetramethyluronium tetrafluoroborate (TOTU) and 20 ml of triethylamine were added consecutively while the mixture was being stirred at 0° C.; After the addition had been completed, the reaction mixture was stirred at 0° C. for 1 hour and at room temperature for 4 hours.

For the working-up, the solvent was distilled off under reduced pressure and the residue was taken up in 200 ml of dichloromethane. The organic phase was then washed twice with a saturated aqueous solution of sodium hydrogen carbonate and once with water and then dried with sodium sulfate; the solvent was then removed under reduced pressure on a rotary evaporator. The reaction product, which accrued as an oily residue, crystallized out in the form of pink crystals after a little diethyl ether had been added. In order to purify it further, it was recrystallized twice from in each case 200 ml of isopropanol.

This resulted in 10 g (25.6 mmol) of pyrimidine-4,6-dicarboxylic acid 4-[(2,3-dihydrobenzofuran-5-ylmethyl)amide] 6-[(pyridin-4-ylmethyl)amide] (yield 72% of theory, based on both reaction steps; MS (ES$^+$): 390.08)

$^1$H-NMR (400 MHz, d$_6$-DMSO): δ=3.13 (t, J=8.6 Hz, 2H), 4.42 (d, J=6.4 Hz, 2H), 4.48 (t, J=8.6 Hz, 2 H), 4.54 (d, J=6.4 Hz, 2 H), 6.69 (d, J=8 Hz, 1 H), 7.07 (m, 1 H), 7.22 (m, 1 H), 7.31 (m, 2 H), 8.46 (m, 1 H), 8.50 (m 2 H), 9.47 (m, 1 H), 9.58 (t, J=6.4 Hz, 1 H), 9.80 (t, J=6.4 Hz, 1 H).

Example 5

Pyrimidine-4,6-dicarboxylic acid 4-[(2,3-dihydrobenzofuran-5-ylmethyl)amide]6-[4-(morpholine-4-carbonyl)benzylamide]

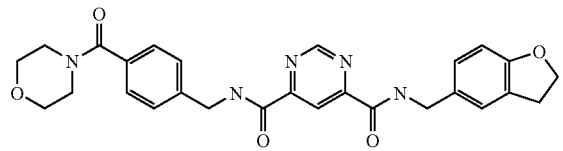

a) Synthesizing 6-[(2,3-dihydrobenzofuran-5-ylmethyl)carbamoyl]pyrimidine-4-carboxylic acid 16.1 g (51 mmol) of methyl 6-[(2,3-dihydrobenzofuran-5-ylmethyl)carbamoyl]pyrimidine-4-carboxylate (prepared by reacting dimethyl pyrimidin-4,6-dicarboxylate with 5-aminomethyl-2,3-dihydrobenzofuran) were dissolved in 150 ml of tetrahydrofuran, after which 62 ml of a 1 molar aqueous solution of LiOH were added and the reaction mixture was then stirred at room temperature for 2 hours.

For the working-up, the reaction mixture was concentrated under reduced pressure on a rotary evaporator. The crude product was then taken up in 100 ml of water and, after active charcoal had been added, this solution was filtered through a Celite® clarifying layer. The resulting mother liquor was then acidified by adding a 2 N solution of aqueous HCl, in connection with which the reaction product slowly precipitated out in the form of colorless crystals.

After the reaction product had been filtered off and dried, 8.3 g (27 mmol) of a colorless solid product were obtained, with this product then being further reacted directly to give 5b; yield 53% of theory. MS (ES$^+$): 300.1.

b) Synthesizing methyl 4-[({6-[(2,3-dihydrobenzofuran-5-ylmethyl)carbamoyl]-pyrimidine-4-carbonyl}amino)methyl]benzoate 4.7 g (15.7 mmol) of the compound prepared under a) were dissolved in 30 ml of absolute DMF, after which 3.5 g (17.3 mmol) of methyl 4-aminomethylbenzoate, 5.7 g (17.3 mmol) of O-[(cyanoethoxycarbonylmethylene)amino]-N,N,N',N'-tetramethyluronium tetrafluoroborate (TOTU) and 4.8 ml of triethylamine were added consecutively while the mixture was being stirred at 0° C. After the addition had been completed, the reaction mixture was stirred at 0° C. for 1 hour and at room temperature for 8 hours.

For the working-up, the solvent was distilled off under reduced pressure and the residue was taken up in 100 ml of dichloromethane. The organic phase was then washed twice with a saturated aqueous solution of sodium hydrogen carbonate and once with water and then dried with sodium sulfate; the solvent was then removed under reduced pressure on a rotary evaporator. The reaction product, which accrued as an oily residue, crystallized in the form of pale yellow crystals after a little diethyl ether had been added.

This resulted in 6.8 (15.2 mmol) of methyl 4-[({6-[(2,3-dihydrobenzofuran-5-ylmethyl)carbamoyl]pyrimidine-4-carbonyl}amino)methyl]benzoate, yield 97% of theory. MS (ES$^+$): 447.1.

c) 4-[({6-[(2,3-dihydrobenzofuran-5-ylmethyl)carbamoyl]pyrimidine-4-carbonyl}amino) methyl]benzoic acid 6.28 g (14 mmol) of methyl 4-[({6-[(2,3-dihydrobenzofuran-5-ylmethyl)-carbamoyl]pyrimidine-4-carbonyl}amino)methyl]benzoate (see 5b) were suspended in 150 ml of tetrahydrofuran and 70 ml of water, after which 16.9 ml of a 1N aqueous solution of NaOH were added and the reaction mixture was then stirred at room temperature for 24 hours.

For the working-up, the reaction mixture was concentrated down, on a rotary evaporator and under reduced pressure, to a volume of approx. 50 ml, after which 100 ml of ice water were added. The mixture was then acidified with a 2N aqueous solution of HCl, in connection with which the reaction product precipitated out in the form of pale yellow crystals.

After the reaction product had been filtered off, washed with a little water and dried, 5.4 g (12.5 mmol) of a colorless solid product were obtained, with this product being further reacted directly to give 5d; yield: 89% of theory. MS (ES$^+$): 433.2.

$^1$H-NMR (400 MHz, d$_6$-DMSO): δ=3.13 (t, J=8.7 Hz, 2 H), 4.43 (d, J=6.1 Hz, 2 H), 4.48 (t, J=8.7 Hz, 2 H), 4.59 (d, J=6.3 Hz, 2 H), 6.69 (d, J=8.1 Hz, 1 H), 7.07 (m, 1 H), 7.22 (m, 1 H), 7.44 (m, 2 H), 7.88 (m, 1 H), 7.90 (m, 1 H), 8.47 (d, J=1.5 Hz, 1 H), 9.46 (d, J=1.3 Hz, 1 H), 9.56 (t, J=6.3 Hz, 1 H), 9.76 (t, J=6.3 Hz, 1 H), 12.90 (br s, 1H).

d) Pyrimidine-4,6-dicarboxylic acid 4-[(2,3-dihydrobenzofuran-5-ylmethyl)amide]6-[4-(morpholine-4-carbonyl)benzylamide]

432 mg (1 mmol) of the compound prepared under c) were dissolved in 5 ml of absolute DMF after which 96 µl (1.1 mmol) of morpholine, 361 mg (1.1 mmol) of O-[(cyanoethoxycarbonylmethylene)amino]-N,N,N',N'-tetramethyluronium tetrafluoroborate (TOTU) and 155 µl of triethylamine were added consecutively while the mixture was being stirred at 0° C. After the addition had been completed, the reaction mixture was stirred at 0° C. for 1 hour and at room temperature for 8 hours.

For the working-up, the solvent was distilled off under reduced pressure and the residue was taken up in 30 ml of dichloromethane. The organic phase was then washed twice with a saturated aqueous solution of sodium hydrogen carbonate and once with water and dried with sodium sulfate; the solvent was then removed under reduced pressure on a rotary evaporator. The crude product, which accrued as an oily residue, was purified by means of chromatography on silica gel (40–63 µ; mobile phase: ethyl acetate/methanol=20/1). After the mobile phase had been removed by distilling under reduced pressure, an oily reaction product was obtained, with this reaction product crystallizing out in the form of colorless crystals after diethyl ether had been added. 340 mg (068 mmol) of colorless crystals were obtained, yield 68% of theory. MS (ES$^+$): 502.27.

$^1$H-NMR (500 MHz, d$_6$-DMSO): δ=2.60 (m, 2 H), 3.4–3.6 (br m, 8 H), 4.42 (d, J=6.5 Hz, 2 H), 4.48 (t, J=8.6 Hz, 2 H), 4.56 (d, J=6.5 Hz, 2 H), 6.68 (d, J=8.3 Hz 1 H), 7.07 (d, J=6.5 Hz, 1 H), 7.22 (s, 1 H), 7.88 (m, 4 H), 8.46 (m, 1 H), 9.46 (m, 1 H), 9.57 (t, J=6.5 Hz, 1 H), 9.75 (t, J=6.5 Hz, 1 H).

The following Examples 6–161 were prepared in a comparable manner to at least one of the procedures detailed in Examples 1–5 above.

TABLE 1

| Example | Structure | MS (ESI+) |
|---|---|---|
| 6 | 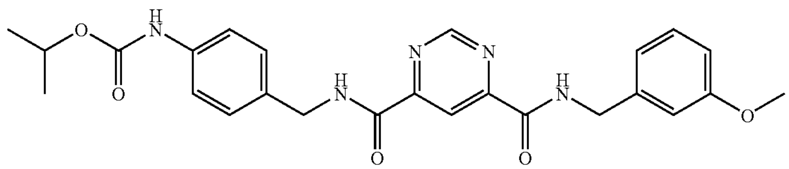 | 478.34 |
| 7 | 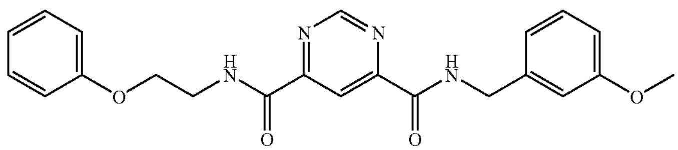 | 407.36 |
| 8 | 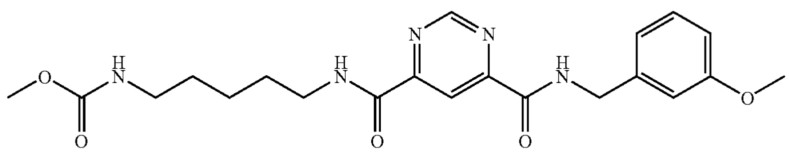 | 430.2 |
| 9 | 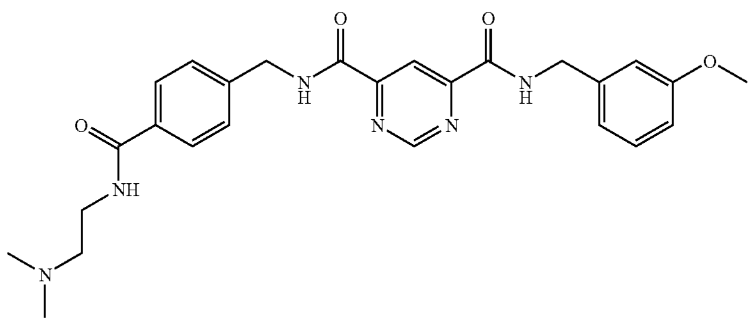 | 491.38 |
| 10 | 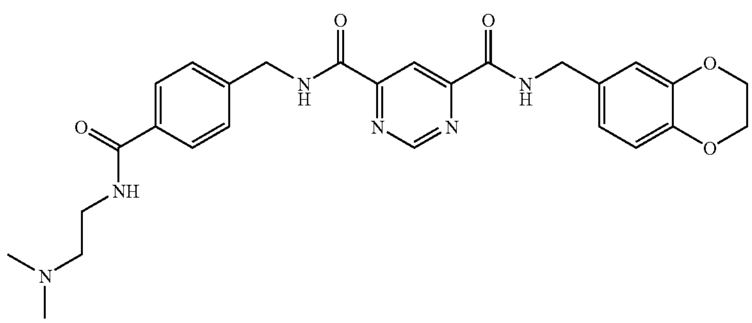 | 519.36 |
| 11 | 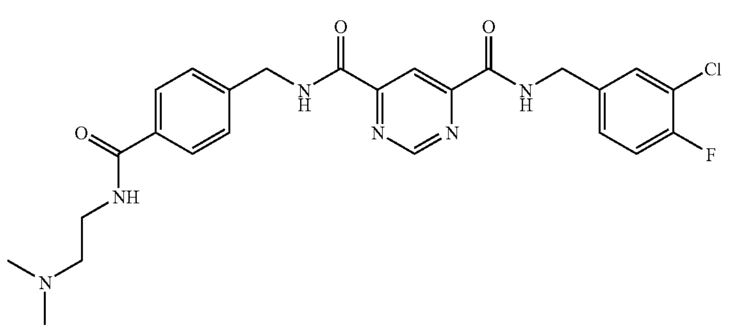 | 513.31 |

TABLE 1-continued

| Example | Structure | MS (ESI+) |
|---|---|---|
| 12 | 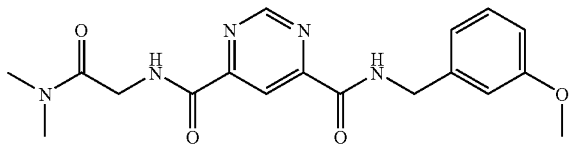 | 372.19 |
| 13 | 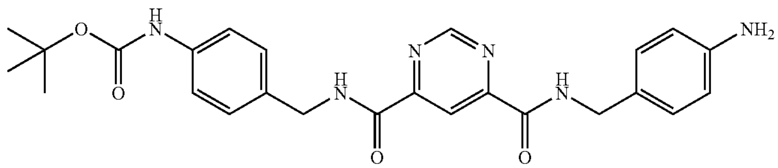 | 477.41 |
| 14 | 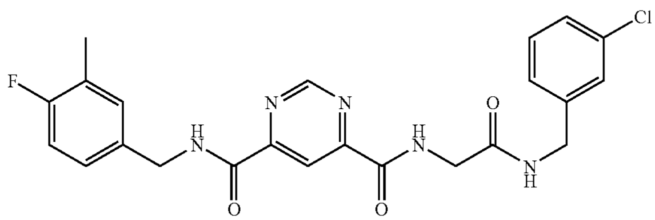 | 470.20 |
| 15 | 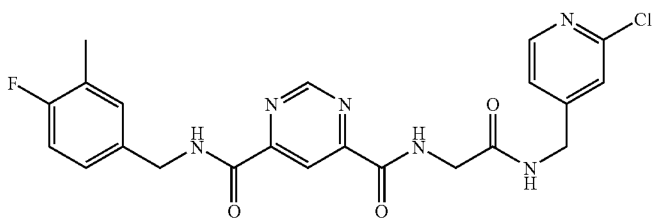 | 471.29 |
| 16 | 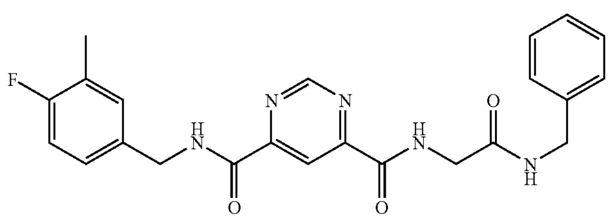 | 436.22 |
| 17 | 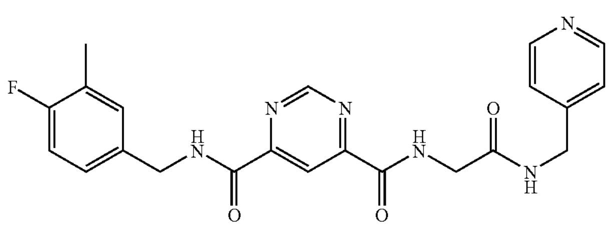 | 437.17 |
| 18 | 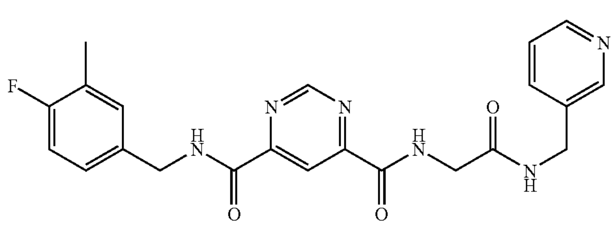 | 437.17 |

TABLE 1-continued

| Example | Structure | MS (ESI+) |
|---|---|---|
| 19 | 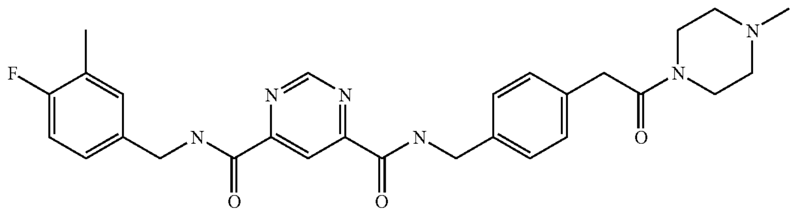 | 519.48 |
| 20 | 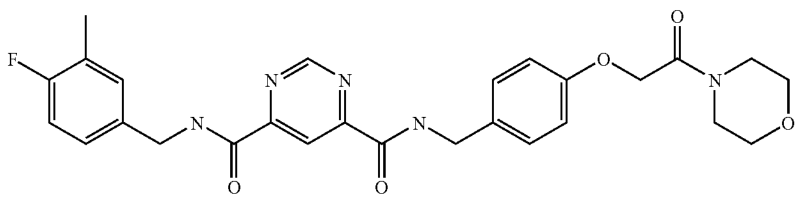 | 522.41 |
| 21 | 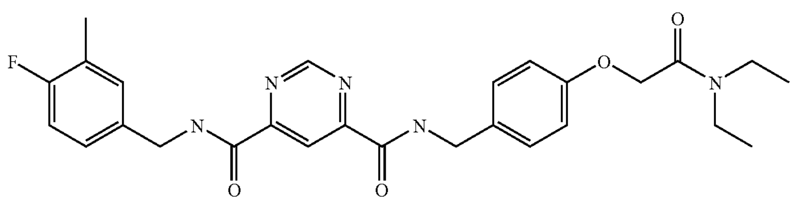 | 508.44 |
| 22 | 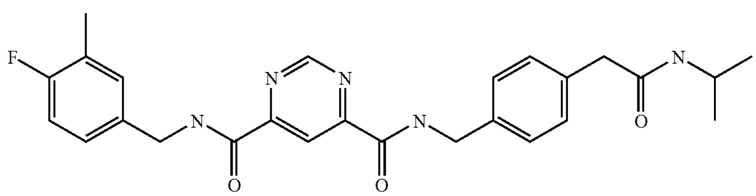 | 478.44 |
| 23 | 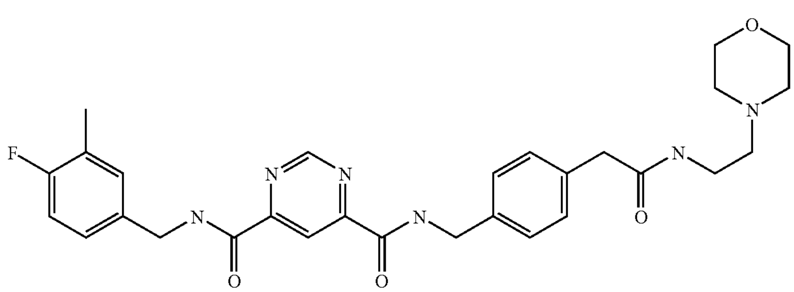 | 549.50 |
| 24 | 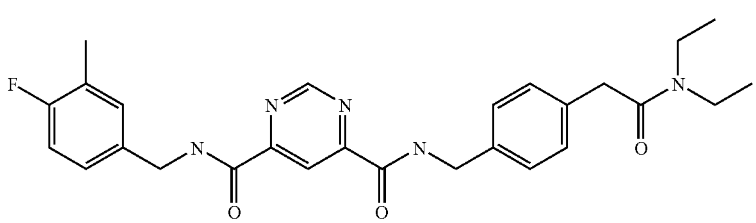 | 492.45 |
| 25 | 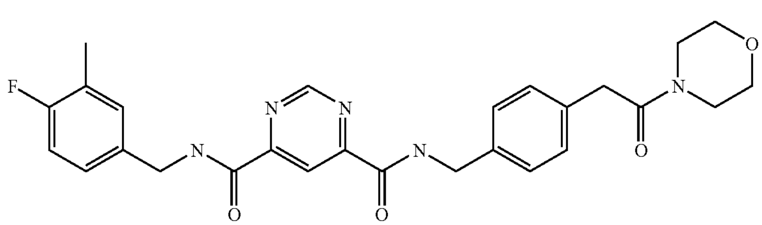 | 506.45 |

TABLE 1-continued

| Example | Structure | MS (ESI+) |
|---|---|---|
| 26 | 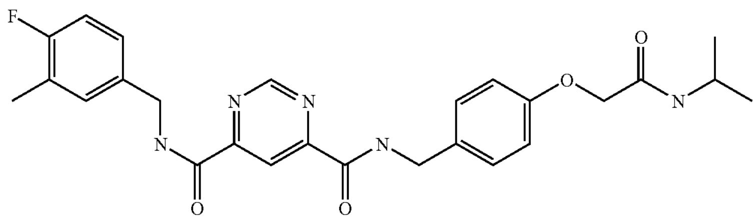 | 494.32 |
| 27 | 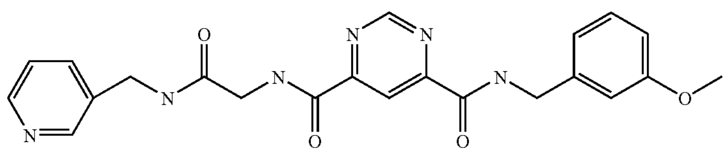 | 435.38 |
| 28 | 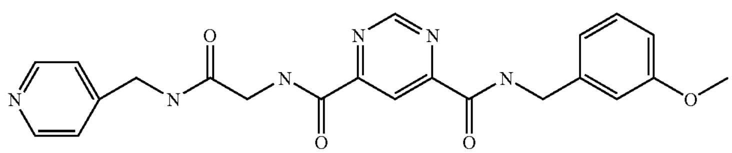 | 435.38 |
| 29 | 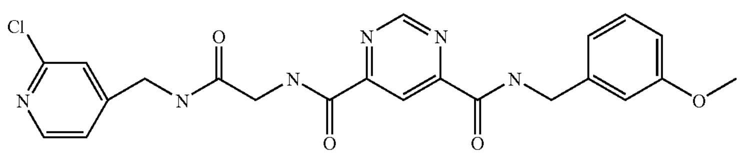 | 469.37 |
| 30 | 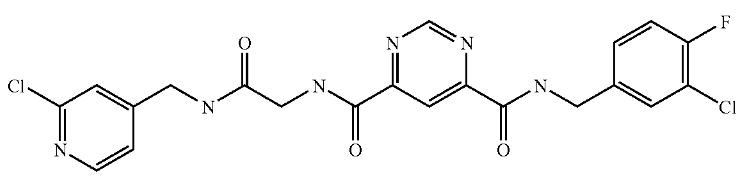 | 491.31 |
| 31 | 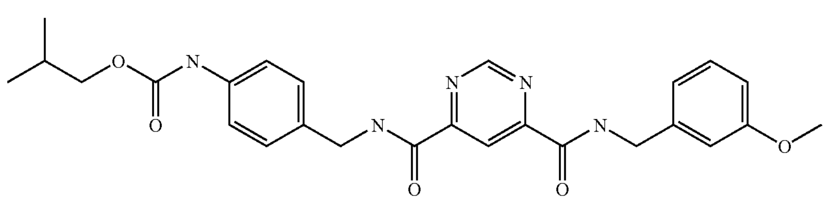 | 492.26 |
| 32 | 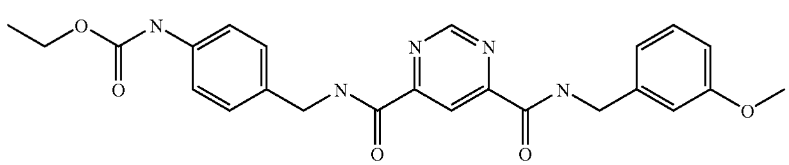 | 464.20 |
| 33 | 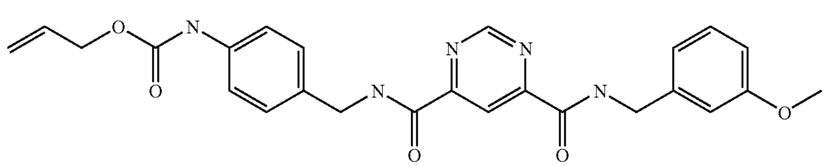 | 476.23 |

TABLE 1-continued

| Example | Structure | MS (ESI+) |
|---------|-----------|-----------|
| 34 | 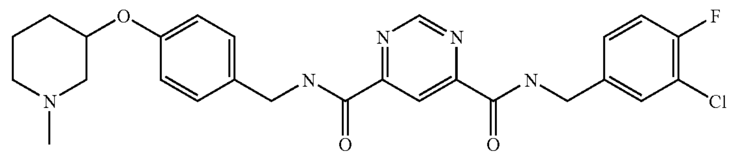 | 512.38 |
| 35 | 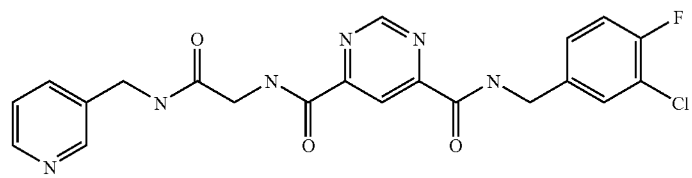 | 457.29 |
| 36 | 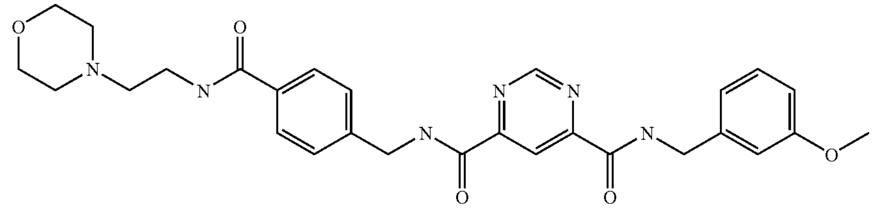 | 533.30 |
| 37 | 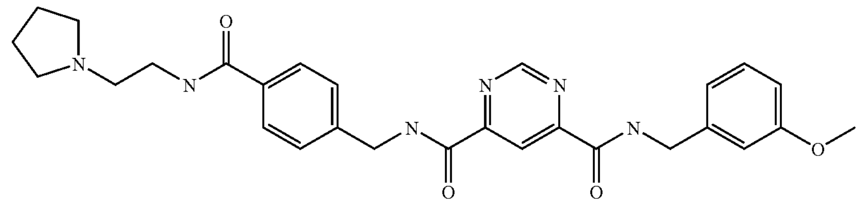 | 517.27 |
| 38 | 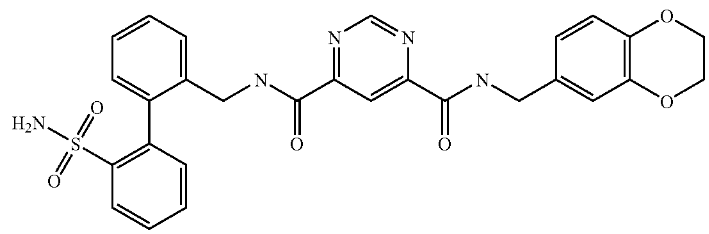 | 560.20 |
| 39 | 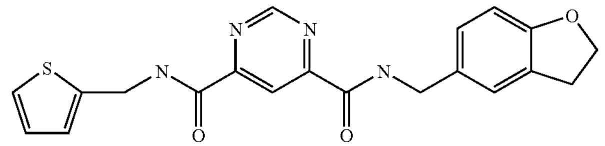 | 395.30 |
| 40 | 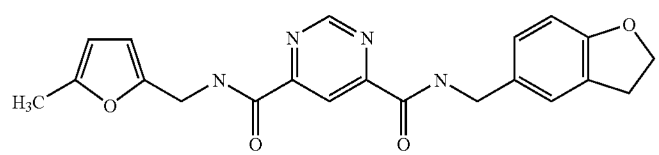 | 393.27 |

TABLE 1-continued

| Example | Structure | MS (ESI+) |
|---|---|---|
| 41 | 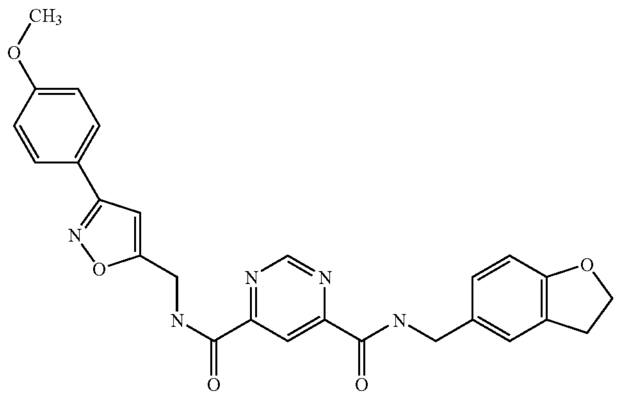 | 486.15 |
| 42 | 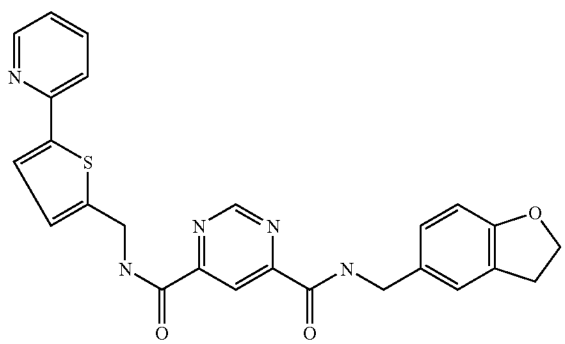 | 472.12 |
| 43 | 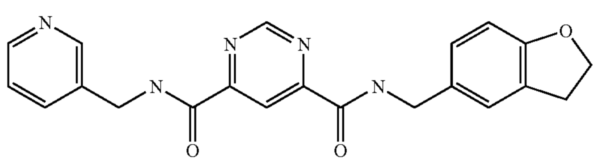 | 390.38 |
| 44 | 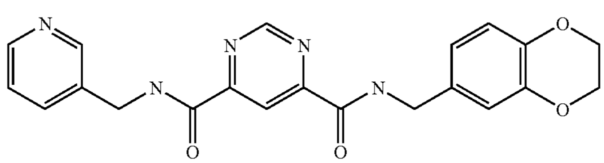 | 406.16 |
| 45 | 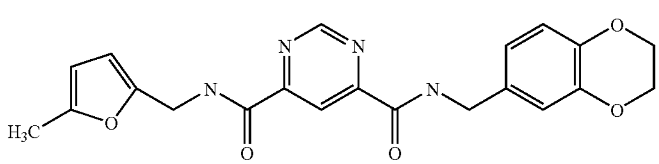 | 409.16 |
| 46 | 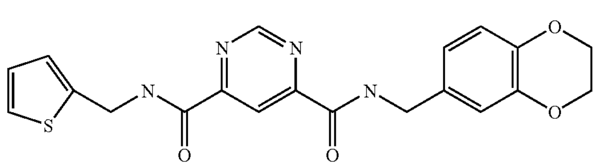 | 411.17 |

TABLE 1-continued

| Example | Structure | MS (ESI+) |
|---|---|---|
| 47 | 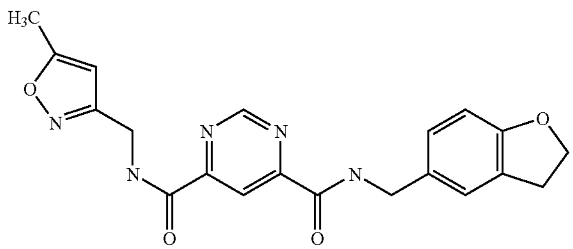 | 394.04 |
| 48 | 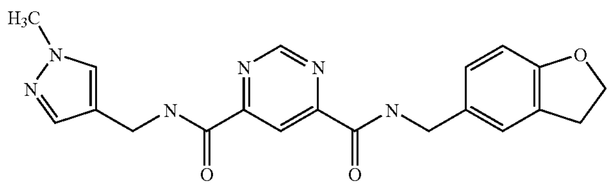 | 393.28 |
| 49 | 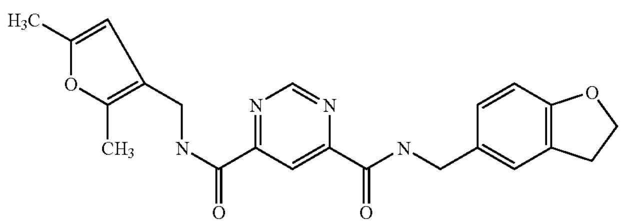 | 407.10 |
| 50 | 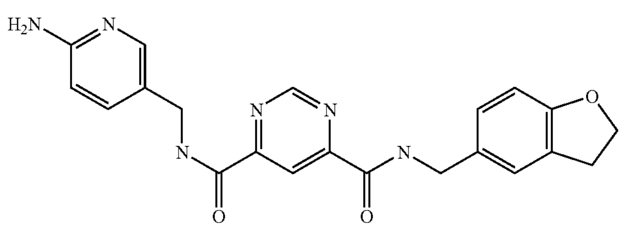 | 405.31 |
| 51 | 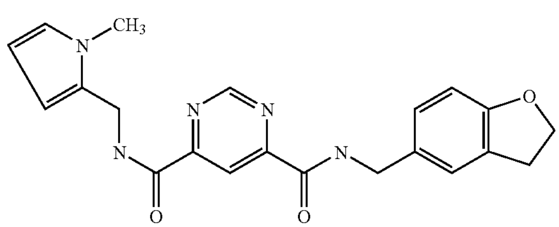 | 392.09 |
| 52 | 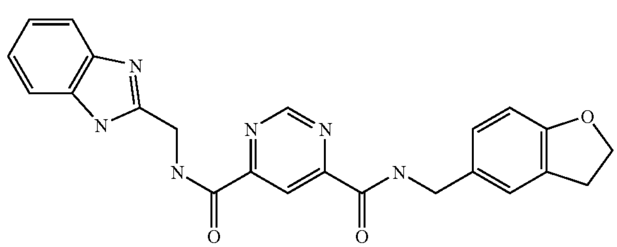 | 429.12 |

TABLE 1-continued

| Example | Structure | MS (ESI+) |
|---|---|---|
| 53 | 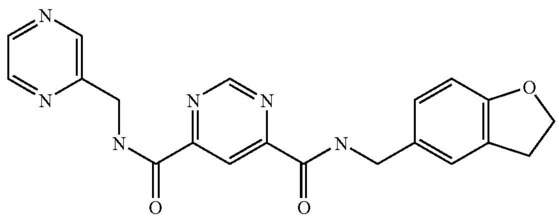 | 391.05 |
| 54 | 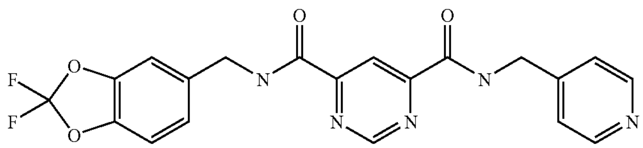 | 428.14 |
| 55 | 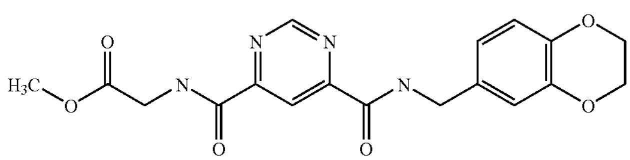 | 387.18 |
| 56 | 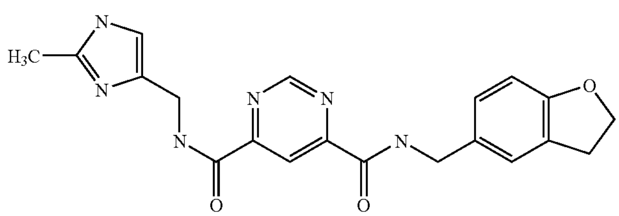 | 393.24 |
| 57 | 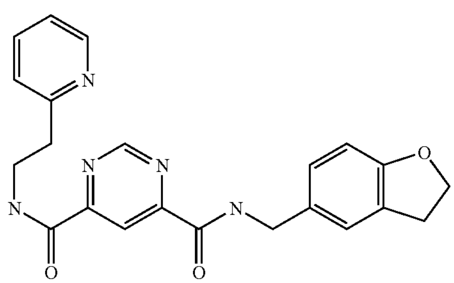 | 404.36 |
| 58 | 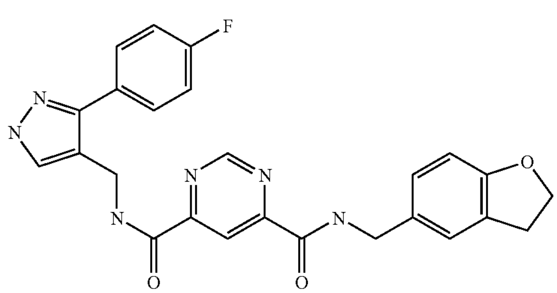 | 473.30 |
| 59 | 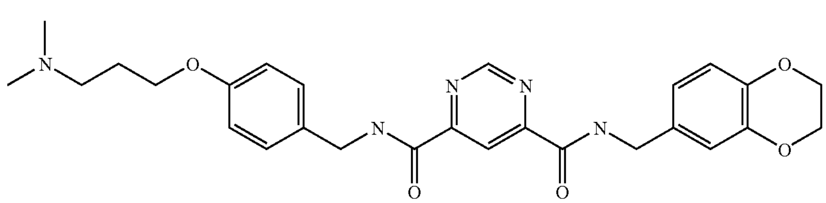 | 506.26 |

TABLE 1-continued

| Example | Structure | MS (ESI+) |
|---|---|---|
| 60 | 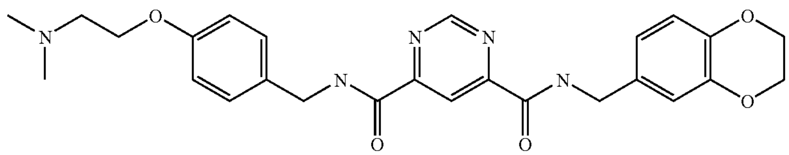 | 492.39 |
| 61 | 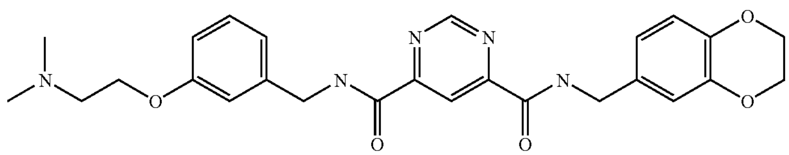 | 492.31 |
| 62 | 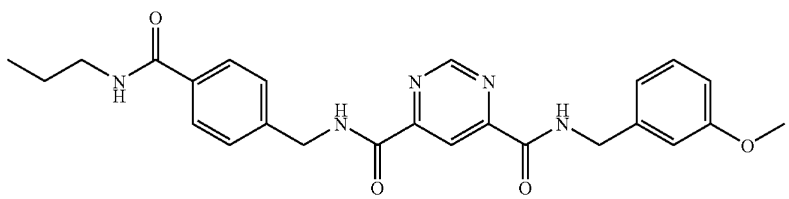 | 462.36 |
| 63 | 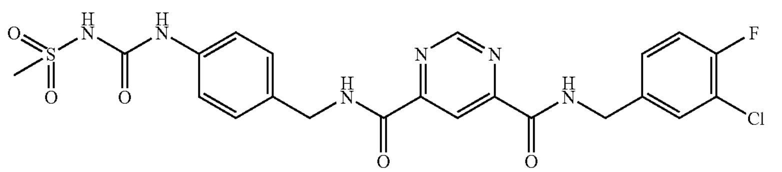 | 535.06 |
| 64 | 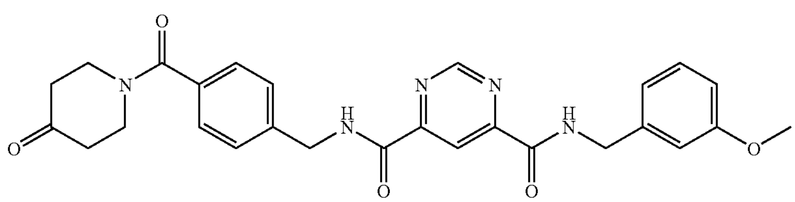 | 502.19 |
| 65 | 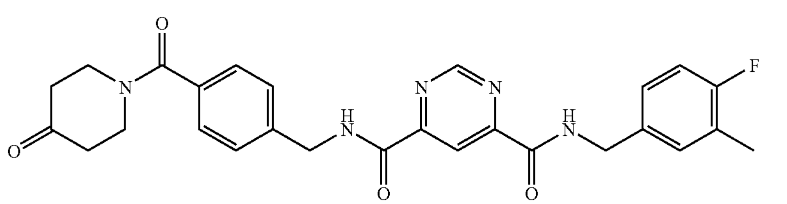 | 503.9 |
| 66 | 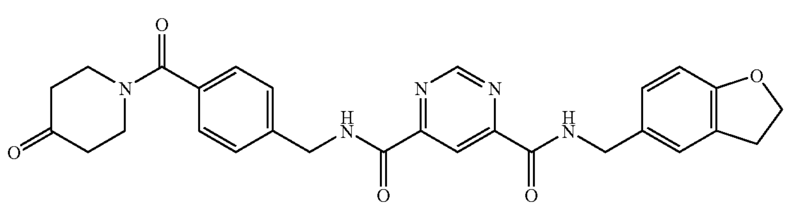 | 514.15 |
| 67 | 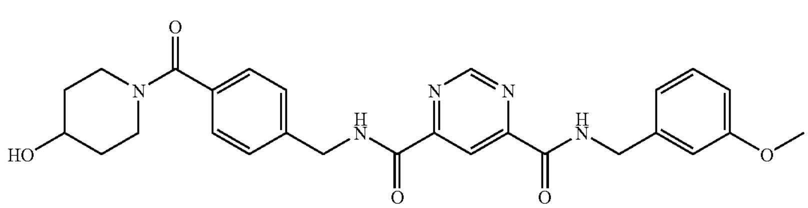 | 504.14 |

TABLE 1-continued

| Example | Structure | MS (ESI+) |
|---|---|---|
| 68 | 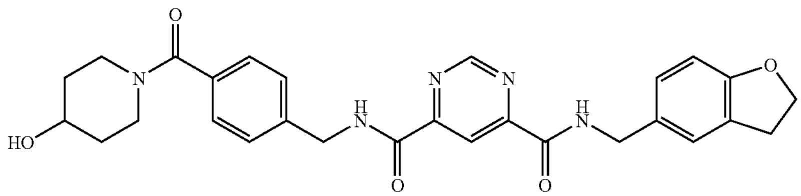 | 516.19 |
| 69 | 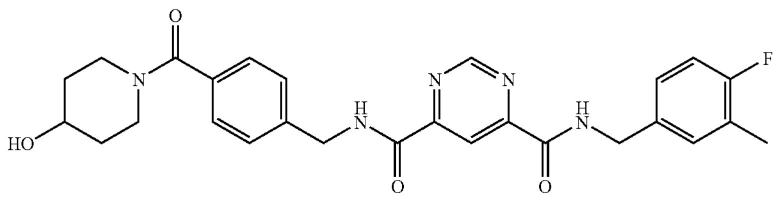 | 506.16 |
| 70 | 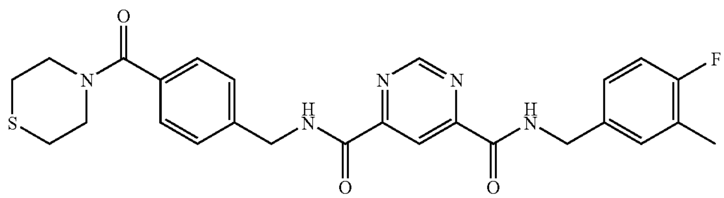 | 508.16 |
| 71 | 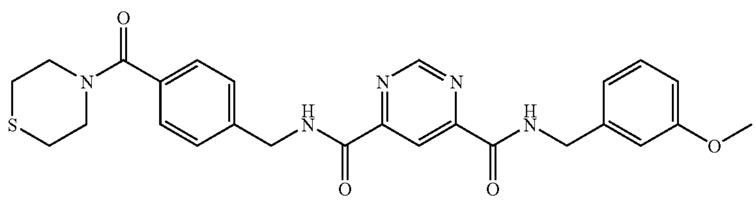 | 506.09 |
| 72 | 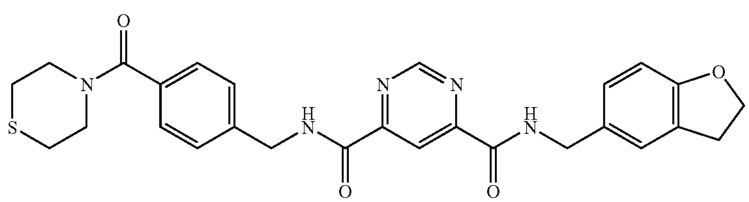 | 518.1 |
| 73 | 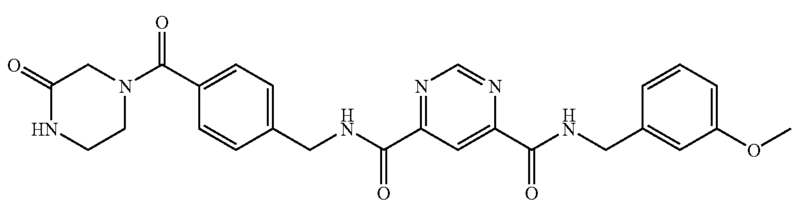 | 503.14 |
| 74 | 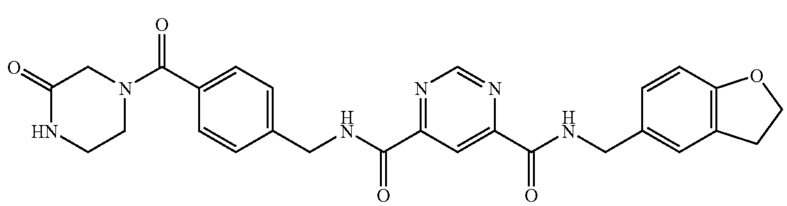 | 515.14 |

TABLE 1-continued

| Example | Structure | MS (ESI+) |
|---|---|---|
| 75 | 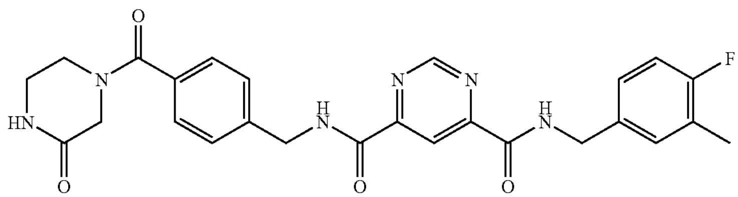 | 505.13 |
| 75a | 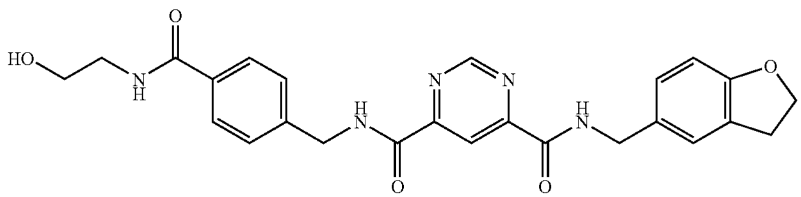 | 476.14 |
| 76 | 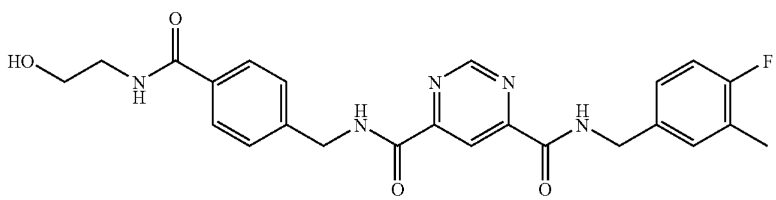 | 466.12 |
| 77 | 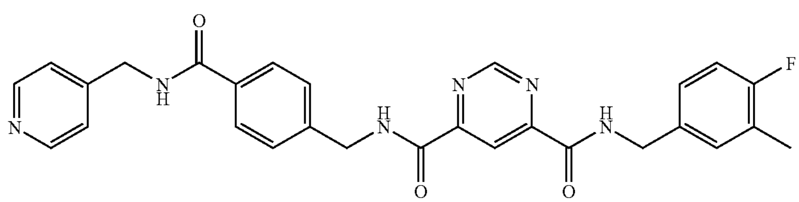 | 513.05 |
| 78 | 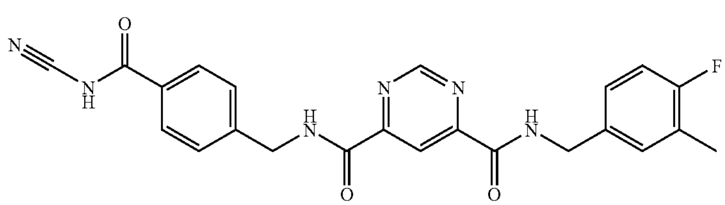 | 464.12 |
| 79 | 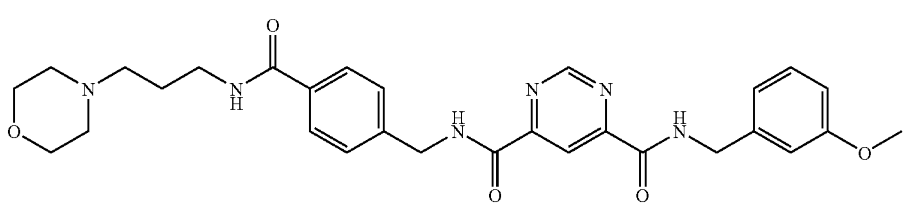 | 547.16 |
| 80 | 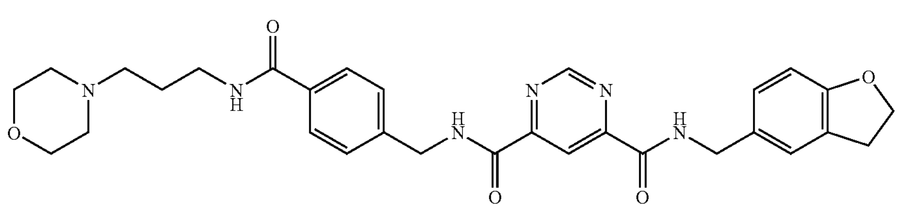 | 559.18 |

TABLE 1-continued

| Example | Structure | MS (ESI+) |
|---|---|---|
| 81 | 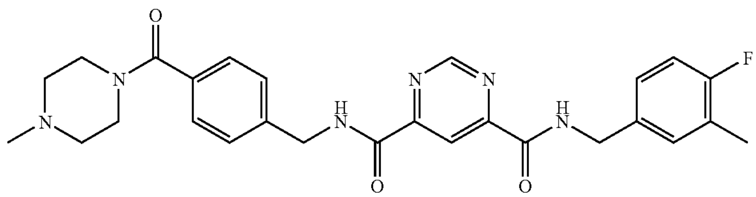 | 505.13 |
| 82 | 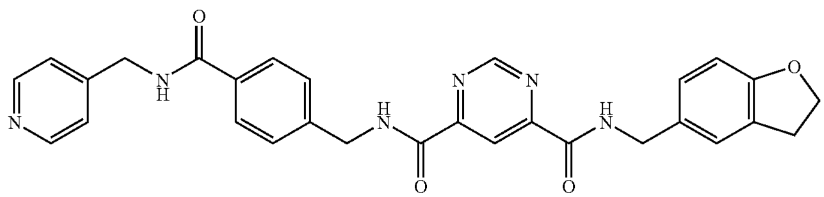 | 523.15 |
| 83 | 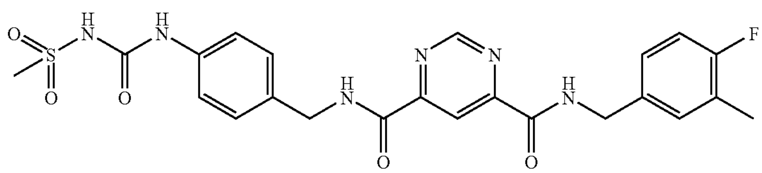 | 515.12 |
| 84 | 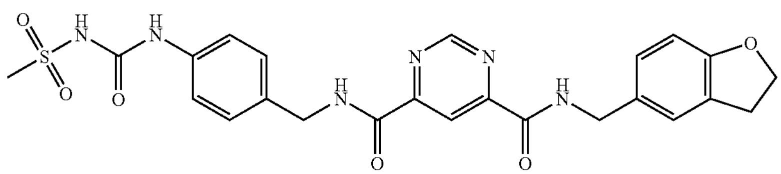 | 525.28 |
| 85 | 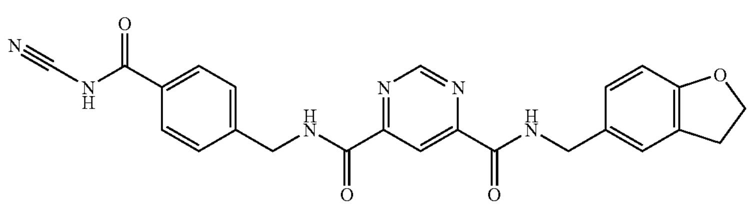 | 457.21 |
| 86 | 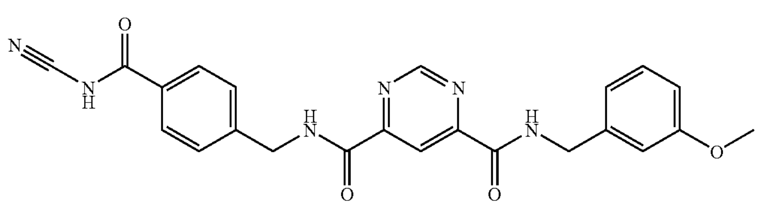 | 445.13 |
| 87 | 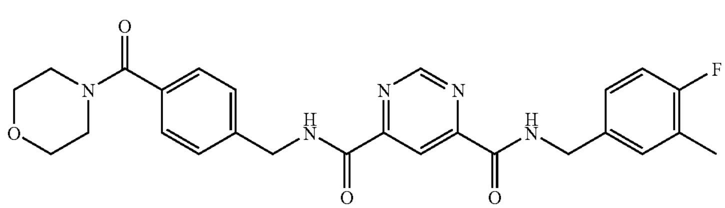 | 492.39 |
| 88 | 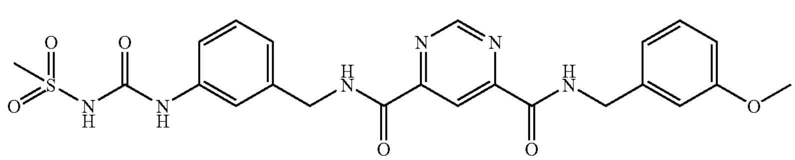 | 513.28 |

TABLE 1-continued

| Example | Structure | MS (ESI+) |
|---|---|---|
| 89 | 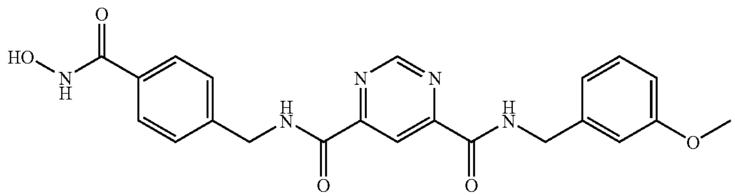 | 436.18 |
| 90 | 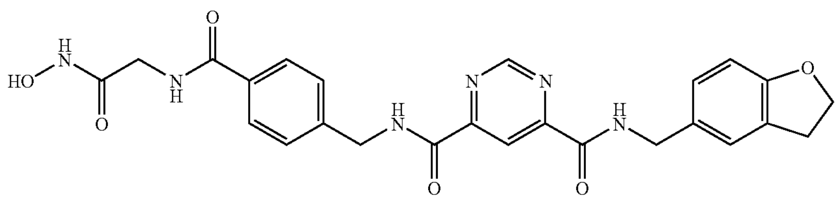 | 505.23 |
| 91 | 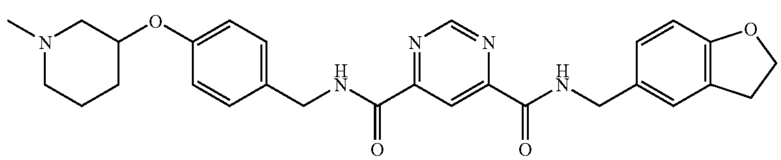 | 502.25 |
| 92 | 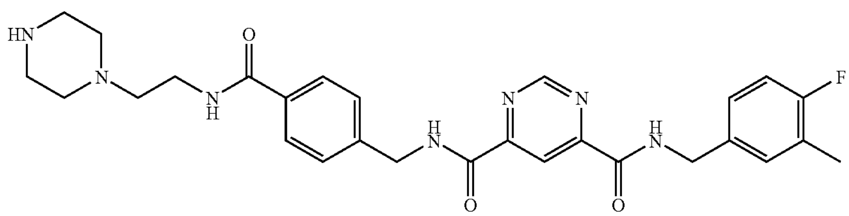 | 534.21 |
| 93 | 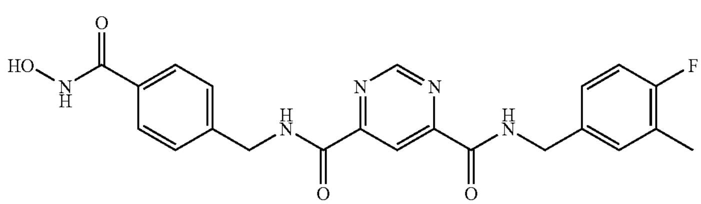 | 438.18 |
| 94 | 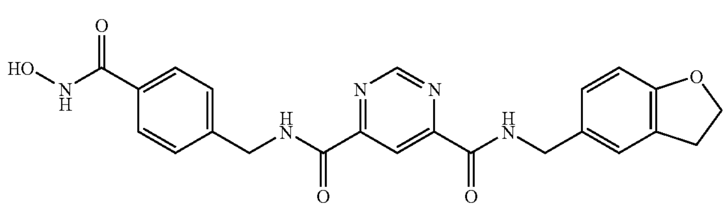 | 448.15 |
| 95 | 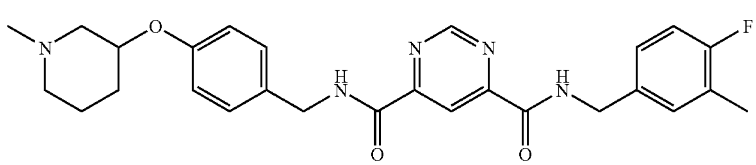 | 492.23 |

TABLE 1-continued

| Example | Structure | MS (ESI+) |
|---------|-----------|-----------|
| 96 | 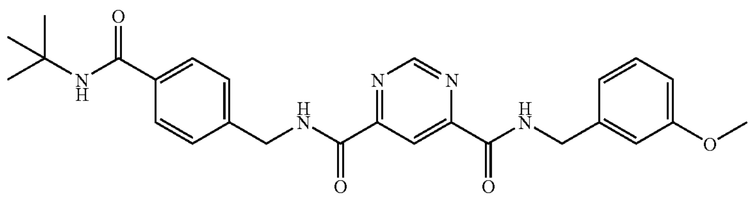 | 476.27 |
| 97 | 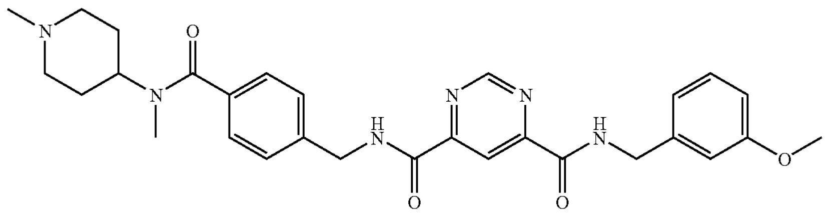 | 531.31 |
| 98 | 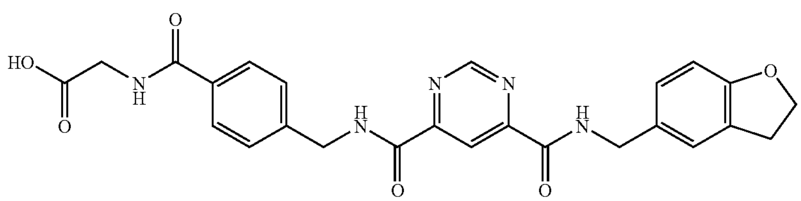 | 490.26 |
| 99 | 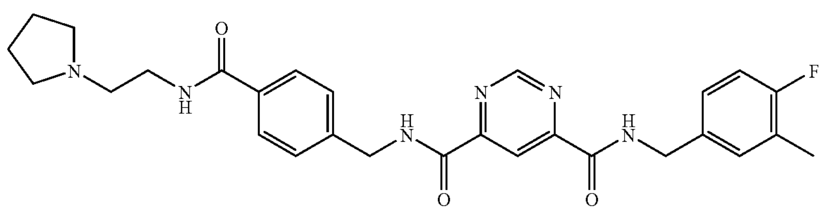 | 519.28 |
| 100 | 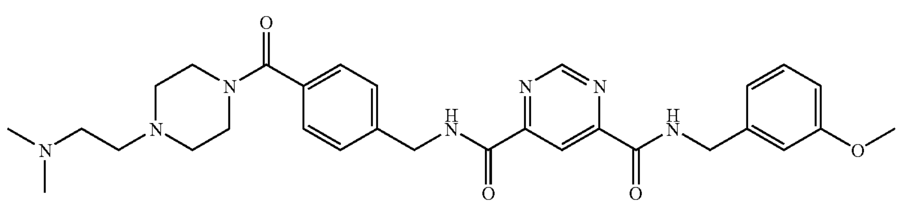 | 560.31 |
| 101 | 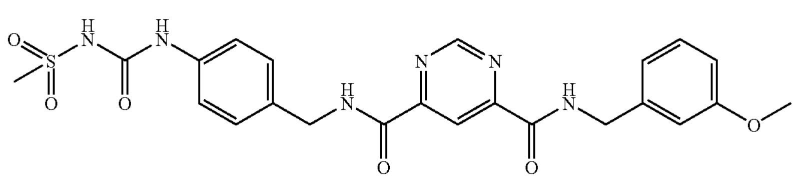 | 513.25 |
| 102 | 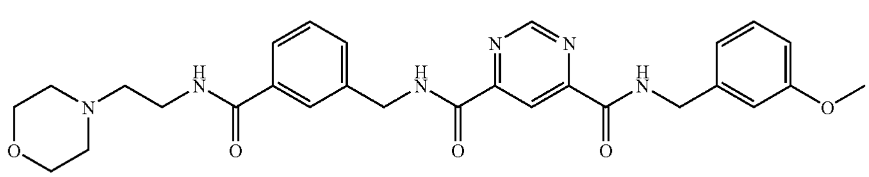 | 533.23 |

TABLE 1-continued
| Example | Structure | MS (ESI+) |
|---|---|---|
| 103 | 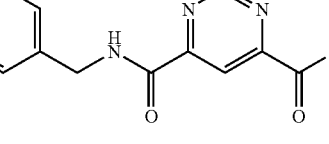 | 480.29 |
| 104 | 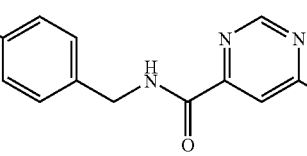 | 518.25 |
| 105 | 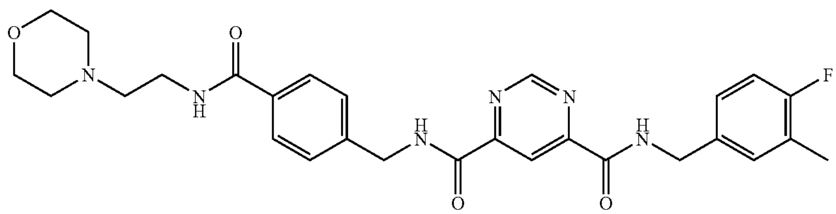 | 535.25 |
| 106 | 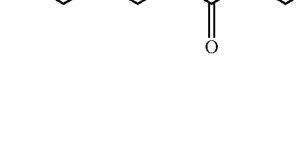 | 494.18 |
| 107 | 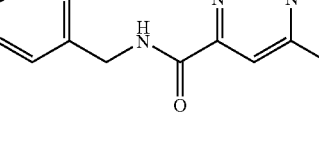 | 490.25 |
| 108 | 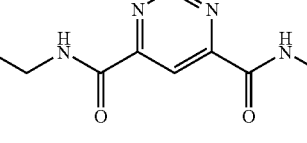 | 517.28 |
| 109 | 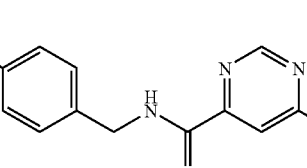 | 503.28 |

TABLE 1-continued
| Example | Structure | MS (ESI+) |
|---------|-----------|-----------|
| 110 | 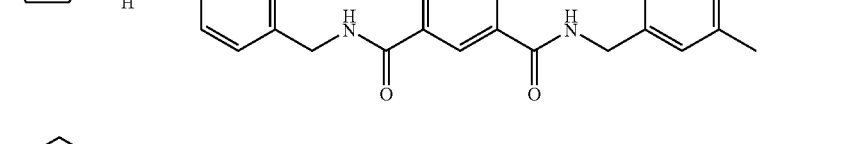 | 505.23 |
| 111 | 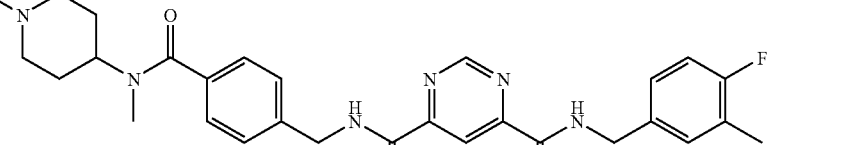 | 533.26 |
| 112 | 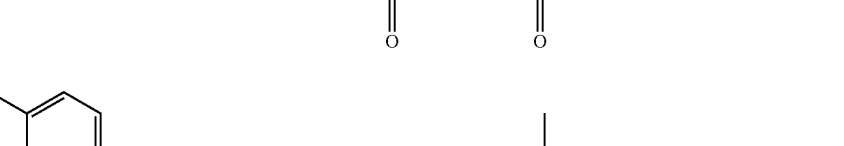 | 450.31 |
| 113 | 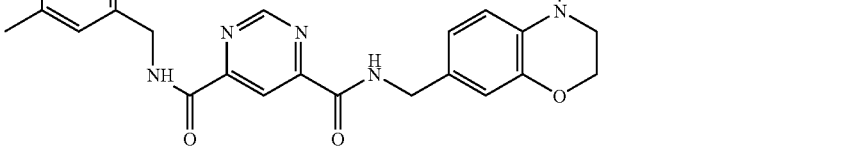 | 519.27 |
| 114 | 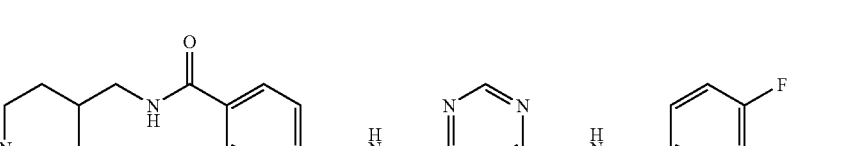 | 503.24 |
| 115 | 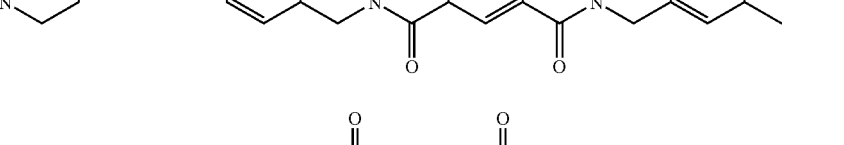 | 566.25 |
| 116 | 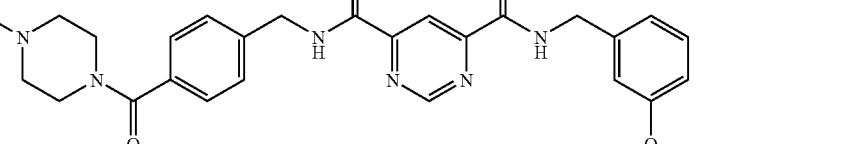 | 519.25 |

TABLE 1-continued

| Example | Structure | MS (ESI+) |
|---------|-----------|-----------|
| 117 | 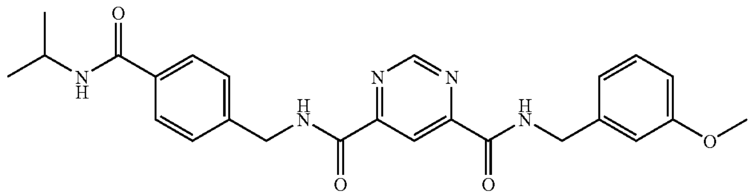 | 462.37 |
| 118 | 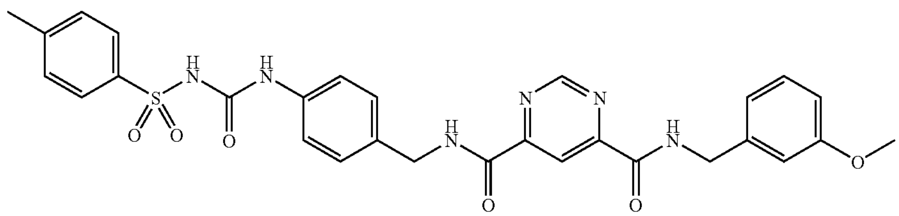 | 589.25 |
| 119 | 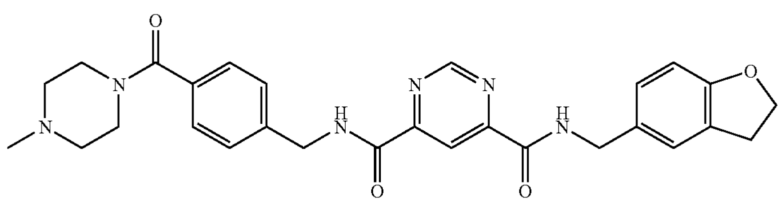 | 515.36 |
| 120 | 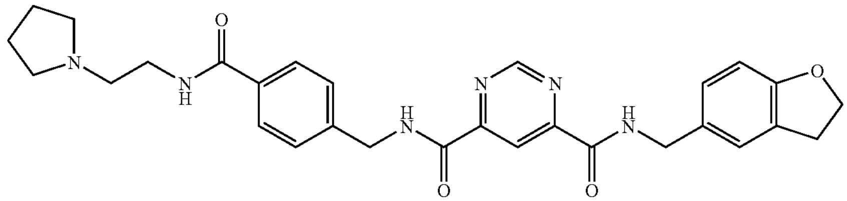 | 529.29 |
| 121 | 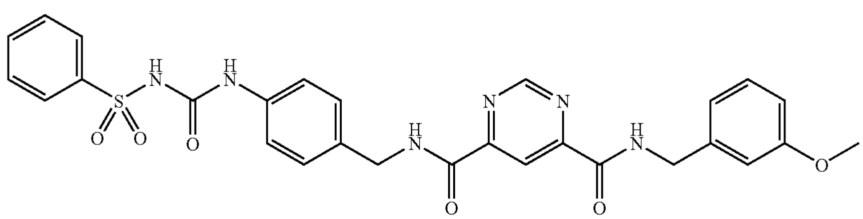 | 575.23 |
| 122 | 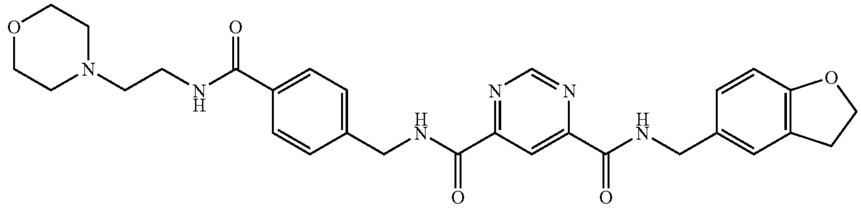 | 545.24 |
| 123 | 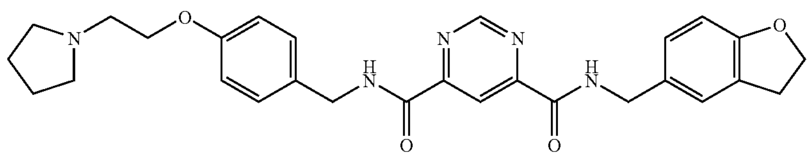 | 502.2 |

TABLE 1-continued

| Example | Structure | MS (ESI+) |
|---------|-----------|-----------|
| 125 | 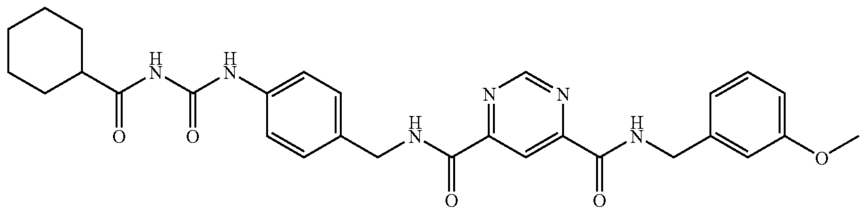 | 545.25 |
| 126 | 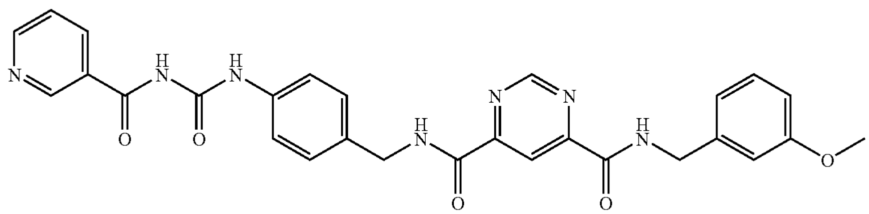 | 540.25 |
| 127 | 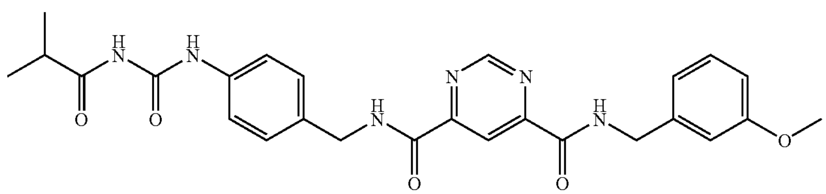 | 505.25 |
| 128 | 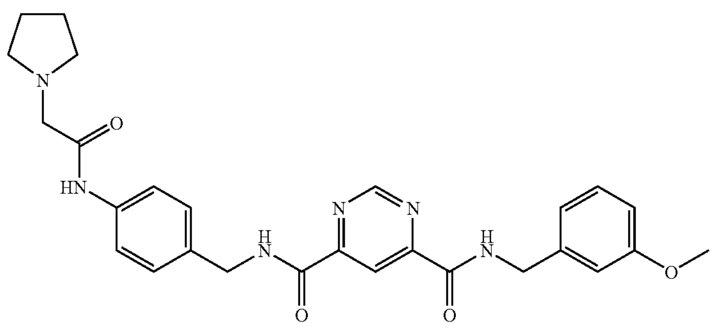 | 503.35 |
| 129 | 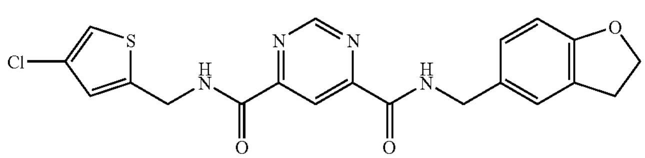 | 429.13 |
| 130 | 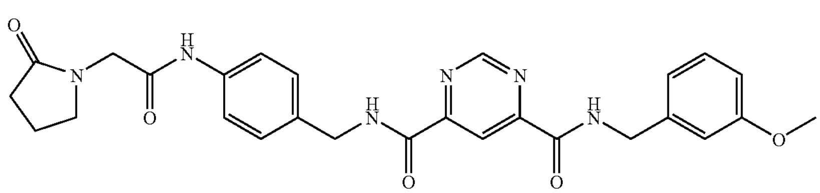 | 517.32 |
| 131 | 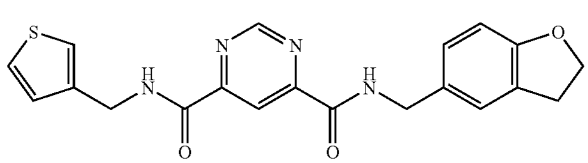 | 395.23 |

TABLE 1-continued

| Example | Structure | MS (ESI+) |
|---|---|---|
| 132 | 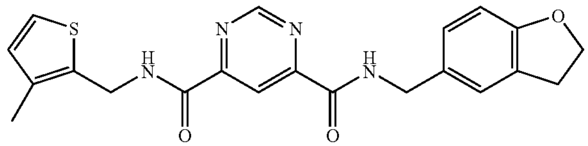 | 409.27 |
| 133 | 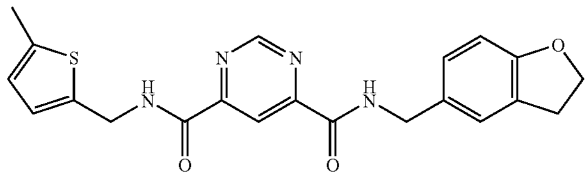 | 409.17 |
| 134 | 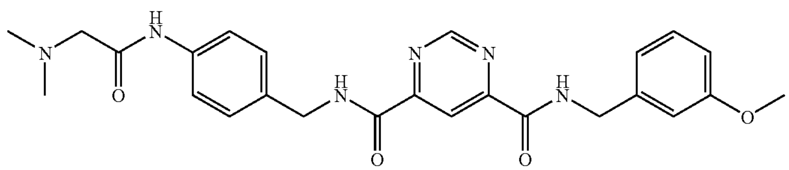 | 477.3 |
| 135 | 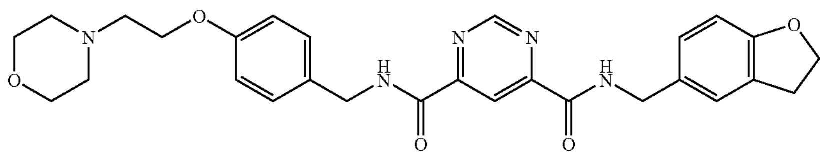 | 518.34 |
| 136 | 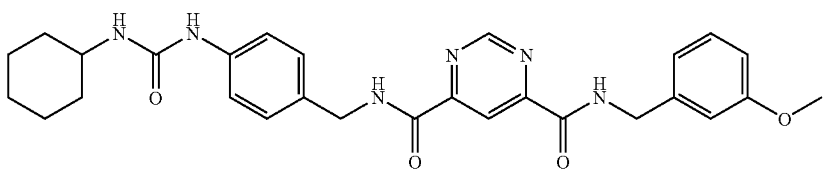 | 517.49 |
| 137 | 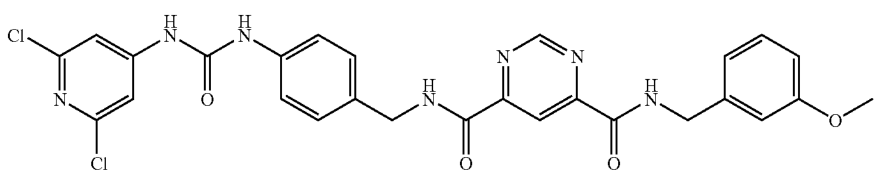 | 580.35 |
| 138 | 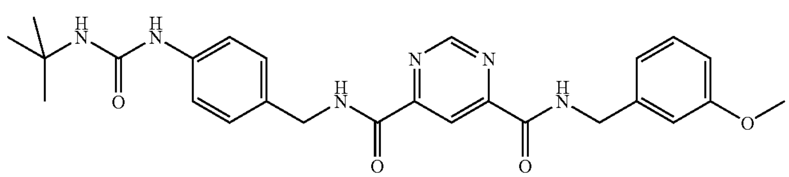 | 491.34 |
| 139 | 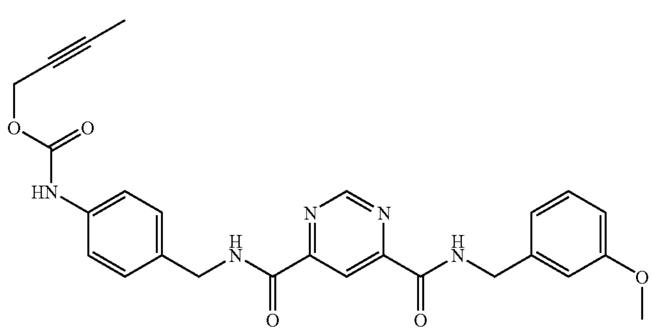 | 488.22 |

TABLE 1-continued
| Example | Structure | MS (ESI+) |
|---|---|---|
| 140 | 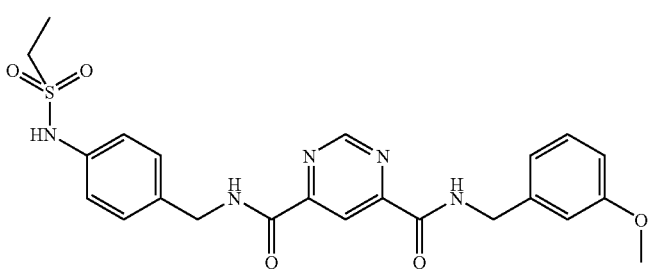 | 484.35 |
| 141 | 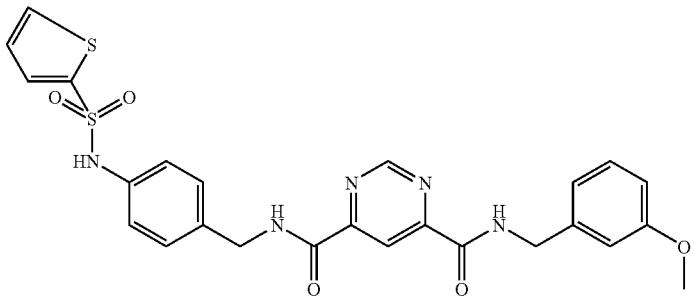 | 538.15 |
| 142 | 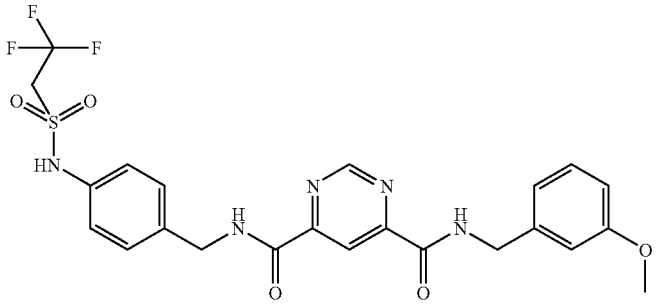 | 538.34 |
| 143 | 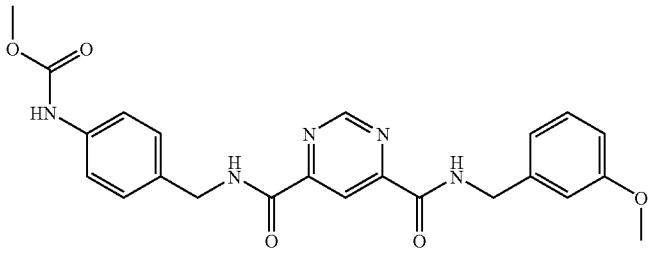 | 450.34 |
| 144 | 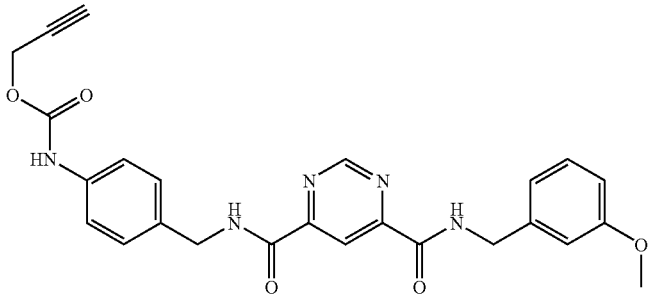 | 474.41 |

TABLE 1-continued

| Example | Structure | MS (ESI+) |
|---------|-----------|-----------|
| 145 | 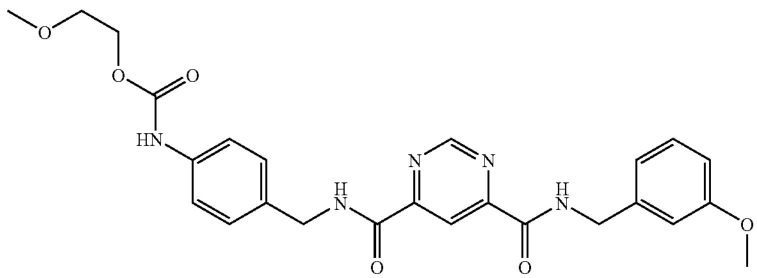 | 494.45 |
| 146 | 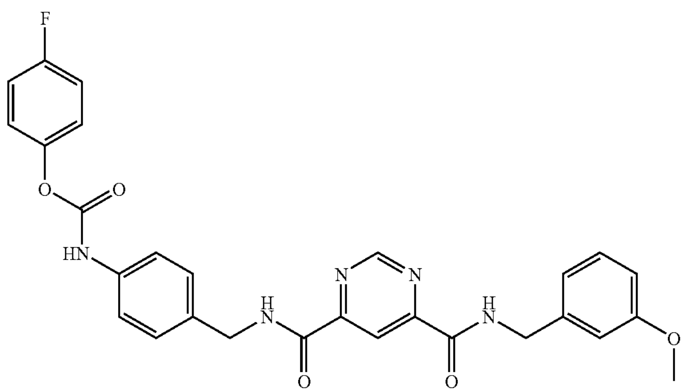 | 530.43 |
| 147 | 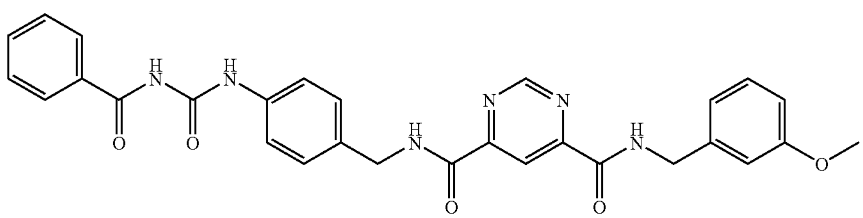 | 539.23 |
| 148 | 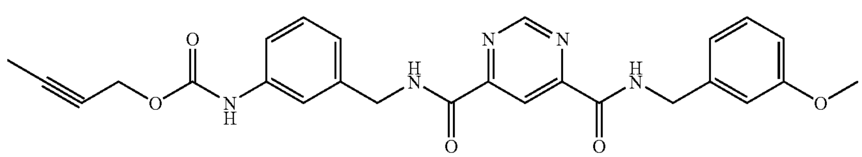 | 488.41 |
| 149 | 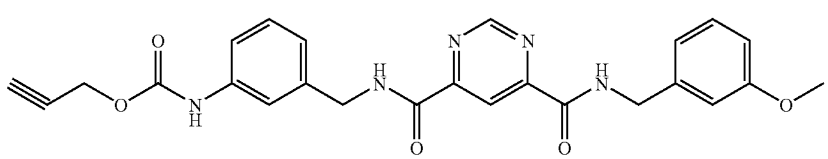 | 474.41 |
| 150 | 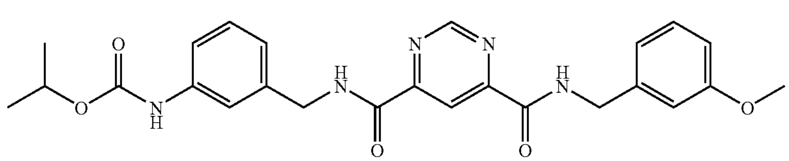 | 478.41 |

TABLE 1-continued

| Example | Structure | MS (ESI+) |
|---|---|---|
| 150a | 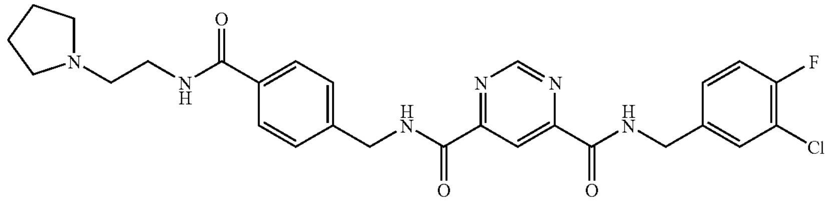 | 539.4 |
| 151 | 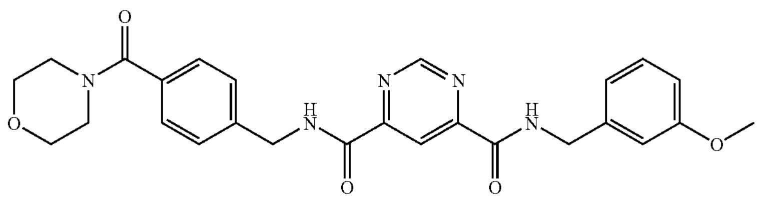 | 490.43 |
| 152 | 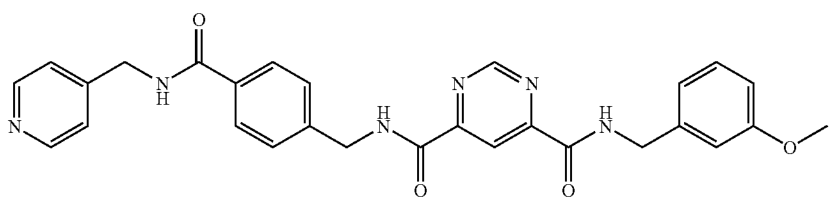 | 511.41 |
| 153 | 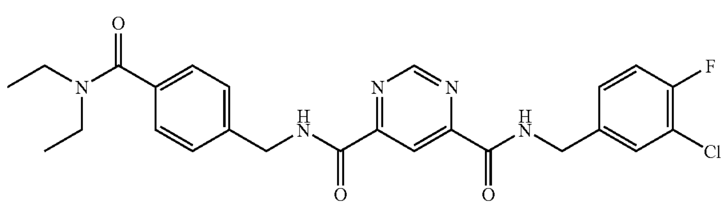 | 498.36 |
| 154 | 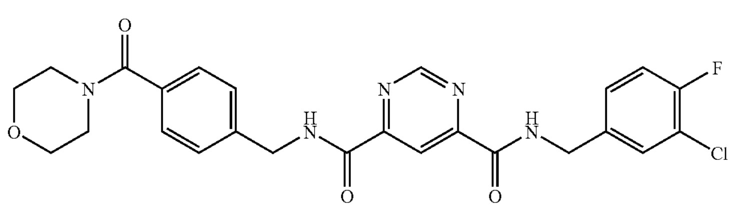 | 512.37 |
| 155 | 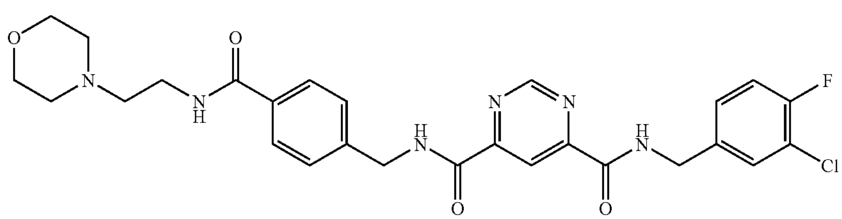 | 555.4 |

TABLE 1-continued

| Example | Structure | MS (ESI+) |
|---------|-----------|-----------|
| 156 | 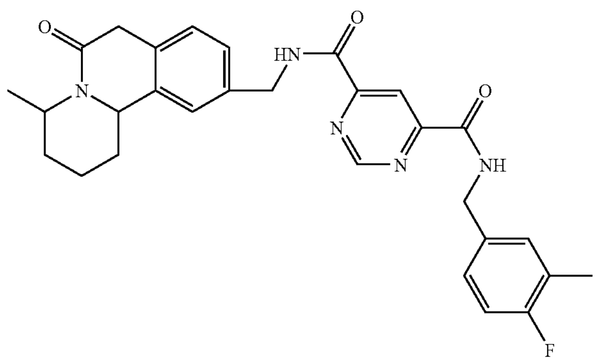 | 532.46 |
| 157 | 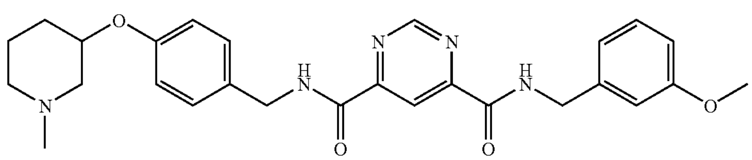 | 490.35 |
| 158 | 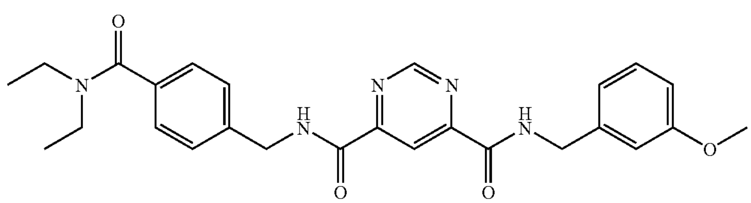 | 476.4 |
| 159 | 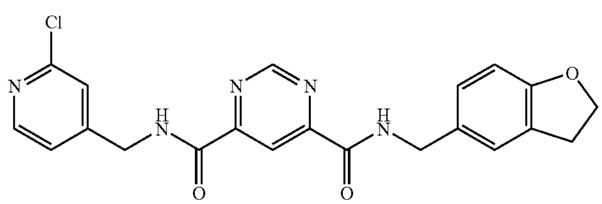 | 424.21 |
| 160 | 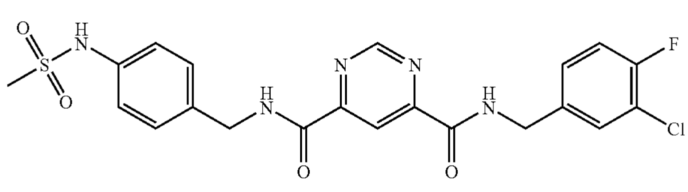 | 492.12 |

TABLE 1-continued

| Example | Structure | MS (ESI+) |
|---|---|---|
| 161 | [structure: 4-(methylsulfonyl)benzyl and 3-methoxybenzyl pyrimidine-4,6-dicarboxamide] | 455.1 |

Experimental

Pharmacological Examples

Determining the enzyme activity of the catalytic domain of human collagenase 3 (MMP-13).

This protein is obtained as an inactive proenzyme from INVITEK, Berlin (Catalogue No. 30 100 803). Activating the proenzyme:

2 parts by volume of proenzyme are incubated with 1 part by volume of APMA solution at 37° C. for 1.5 hours. The APMA solution is prepared from a 10 mmol/L solution of p-aminophenylmercuric acetate in 0.1 mmol/L NaOH by diluting with 3 parts by volume of tris/HCl buffer, pH 7.5 (see below). The pH is adjusted to between 7.0 and 7.5 by adding 1 mmol/L HCl. After the enzyme has been activated, it is diluted to a concentration of 1.67 μg/ml using the tris/HCl buffer.

In order to measure the enzyme activity, 10 μL of enzyme solution are incubated for 15 minutes with 10 μL of a 3% (v/v) buffered solution of dimethyl sulfoxide (reaction 1). In order to measure the enzyme inhibitor activity, 10 μL of enzyme solution are incubated with 10 μL of a 3% (v/v) buffered solution of dimethyl sulfoxide containing the enzyme inhibitor (reaction 2).

In the case of both reaction 1 and reaction 2, the enzyme reaction is monitored by fluorescence spectroscopy (328 nm (extinction)/393 nm (emission)) after adding 10 μL of a 3% (v/v) aqueous solution of dimethyl sulfoxide containing 0.75 mmol of the substrate/L.

The enzyme activity is depicted as increase in extinction/minute.

The effect of the inhibitor is calculated as a percentage inhibition using the following formula:

% inhibition=100−[(increase in extinction/minute in reaction 2)/(increase in extinction/minute in reaction 1)×100].

The $IC_{50}$, i.e. the inhibitor concentration which is required for inhibiting the enzyme activity by 50%, is determined graphically by plotting the percentage inhibitions at different inhibitor concentrations.

The buffer solution contains 0.05% Brij (Sigma, Deisenhofen, Germany) and 0.1 mol of tris/HCl/L, 0.1 mol of NaCl/L and 0.01 mol of $CaCl_2$/L (pH=7.5). The enzyme solution contains 1.67 μg of the enzyme domain/mL.

The substrate solution contains 0.75 mmol/L of the fluorogenic substrate (7-methoxycoumarin-4-yl)acetyl-Pro-Leu-Gly-Leu-3-(2′,4′-dinitrophenyl)-L-2,3-diaminopropionyl-Ala-Arg-$NH_2$ (Bachem, Heidelberg, Germany).

Table 2 below shows the results for enzyme activity of the catalytic domain of human collagenase 3 (MMP-13).

TABLE 2

| Example | $IC_{50}$ MMP13 (nM) |
|---|---|
| 3 | 4 |
| 4 | 20 |
| 5 | 8 |
| 6 | 20 |
| 36 | 10 |
| 39 | 30 |
| 44 | 200 |
| 62 | 13 |
| 63 | 9 |
| 64 | 10 |
| 65 | 15 |
| 66 | 10 |
| 67 | 15 |
| 68 | 22 |
| 69 | 32 |
| 70 | 24 |
| 71 | 9 |
| 72 | 10 |
| 73 | 25 |
| 74 | 30 |
| 75 | 70 |
| 75a | 34 |
| 76 | 23 |
| 78 | 3 |
| 82 | 30 |
| 83 | 5 |
| 84 | 3.2 |
| 85 | 3.5 |
| 86 | 2.5 |
| 87 | 24 |
| 88 | 33 |
| 89 | 18 |
| 93 | 20 |
| 94 | 20 |
| 96 | 50 |
| 98 | 20 |
| 99 | 50 |
| 101 | 2 |
| 105 | 23 |
| 106 | 40 |
| 109 | 50 |
| 112 | 45 |
| 114 | 50 |
| 115 | 20 |
| 118 | 2.4 |
| 119 | 35 |
| 121 | 30 |
| 122 | 43 |
| 125 | 4 |
| 126 | 2.3 |
| 127 | 3.3 |
| 128 | 60 |
| 129 | 22 |
| 135 | 20 |
| 136 | 20 |
| 137 | 40 |

TABLE 2-continued

| Example | IC$_{50}$ MMP13 (nM) |
|---|---|
| 138 | 50 |
| 139 | 10 |
| 144 | 9 |
| 147 | 3 |
| 150 | 80 |
| 151 | 9 |
| 153 | 15 |
| 154 | 22 |
| 158 | 4 |

Determining the enzyme activity of the catalytic domain of human neutrophil collagenase (MMP-8) and of human Stromelysin (MMP-3).

The enzymes human neutrophil collagenase and human Stromelysin, prepared as active catalytic domains, were carried out as described in Weithmann et al Inflamm Res, 46 (1997), pages 246–252, the content of which is incorporated by reference. The measurement of the enzyme activity, and the determination of the inhibitory effect of inhibitors on the enzyme activity, were also carried out as described in that publication.

When determining human neutrophil collagenase and human Stromelysin, the compounds described in the above examples in each case had IC50 values of more than 100 000 nM. These compounds are therefore virtually without activity as regards inhibiting MMP 3 and 8.

We claim:

1. A compound of the formula I

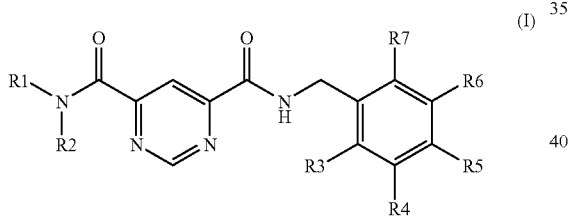

wherein, for the case a)

R1 is hydrogen or —(C$_1$–C$_6$)-alkyl,

R2 is —(C$_1$–C$_6$)-alkyl, wherein, alkyl is substituted, one, two or three times, by
1. —(C$_1$–C$_6$)-alkyl-O—(C$_6$–C$_{14}$)-aryl,
2. —(C$_0$–C$_6$)-alkyl-N(R8)-C(O)—O—(C$_1$–C$_6$)-alkyl, wherein, R8 is
   i) hydrogen,
   ii) —(C$_1$–C$_6$)-alkyl, wherein, alkyl is unsubstituted or substituted, one, two or three times, independently of each other, by —NH$_2$, —CN, —OH, —C(O)—OH, —C(O)—O—(C$_1$–C$_6$)-alkyl, —C(O)—NH—OH, NO$_2$ or halogen, or
   iii) OH,
3. —(C(O)—N(R9)-(R10), wherein, R9 and R10 are identical or different and are, independently of each other,
   i) hydrogen or
   ii) —(C$_1$–C$_6$)-alkyl, or
R9 and R10 form, together with the nitrogen atom to which they are bonded, a 5-, 6- or 7-membered saturated ring, where a heteroatom from the series oxygen, sulfur and nitrogen can also replace one or two further carbon atoms and, in the case of nitrogen, the nitrogen atoms can, independently of each other, be unsubstituted or substituted by (C$_1$–C$_6$)-alkyl, 4. —(C$_6$–C$_{14}$)-aryl, wherein, aryl is substituted, one, two or three times, independently of each other, by
4.1) —(C$_1$–C$_6$)-alkyl-C(O)—O—R8, wherein, R8 has the abovementioned meaning,
4.2) —(C$_0$–C$_6$)-alkyl-C(O)—N(R9)-(R10), wherein, R9 and R10 have the abovementioned meaning,
4.3) —(C$_0$–C$_6$)-alkyl-C(O)—NH—CN,
4.4) —(C$_0$–C$_6$)-alkyl-C(O)—(C$_0$–C$_6$)-alkyl-Het, wherein, Het is a saturated or unsaturated, monocyclic or bicyclic, 3- to 10-membered heterocyclic ring system which contains 1, 2 or 3 identical or different ring heteroatoms from the series nitrogen, oxygen and sulfur and is unsubstituted or substituted, one, two or three times, independently of each other, by
   a) halogen,
   b) cyano,
   c) nitro,
   d) hydroxyl,
   e) amino,
   f) —C(O)—O—(C$_1$–C$_6$)-alkyl,
   g) —C(O)—OH,
   h) —(C$_1$–C$_6$)-alkyl, wherein, alkyl is unsubstituted or substituted, one, two or three times, by halogen,
   i) —O—(C$_1$–C$_6$)-alkyl, wherein, alkyl is unsubstituted or substituted, one, two or three times, by halogen, or —N(R9)-(R10),
   j) =O,
   k) -Het,
   l) —(C$_2$–C$_6$)-alkenyl, wherein, alkenyl is unsubstituted or substituted, one, two or three times, by halogen, or —N(R9)-(R10), or
   m) —(C$_2$–C$_6$)-alkynyl, wherein, alkynyl is unsubstituted or substituted, one, two or three times, by halogen or —N(R9)-(R10),
4.5) —(C$_0$–C$_6$)-alkyl-C(O)—(C$_1$–C$_6$)-alkyl-OH,
4.6) —O—(C$_0$–C$_6$)-alkyl-C(O)—N(R9)-(R10), wherein, R9 and R10 have the abovementioned meaning,
4.7) —S(O)$_y$—(C$_1$–C$_6$)-alkyl-C(O)—O—R8, wherein, R8 has the abovementioned meaning and y is 1 or 2,
4.8) —S(O)$_z$—(C$_1$–C$_6$)-alkyl-C(O)—N(R9)-(R10), wherein, R9 and R10 have the abovementioned meaning and z is zero, 1 or 2,
4.9) —(C$_0$–C$_6$)-alkyl-C(O)—N(R8)-(C$_0$–C$_6$)-alkyl-N(R9)-(R10), wherein, R8, R9 and R10 have the abovementioned meaning,
4.10) —(C$_0$–C$_6$)-alkyl-C(O)—N(R8)-(C$_0$–C$_6$)-alkyl-Het, wherein, R8 has the abovementioned meaning and Het has the abovementioned meaning and is unsubstituted or substituted, one, two or three times, independently of each other, by the abovementioned radicals a) to m),
4.11) —(C$_0$–C$_6$)-alkyl-C(O)—N(R8)-(C$_0$–C$_6$)-alkyl-(C$_6$–C$_{14}$)-aryl, wherein, aryl is unsubstituted or substituted, one, two or three times, independently of each other, by the abovementioned radicals a) to m),
4.12) —(C$_1$–C$_6$)-alkyl-N(R9)-(R10), wherein, R9 and R10 have the abovementioned meaning, 4.13) —($CH_2$)$_y$—N(R8)-C(O)—($C_1$–$C_6$)-alkyl, wherein, alkyl is unsubstituted or substituted, one, two or three times, independently of each other, by the abovementioned radicals a) to m) and y is 1 or 2, 4.14) —($C_0$–$C_4$)-alkyl-N(R8)-C(O)—($C_0$–$C_6$)-alkyl-($C_6$–$C_{14}$)-aryl, wherein, aryl is unsubstituted or substituted, one, two or three times, independently of each other, by the abovementioned radicals a) to m), 4.15) —($C_0$–$C_4$)-alkyl-N(R8)-C(O)—($C_0$–$C_6$)-alkyl-Het, wherein, Het is unsubstituted or substituted, one, two or three times, independently of each other, by the abovementioned radicals a) to m), 4.16) —($C_0$–$C_4$)-alkyl-N(R8)-C(O)—O—($C_1$–$C_6$)-alkyl, wherein, alkyl is unsubstituted or substituted, one, two or three times, independently of each other, by the abovementioned radicals a) to m), 4.17) —($C_0$–$C_4$)-alkyl-N(R8)-C(O)—O—($C_1$–$C_6$)-alkenyl, wherein, alkenyl is unsubstituted or substituted, one, two or three times, independently of each other, by the abovementioned radicals a) to m), 4.18) —($C_0$–$C_4$)-alkyl-N(R8)-C(O)—O—($C_1$–$C_6$)-alkynyl, wherein, alkynyl is unsubstituted or substituted, one, two or three times, independently of each other, by the abovementioned radicals a) to m), 4.19) —($C_0$–$C_4$)-alkyl-N(R8)-C(O)—O—($C_0$–$C_6$)-alkyl-($C_6$–$C_{14}$)-aryl, wherein, aryl is unsubstituted or substituted, one, two or three times, independently of each other, by the abovementioned radicals a) to m), 4.20) —($C_0$–$C_4$)-alkyl-N(R8)-C(O)—O—($C_0$–$C_6$)-alkyl-Het, wherein, Het is unsubstituted or substituted, one, two or three times, independently of each other, by the abovementioned radicals a) to m), 4.21) —($C_0$–$C_4$)-alkyl-N(R8)-C(O)—($C_0$–$C_6$)-alkyl-N(R11)-R12, wherein, R8 has the abovementioned meaning and R11 and R12 are identical or different and are, independently of each other, 4.21.1) hydrogen, 4.21.2) —($C_1$–$C_6$)-alkyl, 4.21.3) —($C_0$–$C_6$)-alkyl-($C_6$–$C_{14}$)-aryl, wherein, aryl is unsubstituted or substituted, one, two or three times, independently of each other, by the abovementioned radicals a) to m), 4.21.4) —($C_0$–$C_6$)-alkyl-Het, wherein, Het is unsubstituted or substituted, one, two or three times, independently of each other, by the abovementioned radicals a) to m), 4.21.5) —C(O)—($C_1$–$C_6$)-alkyl, wherein, alkyl is unsubstituted or substituted, one, two or three times, independently of each other, by the abovementioned radicals a) to m), 4.21.6) —C(O)—($C_3$–$C_6$)-cycloalkyl, wherein, cycloalkyl is unsubstituted or substituted, one, two or three times, independently of each other, by the abovementioned radicals a) to m), 4.21.7) —C(O)—($C_0$–$C_6$)-alkyl-($C_6$–$C_{14}$)-aryl, wherein, aryl is unsubstituted or substituted, one, two or three times, independently of each other, by the abovementioned radicals a) to m), 4.21.8) —C(O)—($C_0$–$C_6$)-alkyl-Het, wherein, Het is unsubstituted or substituted, one, two or three times, independently of each other, by the abovementioned radicals a) to m), 4.21.9) —$SO_2$—($C_0$–$C_6$)-alkyl, wherein, alkyl is unsubstituted or substituted, one, two or three times, independently of each other, by the abovementioned radicals a) to m), 4.21.10) —NH—$SO_2$—($C_0$–$C_6$)-alkyl, wherein, alkyl is unsubstituted or substituted, one, two or three times, independently of each other, by the abovementioned radicals a) to m), 4.21.11) —$SO_2$—($C_0$–$C_6$)-alkyl-($C_6$–$C_{14}$)-aryl-($C_0$–$C_6$)-alkyl, wherein, aryl is unsubstituted or substituted, one, two or three times, independently of each other, by the abovementioned radicals a) to m), 4.21.12) —$SO_2$—($C_0$–$C_6$)-alkyl-Het, wherein, Het is unsubstituted or substituted, one, two or three times, independently of each other, by the abovementioned radicals a) to m), 4.22) —($C_0$–$C_4$)-alkyl-N(R8)-S(O)$_2$—($C_0$–$C_6$)-alkyl-($C_6$–$C_{14}$)-aryl, wherein, aryl is unsubstituted or substituted, one, two or three times, independently of each other, by the abovementioned radicals a) to m) and R8 has the abovementioned meaning, 4.23) —($C_0$–$C_4$)-alkyl-N(R8)-S(O)$_2$—($C_0$–$C_6$)-alkyl-Het, wherein, Het is unsubstituted or substituted, one, two or three times, independently of each other, by the abovementioned radicals a) to m) and R8 has the abovementioned meaning, 4.24) —($C_0$–$C_4$)-alkyl-N(R8)-S(O)$_2$—N(R8)-($C_1$–$C_6$)-alkyl, wherein, alkyl is unsubstituted or substituted, one, two or three times, independently of each other, by the abovementioned radicals a) to m) and R8 has the abovementioned meaning, 4.25) —($C_0$–$C_4$)-alkyl-N(R8)-S(O)$_2$—N(R8)-($C_0$–$C_6$)-alkyl-($C_6$–$C_{14}$)-aryl, wherein, aryl is unsubstituted or substituted, one, two or three times, independently of each other, by the abovementioned radicals a) to m) and R8 has the abovementioned meaning, 4.26) —($C_0$–$C_4$)-alkyl-N(R8)-S(O)$_2$—N(R8)-($C_0$–$C_6$)-alkyl-Het, wherein, Het is unsubstituted or substituted, one, two or three times, independently of each other, by the abovementioned radicals a) to m) and R8 has the abovementioned meaning, 4.27) —($C_0$–$C_4$)-alkyl-N(R8)-C(O)—N(R8)-$SO_2$—R13, wherein, R8 has the abovementioned meaning and R13 is —($C_1$–$C_6$)-alkyl or —($C_0$–$C_6$)-alkyl-($C_6$–$C_{14}$)-aryl, 4.28) —($C_0$–$C_4$)-alkyl-S(O)$_2$—N(R8)-($C_0$–$C_6$)-alkyl-($C_6$–$C_{14}$)-aryl wherein, aryl is unsubstituted or substituted, one, two or three times, independently of each other, by the abovementioned radicals a) to m) and R8 has the abovementioned meaning, 4.29) —($C_0$–$C_4$)-alkyl-S(O)$_2$—N(R8)-($C_0$–$C_6$)-alkyl-Het, wherein, Het is unsubstituted or substituted, one, two or three times, independently of each other, by the abovementioned radicals a) to m) and R8 has the abovementioned meaning, 4.30) —($C_0$–$C_4$)-alkyl-S(O)$_2$—N(R8)-($C_1$–$C_6$)-alkyl, wherein, alkyl is unsubstituted or substituted, one, two or three times, independently of each other, by the abovementioned radicals a) to m) and R8 has the abovementioned meaning, 4.31) —($C_0$–$C_4$)-alkyl-S(O)$_2$—($C_0$–$C_6$)-alkyl-($C_6$–$C_{14}$)-aryl, wherein, aryl is unsubstituted or substituted, one, two or three times, independently of each other, by the abovementioned radicals a) to m), 4.32) —($C_0$–$C_4$)-alkyl-S(O)$_2$—($C_0$–$C_6$)-alkyl-Het, wherein, Het is unsubstituted or substituted, one, two or three times, independently of each other, by the abovementioned radicals a) to m), 4.33) —O—($C_0$–$C_6$)-alkyl-Het, wherein, Het is unsubstituted or substituted, one, two or three times, independently of each other, by the abovementioned radicals a) to m), 4.34) —($C_0$–$C_4$)-alkyl-Het, wherein, Het is unsubstituted or substituted, one, two or three times, independently of each other, by the abovementioned radicals a) to m), or 4.35) -phenyl, wherein, the phenyl is unsubstituted or substituted, one, two or three times, by
  4.35.1) halogen,
  4.35.2) —($C_1$–$C_6$)-alkyl,
  4.35.3) —O—($C_1$–$C_6$)-alkyl or
  4.35.4) —S(O)$_2$—R16, wherein, R16 is ($C_1$–$C_6$)-alkyl or —NH$_2$, 5. —C(O)—N(R8)-($C_0$–$C_6$)-alkyl-($C_6$–$C_{14}$)-aryl wherein, aryl is unsubstituted or substituted, one, two or three times, independently of each other, by the abovementioned radicals 4.1) to 4.35) or 4.4) a) to 4.4) m) and R8 has the abovementioned meaning, 6. —C(O)—N(R8)-($C_0$–$C_6$)-alkyl-Het wherein, Het has the abovementioned meaning and is unsubstituted or substituted, one, two or three times, independently of each other, by the abovementioned radicals 4.1) to 4.35) or 4.4)a) to 4.4)m) and R8 has the abovementioned meaning, or 7. —NH—($C_6$–$C_{14}$)-aryl wherein, aryl is unsubstituted or substituted, one, two or three times, independently of each other, by the abovementioned radicals 4.1) to 4.35) or 4.4) a) to 4.4) m), or 8. —NH-Het wherein, Het has the abovementioned meaning and is unsubstituted or substituted, one, two or three times, independently of each other, by the abovementioned radicals 4.1) to 4.35) or 4.4) a) to 4.4) m), R3, R4, R5, R6 and R7 are identical or different and are, independently of each other,
1. hydrogen,
2. halogen,
3. —($C_1$–$C_6$)-alkyl wherein, alkyl is unsubstituted or substituted, one, two or three times, by halogen,
4. —O—($C_1$–$C_6$)-alkyl wherein, alkyl is unsubstituted or substituted, one, two or three times, by halogen, or
5. —S—($C_1$–$C_6$)-alkyl, or R4 and R5 or R5 and R6 form, together with the carbon atoms to which they are in each case bonded, independently of each other, a 5- or 6-membered ring which is aromatic or saturated and contains zero, one or two heteroatoms from the series oxygen, nitrogen or sulfur, wherein, the ring is unsubstituted or is substituted, at one or at several carbon atoms, one or two times, by halogen, and the other radicals R3, R6 and R7 or R3, R4 and R7 have the abovementioned meaning of 1, to 5;

or wherein, for the case b)

R1 is hydrogen or —($C_1$–$C_6$)-alkyl,

R2 is —($C_1$–$C_6$)-alkyl, wherein, alkyl is substituted, one, two or three times, by 1. —C(O)—O—R8', wherein, R8' is
  1.1) hydrogen or
  1.2) —($C_1$–$C_6$)-alkyl,
2. —($C_1$–$C_6$)-alkyl-O—R8', wherein, R8' has the abovementioned meaning,
3. —($C_6$–$C_{14}$)-aryl wherein, aryl is substituted, one, two or three times, independently of each other, by
  3.1) —($C_2$–$C_6$)-alkyl-C(O)—O—R8' wherein, R8' has the abovementioned meaning,
  3.2) —O—($C_1$–$C_6$)-alkyl-C(O)—O—R8' wherein, R8' has the abovementioned meaning,
  3.3) —N(R14)-(R15) wherein, R14 and R15 form, together with the nitrogen atom to which they are bonded, a 5-, 6- or 7-membered saturated ring, wherein, a heteroatom from the series oxygen, sulfur and nitrogen can also replace one or two further carbon atoms and, in the case of nitrogen, the nitrogen atoms can, independently of each other, be unsubstituted or substituted by ($C_1$–$C_6$)-alkyl,
  3.4) —(CH$_2$)$_k$—N(R9')-(R10') wherein, k is 2, 3, 4 or 5 and R9' and R10' are identical or different and are, independently of each other,
    3.4.1) hydrogen or
    3.4.2) —($C_1$–$C_6$)-alkyl, or
  R9' and R10' form, together with the nitrogen atom to which they are bonded, a 5-, 6- or 7-membered saturated ring, wherein, a heteroatom from the series oxygen, sulfur and nitrogen can also replace one or two further carbon atoms and, in the case of nitrogen, the nitrogen atoms can, independently of each other, be unsubstituted or substituted by ($C_1$–$C_6$)-alkyl,
  3.5) —O—($C_2$–$C_6$)-alkyl-N(R9')-R10', wherein, R9' and R10' have the abovementioned meaning,
  3.6) —N(R8')-C(O)—($C_1$–$C_6$)-alkyl wherein, alkyl is unsubstituted or substituted, one, two or three times, by
    3.6.1) halogen,
    3.6.2) cyano,
    3.6.3) nitro
    3.6.4) hydroxyl,
    3.6.5) amino,
    3.6.6) —C(O)—O—($C_1$–$C_6$)-alkyl, or
    3.6.7) —C(O)—OH, and R8' has the abovementioned meaning,
  3.7) -phenyl, wherein, phenyl is unsubstituted or substituted, one, two or three times, by
    3.7.1) halogen,
    3.7.2) —($C_1$–$C_6$)-alkyl,
    3.7.3) —O—($C_1$–$C_6$)-alkyl,
    3.7.4) —S(O)$_2$—R16', wherein, R16' is ($C_1$–$C_6$)-alkyl or —NH$_2$,
4. Het, wherein, Het is a saturated or unsaturated monocyclic or bicyclic, 3- to 10-membered heterocyclic ring system which contains 1, 2 or 3 identical or different ring heteroatoms from the series nitrogen, oxygen and sulfur and is unsubstituted or substituted, one, two or three times, by
  4.1) halogen,
  4.2) cyano,
  4.3) nitro,
  4.4) hydroxyl,
  4.5) amino, 4.6) —C(O)—O($C_1$–$C_6$)-alkyl,
4.7) —C(O)—OH,
4.8) —($C_1$–$C_6$)-alkyl, wherein, alkyl is unsubstituted or substituted, one, two or three times, by halogen,
4.9) —O—($C_1$–$C_6$)-alkyl, wherein, alkyl is unsubstituted or substituted, one, two or three times, by halogen,
4.10) pyridyl, or
4.11) phenyl, wherein, phenyl is unsubstituted or substituted, at least one time and independently of each other, by a radical from the series halogen, —($C_1$–$C_6$)-alkoxy and —($C_1$–$C_6$)-alkyl, and R4 and R5 or R5 and R6 form, together with the carbon atoms to which they are in each case bonded, independently of each other, a 5- or 6-membered ring which is saturated and contains one or two heteroatoms from the series oxygen, nitrogen or sulfur, where the ring is unsubstituted or substituted, at one or at several carbon atoms, one or two times, by halogen, and the other radicals R3, R6 and R7 or R3, R4 and R7 are hydrogen, or a stereoisomer or a mixture of stereoisomers in any ratio of the compound of the formula I, or a pharmaceutically acceptable salt of the compound, stereoisomer or mixture of stereoisomers of the compound;
provided that Het is not unsubstituted benzo[1,3]dioxole.

2. A compound according to claim 1,
wherein, for the case a),
R1 is hydrogen or —($C_1$–$C_6$)-alkyl,
R2 is —($C_1$–$C_6$)-alkyl, wherein, alkyl is substituted, one, two or three times, by
1. —($C_1$–$C_6$)-alkyl-O—($C_6$–$C_{14}$)-aryl,
2. —($C_0$–$C_6$)-alkyl-N(R8)-C(O)—O—($C_1$–$C_6$)-alkyl, wherein, R8 is
   i) hydrogen,
   ii) —($C_1$–$C_6$)-alkyl, wherein, alkyl is unsubstituted or substituted, one, two or three times, independently of each other, by —$NH_2$, —CN, —OH, —C(O)—OH, —C(O)—O—($C_1$–$C_6$)-alkyl, —(O)—NH—OH, $NO_2$ or halogen, or
   iii) —OH,
3. —C(O)—N(R9)-(R10), wherein, R9 and R10 are identical or different and are, independently of each other,
   i) hydrogen, or
   ii) —($C_1$–$C_6$)-alkyl, or
   R9 and R10 form, together with the nitrogen atom to which they are bonded, a 5-, 6- or 7-membered saturated ring, wherein, a heteroatom from the series oxygen, sulfur and nitrogen can also replace one or two further carbon atoms and, in the case of nitrogen, the nitrogen atoms can, independently of each other, be unsubstituted or substituted by ($C_1$–$C_6$)-alkyl,
4. phenyl, wherein, phenyl is substituted, one, two or three times, independently of each other, by
   4.1) —($C_1$–$C_6$)-alkyl-C(O)—O—R8, wherein R8 has the abovementioned meaning,
   4.2) —($C_0$–$C_6$)-alkyl-C(O)—N(R9)-(R10), wherein, R9 and R10 have the abovementioned meaning,
   4.3) —($C_0$–$C_6$)-alkyl-C(O)—NH—CN,
   4.4) —($C_0$–$C_6$)-alkyl-C(O)—($C_0$–$C_6$)-alkyl-Het, wherein, Het is a radical from the group: azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxiran, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole, and in which Het is unsubstituted or substituted, one, two or three times, independently of each other, by
   a) halogen,
   b) cyano,
   c) nitro,
   d) hydroxyl,
   e) amino,
   f) —C(O)—O—($C_1$–$C_6$)-alkyl,
   g) —C(O)—OH,
   h) —($C_1$–$C_6$)-alkyl, wherein, alkyl is unsubstituted or substituted, one, two or three times, by halogen,
   i) —O—($C_1$–$C_6$)-alkyl, wherein, alkyl is unsubstituted or substituted, one, two or three times, by halogen, or —N(R9)-(R10),
   j) =O,
   k) -Het, wherein, Het is defined as above,
   l) —($C_2$–$C_6$)-alkenyl, wherein, alkenyl is unsubstituted or substituted, one, two or three times, by halogen, or —N(R9)-(R10), or
   m) —($C_2$–$C_6$)-alkynyl, wherein, alkynyl is unsubstituted or substituted, one, two or three times, by halogen or —N(R9)-(R10),
   4.5) —($C_0$–$C_6$)-alkyl-C(O)—($C_1$–$C_6$)-alkyl-OH,
   4.6) —O—($C_0$–$C_6$)-alkyl-C(O)—N(R9)-(R10), wherein, R9 and R10 have the abovementioned meaning,
   4.7) —($C_0$–$C_6$)-alkyl-C(O)—N(R8)-($C_0$–$C_6$)-alkyl-N(R9)-(R10), wherein, R8, R9 and R10 have the abovementioned meaning,
   4.8) —($C_0$–$C_4$)-alkyl-N(R8)-S(O)$_2$—($C_0$–$C_6$)-alkyl-Het, wherein, Het is defined as above and is unsubstituted or substituted, one, two or three times, independently of each other, by the abovementioned radicals a) to m) and R8 has the abovementioned meaning,
   4.9) —($C_0$–$C_4$)-alkyl-S(O)$_2$—($C_0$–$C_6$)-alkyl-($C_6$–$C_{14}$)-phenyl, wherein, phenyl is unsubstituted or substituted, one, two or three times, independently of each other, by the abovementioned radicals a) to m),
   4.10) —($C_0$–$C_6$)-alkyl-C(O)—N(R8)-($C_0$–$C_6$)-alkyl-Het, wherein, R8 has the abovementioned meaning and Het has the abovementioned meaning and is unsubstituted or substituted, one, two or three times, independently of each other, by the abovementioned radicals a) to m),
   4.11) —($C_0$–$C_6$)-alkyl-C(O)—N(R8)-($C_0$–$C_6$)-alkyl-($C_6$–$C_{14}$)-phenyl, wherein, phenyl is unsubstituted or substituted, one, two or three times, independently of each other, by the abovementioned radicals a) to m),
   4.12) —($C_1$–$C_6$)-alkyl-N(R9)-(R10), wherein, R9 and R10 have the abovementioned meaning, 4.13) —$(CH_2)_y$—N(R8)-C(O)—$(C_1$–$C_6)$-alkyl, wherein, alkyl is unsubstituted or substituted, one, two or three times, independently of each other, by the abovementioned radicals a) to m) and y is 1 or 2, 4.14) —$(C_0$–$C_4)$-alkyl-N(R8)-C(O)—$(C_0$–$C_6)$-alkyl-$(C_6$–$C_{14})$-phenyl, wherein, phenyl is unsubstituted or substituted, one, two or three times, independently of each other, by the abovementioned radicals a) to m), 4.15) —$(C_0$–$C_4)$-alkyl-N(R8)-C(O)—$(C_0$–$C_6)$-alkyl-Het, wherein, Het is unsubstituted or substituted, one, two or three times, independently of each other, by the abovementioned radicals a) to m), 4.16) —$(C_0$–$C_4)$-alkyl-N(R8)-C(O)—O—$(C_1$–$C_6)$-alkyl, wherein, alkyl is unsubstituted or substituted, one, two or three times, independently of each other, by the abovementioned radicals a) to m), 4.17) —$(C_0$–$C_4)$-alkyl-N(R8)-C(O)—O—$(C_1$–$C_6)$-alkenyl, wherein, alkenyl is unsubstituted or substituted, one, two or three times, independently of each other, by the abovementioned radicals a) to m), 4.18) —$(C_0$–$C_4)$-alkyl-N(R8)-C(O)—O—$(C_1$–$C_6)$-alkynyl, wherein, alkynyl is unsubstituted or substituted, one, two or three times, independently of each other, by the abovementioned radicals a) to m), 4.19) —$(C_0$–$C_4)$-alkyl-N(R8)-C(O)—O—$(C_0$–$C_6)$-alkyl-$(C_6$–$C_{14})$-phenyl, wherein, phenyl is unsubstituted or substituted, one, two or three times, independently of each other, by the abovementioned radicals a) to m), 4.20) —$(C_0$–$C_4)$-alkyl-N(R8)-C(O)—O—$(C_0$–$C_6)$-alkyl-Het, wherein, Het is defined as above and is unsubstituted or substituted, one, two or three times, independently of each other, by the abovementioned radicals a) to m), 4.21) —$(C_0$–$C_4)$-alkyl-N(R8)-C(O)—$(C_0$–$C_6)$-alkyl-N(R11)-R12, wherein, R8 has the abovementioned meaning and R11 and R12 are identical or different and are, independently of each other, 4.21.1) hydrogen, 4.21.2) —$(C_1$–$C_6)$-alkyl, 4.21.3) —$(C_0$–$C_6)$-alkyl-$(C_6$–$C_{14})$-phenyl, wherein, phenyl is unsubstituted or substituted, one, two or three times, independently of each other, by the abovementioned radicals a) to m), 4.21.4) —$(C_0$–$C_6)$-alkyl-Het, wherein, Het is defined as above and is unsubstituted or substituted, one, two or three times, independently of each other, by the abovementioned radicals a) to m), 4.21.5) —C(O)—$(C_1$–$C_6)$-alkyl, wherein, alkyl is unsubstituted or substituted, one, two or three times, independently of each other, by the abovementioned radicals a) to m), 4.21.6) —C(O)—$(C_3$–$C_6)$-cycloalkyl, wherein, cycloalkyl is unsubstituted or substituted, one, two or three times, independently of each other, by the abovementioned radicals a) to m), 4.21.7) —C(O)—$(C_0$–$C_6)$-alkyl-$(C_6$–$C_{14})$-phenyl, wherein, phenyl is unsubstituted or substituted, one, two or three times, independently of each other, by the abovementioned radicals a) to m), 4.21.8) —C(O)—$(C_0$–$C_6)$-alkyl-Het, wherein, Het is defined as above and is unsubstituted or substituted, one, two or three times, independently of each other, by the abovementioned radicals a) to m), 4.21.9) —$SO_2$—$(C_0$–$C_6)$-alkyl, wherein, alkyl is unsubstituted or substituted, one, two or three times, independently of each other, by the abovementioned radicals a) to m), 4.21.10) —NH—$SO_2$—$(C_0$–$C_6)$-alkyl, wherein, alkyl is unsubstituted or substituted, one, two or three times, independently of each other, by the abovementioned radicals a) to m), 4.21.11) —$SO_2$—$(C_0$–$C_6)$-alkyl-$(C_6$–$C_{14})$-phenyl-$(C_0$–$C_6)$-alkyl, wherein, phenyl is unsubstituted or substituted, one, two or three times, independently of each other, by the abovementioned radicals a) to m), 4.21.12) —$SO_2$—$(C_0$–$C_6)$-alkyl-Het, wherein, Het is defined as above and is unsubstituted or substituted, one, two or three times, independently of each other, by the abovementioned radicals a) to m), 4.22) —O—$(C_0$–$C_6)$-alkyl-Het, wherein, Het is defined as above and is unsubstituted or substituted, one, two or three times, independently of each other, by the abovementioned radicals a) to m), or 4.23) —$(C_0$–$C_4)$-alkyl-Het, wherein, Het is defined as above and is unsubstituted or substituted, one, two or three times, independently of each other, by the abovementioned radicals a) to m), 5. —C(O)—N(R8)-$(C_0$–$C_6)$-alkyl-phenyl, wherein, phenyl is unsubstituted or substituted, one, two or three times, independently of each other, by the abovementioned radicals 4.1) to 4.23) or 4.4) a) to 4.4) m) and R8 has the abovementioned meaning, or 6. —C(O)—N(R8)-$(C_0$–$C_6)$-alkyl-Het, wherein, Het is azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole, and Het is unsubstituted or substituted, one, two or three times, independently of each other, by the abovementioned radicals 4.1) to 4.4) or 4.4) a) to 4.4) m) and R8 has the abovementioned meaning, R3, R4, R5, R6 and R7 are identical or different and are, independently of each other, 1. hydrogen,
2. halogen,
3. —$(C_1$–$C_6)$-alkyl, wherein, alkyl is unsubstituted or substituted, one, two or three times, by halogen, or
4. —O—$(C_1$–$C_6)$-alkyl, wherein, alkyl is unsubstituted or substituted, one, two or three times, by halogen, or R4 and R5 or R5 and R6 form, together with the carbon atoms to which they are in each case bonded, independently of each other, a dioxane, dioxole, dihydrofuran or furan ring, where the ring is unsubstituted or substituted, at one or at several carbon atoms, one or two times, by halogen and the other radicals R3, R6 and R7 or R3, R4 and R7 have the abovementioned meaning of 1. to 4.;

or wherein, for the case b),

R1 is hydrogen or —($C_1$–$C_4$)-alkyl,

R2 is —($C_1$–$C_4$)-alkyl, wherein, alkyl is substituted, one, two or three times, by
1. —C(O)—O—R8', wherein, R8' is
    1.1) hydrogen or
    1.2) —($C_1$–$C_4$)-alkyl,
2. —($C_1$–$C_4$)-alkyl-O—R8', wherein, R8' has the abovementioned meaning,
3. phenyl, wherein, phenyl is substituted, one, two or three times, independently of each other, by
    3.1) —($C_2$–$C_4$)-alkyl-C(O)—O—R8', wherein, R8' has the abovementioned meaning,
    3.2) —O—($C_1$–$C_4$)-alkyl-C(O)—O—R8', wherein, R8' has the abovementioned meaning,
    3.3) —N(R14)-(R15) wherein, R14 and R15 form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by ($C_1$–$C_4$)-alkyl,
    3.4) —($CH_2$)$_k$—N(R9')-R10') wherein, k is 2, 3, 4 or 5 and R9' and R10' are identical or different and are, independently of each other,
        3.4.1) hydrogen or
        3.4.2) —($C_1$–$C_6$)-alkyl, or
        R9' and R10' form, together with a nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by ($C_1$–$C_4$)-alkyl,
    3.5) —O—($C_2$–$C_6$)-alkyl-N(R9')-R10', wherein, R9' and R10' have the abovementioned meaning,
    3.6) —N(R8')-C(O)—($C_1$–$C_6$)-alkyl, wherein, alkyl is unsubstituted or substituted, one, two or three times, by
        3.6.1) halogen,
        3.6.2) cyano,
        3.6.3) nitro
        3.6.4) hydroxyl,
        3.6.5) amino,
        3.6.7) —C(O)—O—($C_1$–$C_6$)-alkyl, or
        3.6.8) —C(O)—OH, and R8' has the abovementioned meaning,
    3.7) -phenyl, wherein, phenyl is unsubstituted or substituted, one, two or three times, by
        3.7.1) halogen,
        3.7.2) —($C_1$–$C_6$)-alkyl,
        3.7.3) —O—($C_1$–$C_6$)-alkyl, or
        3.7.4) —S(O)$_2$—R16', wherein, R16' is ($C_1$–$C_6$)-alkyl or —$NH_2$,
4. Het, wherein, Het is azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole, and Het is unsubstituted or substituted, one, two or three times, independently of each other, by
    4.1) halogen,
    4.2) cyano,
    4.3) nitro,
    4.4) hydroxyl,
    4.5) amino,
    4.6) —C(O)—O($C_1$–$C_6$)-alkyl,
    4.7) —C(O)—OH,
    4.8) —($C_1$–$C_6$)-alkyl, wherein, alkyl is unsubstituted or substituted, one, two or three times, by halogen,
    4.9) —O—($C_1$–$C_6$)-alkyl, wherein, alkyl is unsubstituted or substituted, one, two or three times, by halogen,
    4.10) pyridyl, or
    4.11) phenyl, wherein, phenyl is unsubstituted or substituted, one, two or three times, independently of each other, by a radical from the series halogen, —($C_1$–$C_6$)-alkoxy and —($C_1$–$C_6$)-alkyl, and R4 and R5 or R5 and R6 form, together with the phenyl ring and the carbon atoms to which they are in each case bonded, independently of each other, a ring system from the series benzo[1,4]dioxane, 2,3-dihydrobenzofuran and 2,2-difluorobenzo[1,3]dioxole, and the other radicals R3, R6 and R7 or R3, R4 and R7 are hydrogen atom.

3. A compound according to claim 1, wherein, for the case a),

R1 is hydrogen,

R2 is —($C_1$–$C_3$)-alkyl, wherein, alkyl is substituted by
1. phenyl, wherein, phenyl is substituted, one, two or three times, independently of each other, by
    1.1) —$CH_2$—C(O)—O—R8, wherein, R8 is hydrogen, methyl, ethyl, propyl or butyl,
    1.2) —($C_0$–$C_6$)-alkyl-C(O)—N(R9)-(R10), wherein, R9 and R10 are hydrogen, methyl, ethyl, propyl or butyl, or R9 and R10 form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by ($C_1$–$C_4$)-alkyl,
    1.3) —($C_0$–$C_4$)-alkyl-C(O)—NH—CN,
    1.4) —O—($C_0$–$C_6$)-alkyl-C(O)—N(R9)-(R10), wherein, R9 and R10 have the meaning mentioned above under 1.2), 1.5) —($C_0$–$C_6$)-alkyl-C(O)—N(R8)-($C_0$–$C_6$)-alkyl-N(R9)-(R10), wherein, R8, R9 and R10 have the abovementioned meaning, 1.6) —C(O)—N(R8)-($C_0$–$C_2$)-alkyl-Het, wherein, R8 has the abovementioned meaning and Het is azepine, azetidine, aziridine, benzimidazole, benzofuran, benzo[1,4]dioxin, 1,3-benzodioxole, 4H-benzo[1,4]oxazine, benzoxazole, benzothiazole, benzothiophene, quinazoline, quinoline, quinoxaline, chroman, cinnoline, 1,2-diazepine, 1,3-diazepine, 1,4-diazepine, 1,4-dioxin, dioxole, furan, imidazole, indazole, indole, isoquinoline, isochroman, isoindole, isothiazole, isoxazole, morpholine, 1,2-oxazine, 1,3-oxazine, 1,4-oxazine, oxazole, oxirane, piperazine, piperidine, phthalazine, pyran, pyrazine, pyrazole, pyridazine, pyridine, pyrimidine, pyridoimidazole, pyridopyridine, pyridopyrimidine, pyrrole, pyrrolidine, tetrazole, 1,2-thiazine, 1,3-thiazine, 1,4-thiazine, thiazole, thiomorpholine, thiophene, thiopyran, 1,2,3-triazine, 1,3,5-triazine, 1,2,4-triazine, 1,2,3-triazole or 1,2,4-triazole, and Het is unsubstituted or substituted, one, two or three times, independently of each other, by
  a) halogen
  b) cyano,
  c) nitro,
  d) hydroxyl,
  e) amino,
  f) —C(O)—O—($C_1$–$C_4$)-alkyl,
  g) —C(O)—OH,
  h) —($C_1$–$C_4$)-alkyl, wherein, alkyl is unsubstituted or substituted, one, two or three times, by halogen,
  i) —O—($C_1$–$C_4$)-alkyl, wherein, alkyl is unsubstituted or substituted, one, two or three times, by halogen, or 1.7) —C(O)—N(R8)-($C_0$–$C_4$)-alkyl-phenyl, wherein, phenyl is unsubstituted or substituted, one, two or three times, independently of each other, by the abovementioned radicals a) to i), 1.8) —$CH_2$—N(R9)-(R10), wherein, R9 and R10 have the abovementioned meaning, 1.9) —($CH_2$)$_y$—N(R8)-C(O)—($C_1$–$C_4$)-alkyl wherein, alkyl is unsubstituted or substituted, one, two or three times, independently of each other, by the abovementioned radicals a) to i), and y is 1 or 2, 1.10) —($CH_2$)$_x$—N(R8)-C(O)—($C_0$–$C_2$)-alkyl-phenyl, wherein, phenyl is unsubstituted or substituted, one, two or three times, independently of each other, by the abovementioned radicals a) to i), and x is 0, 1 or 2, 1.11) —($CH_2$)$_x$—N(R8)-C(O)—($C_0$–$C_2$)-alkyl-Het, wherein, Het is unsubstituted or substituted, one, two or three times, independently of each other, by the abovementioned radicals a) to i), and x is 0, 1 or 2, 1.12) —($CH_2$)$_x$—N(R8)-C(O)—O—($C_1$–$C_4$)-alkyl, wherein, alkyl is unsubstituted or substituted, one, two or three times, independently of each other, by the abovementioned radicals a) to i), and x is 0, 1 or 2, 1.13) —($CH_2$)$_x$—N(R8)-C(O)—O—($C_0$–$C_4$)-alkyl-phenyl, wherein, phenyl is unsubstituted or substituted, one, two or three times, independently of each other, by the abovementioned radicals a) to i), and x is 0, 1 or 2, 1.14) —($CH_2$)$_x$—N(R8)-C(O)—O—($C_0$–$C_4$)-alkyl-Het wherein, Het is unsubstituted or substituted, one, two or three times, independently of each other, by the abovementioned radicals a) to i), and x is 0, 1 or 2, 1.15) —($CH_2$)$_x$—N(R8)-C(O)—N(R11)-R12, wherein, R8 and x have the abovementioned meaning and R11 and R12 are identical or different and are, independently of each other,
  1.15.1) hydrogen,
  1.15.2) methyl, ethyl, propyl or butyl,
  1.15.3) —($C_0$–$C_2$)-alkyl-phenyl, wherein, phenyl is unsubstituted or substituted, one, two or three times, independently of each other, by the abovementioned radicals a) to i),
  1.15.4) —($C_0$–$C_2$)-alkyl-Het, in which Het is unsubstituted or substituted, one, two or three times, independently of each other, by the abovementioned radicals a) to i),
  1.15.5) —C(O)—($C_1$–$C_4$)-alkyl,
  1.15.6) —C(O)—($C_0$–$C_2$)-alkyl-phenyl,
  1.15.7) —C(O)—($C_0$–$C_2$)-alkyl-Het,
  1.15.8) —$SO_2$—($C_1$–$C_4$)-alkyl,
  1.15.9) —$SO_2$—($C_0$–$C_4$)-alkyl-phenyl, or
  1.15.10) —$SO_2$—($C_0$–$C_2$)-alkyl-Het, R3, R4, R5, R6 and R7 are identical or different and are, independently of each other,
1. hydrogen,
2. halogen,
3. —($C_1$–$C_6$)-alkyl, wherein, alkyl is unsubstituted or substituted, one, two or three times, by halogen,
4. —O—($C_1$–$C_6$)-alkyl in which alkyl is unsubstituted or substituted, one, two or three times, by halogen, or
R4 and R5 or R5 and R6 form, together with the carbon atoms to which they are bonded, independently of each other, a dioxane, dioxole, dihydrofuran or furan ring and the other radicals R3, R6 and R7 or R3, R4 and R7 have the abovementioned meaning of 1. to 4.,
or wherein, for the case b),
R1 is hydrogen,
R2 is —($C_1$–$C_2$)-alkyl, wherein, alkyl is substituted, one, two or three times, by
1. —C(O)—O—R8', wherein, R8' is
  1.1) hydrogen or
  1.2) —($C_1$–$C_2$)-alkyl,
2. phenyl, wherein, phenyl is substituted, one, two or three times, independently of each other, by,
  2.1) —O—($C_2$–$C_4$)-alkyl-N(R9')-R10', wherein, R9' and R10' are, independently of each other, hydrogen, methyl or ethyl, or R9' and R10' form, together with the nitrogen atom to which they are bonded, a radical which can be derived from pyrrolidine, piperidine, piperazine, morpholine or thiomorpholine, and, in the case of piperazine, the second nitrogen atom can be substituted by methyl or ethyl,
  2.2) —O—($C_1$–$C_2$)-alkyl-C(O)—O—R8', wherein, R8' is, independently of each other, hydrogen, methyl or ethyl, or
  2.3) —N(R14)-(R15) wherein, R14 and R15 form, together with the nitrogen atom to which they are bonded, a radical which can be derived from pyrrolidine, piperidine, pyrazolidine, pyrazine, tetrazine, imidazolidine, piperazine, isoxazolidine, morpholine, isothiazolidine or thiomorpholine, and, in the case of nitrogen, the nitrogen atoms can, independently of each other, be unsubstituted or substituted by methyl or ethyl, 2.4) —(CH$_2$)$_k$—N(R9')-(R10') wherein, k is 2, 3 or 4 and R9' and R10' are identical or different and are, independently of each other, hydrogen, methyl or ethyl, or R9' and R10' form, together with the nitrogen atom to which they are bonded, a radical which can be derived from pyrrolidine, piperidine, piperazine, morpholine or thiomorpholine, and, in the case of piperazine, the second nitrogen atom can be substituted by methyl or ethyl, and R4 and R5 or R5 and R6 form, together with the phenyl ring and the carbon atoms to which they are in each case bonded, independently of each other, a ring system from the series benzo[1,4]dioxane, 2,3-dihydrobenzofuran and 2,2-difluorobenzo[1,3]dioxole, and the other radicals R3, R6 and R7 or R3, R4 and R7 are hydrogen.

4. The compound according to claim 1 wherein, the compound is:

pyrimidine-4,6-carboxylic acid 4-(3-methoxybenzylamide) 6-(4-propylcarbamoyl benzylamide), pyrimidine-4,6-carboxylic acid 4-(4-isopropylcarbamoylbenzylamide) 6-(3-methoxybenzylamide),

[4-({[6-(3-methoxybenzylcarbamoyl)pyrimidine-4-carbonyl]amino}methyl)phenyl]carboxyamino isopropyl ester, pyrimidine-4,6-carboxylic acid 4-(3-methoxybenzylamide) 6-[(2-phenoxyethyl)amide], (5-{[6-(3-methoxybenzylcarbamoyl)pyrimidine-4-carbonyl]amino}pentyl)carboxyamino methyl ester, pyrimidine-4,6-carboxylic acid 4-[4-(2-dimethylaminoethylcarbamoyl)benzylamide] 6-(3-methoxybenzylamide), pyrimidine-4,6-carboxylic acid 4-[(2,3-dihydrobenzo[1,4]dioxin-6-ylmethyl)amide] 6-[4-(2-dimethylaminoethylcarbamoyl)benzylamide], pyrimidine-4,6-carboxylic acid 4-(3-chloro-4-fluorobenzylamide) 6-[4-(2-dimethylaminoethylcarbamoyl)benzylamide], pyrimidine-4,6-carboxylic acid 4-dimethylcarbamoylmethylamide 6-(3-methoxybenzylamide),

[4-({[6-(3-aminobenzylcarbamoyl)pyrimidine-4-carbonyl]amino}methyl)phenyl]carboxyamino tert-butyl ester, pyrimidine-4,6-dicarboxylic acid 4-(3-chlorobenzylamide) 6-(4-fluoro-3-methylbenzylamide), pyrimidine-4,6-dicarboxylic acid 4-[(2-chloropyridin-4-ylmethyl)amide] 6-(4-fluoro-3-methylbenzylamide), pyrimidine-4,6-dicarboxylic acid 4-benzylamide 6-(4-fluoro-3-methylbenzylamide), pyrimidine-4,6-dicarboxylic acid 4-(4-fluoro-3-methylbenzylamide) 6-[(pyridin-4-ylmethyl)amide], pyrimidine-4,6-dicarboxylic acid 4-(4-fluoro-3-methylbenzylamide) 6-(pyridin-3-ylmethyl)amide], pyrimidine-4,6-carboxylic acid 4-(4-fluoro-3-methylbenzylamide) 6-{4-[2-(4-methylpiperazin-1-yl)-2-oxoethyl]benzylamide}, pyrimidine-4,6-carboxylic acid 4-(4-fluoro-3-methylbenzylamide) 6-[4(2-morpholin-4-yl-2-oxoethoxy)benzylamide], pyrimidine-4,6-carboxylic acid 4-(4-diethylcarbamoylmethoxybenzylamide) 6-(4-fluoro-3-methylbenzylamide), pyrimidine-4,6-carboxylic acid 4-(4-fluoro-3-methylbenzylamide) 6-[4-(isopropylcarbamoylmethyl)benzylamide], pyrimidine-4,6-carboxylic acid 4-(4-fluoro-3-methylbenzylamide) 6-{4-[(2-morpholin-4-ylethylcarbamoyl)methyl]benzylamide}, pyrimidine-4,6-carboxylic acid 4-(4-diethylcarbamoylmethylbenzylamide) 6-(4-fluoro-3-methylbenzylamide), pyrimidine-4,6-carboxylic acid 4-(4-fluoro-3-methylbenzylamide) 6-[4-(2-morpholin-4-yl-2-oxoethyl)benzylamide], pyrimidine-4,6-carboxylic acid 4-(4-fluoro-3-methylbenzylamide) 6-[4-(isopropylcarbamoylmethoxy)benzylamide], pyrimidine-4,6-dicarboxylic acid 4-(3-methoxybenzylamide) 6-[(pyridin-3-ylmethyl)amide], pyrimidine-4,6-carboxylic acid 4-(3-methoxybenzylamide) 6-({[(pyridin-4-ylmethyl)carbamoyl]methyl}amide), pyrimidine-4,6-carboxylic acid 4-({[(2-chloropyridin-4-ylmethyl)carbamoyl]-methyl}amide) 6-(3-methoxybenzylamide), pyrimidine-4,6-carboxylic acid 4-(3-chloro-4-fluorobenzylamide) 6-({[(2-chloropyridin-4-ylmethyl)carbamoyl]methyl}amide),

[4-({[6-(3-methoxybenzylcarbamoyl)pyrimidine-4-carbonyl]amino}methyl)phenyl]carboxyamino isobutyl ester,

[4-({[6-(3-methoxybenzylcarbamoyl)pyrimidine-4-carbonyl]amino}methyl)phenyl]carboxyamino ethyl ester,

[4-({[6-(3-methoxybenzylcarbamoyl)pyrimidine-4-carbonyl]amino}methyl)phenyl]carboxyamino allyl ester, pyrimidine-4,6-carboxylic acid 4-(3-chloro-4-fluorobenzylamide) 6-[4-(1-methylpiperidin-3-yloxy)benzylamide], pyrimidine-4,6-carboxylic acid 4-(3-chloro-4-fluorobenzylamide) 6-({[(pyridin-3-ylmethyl)carbamoyl]methyl}amide), pyrimidine-4,6-carboxylic acid 4-(3-methoxybenzylamide) 6-[4-(2-morpholin-4-ylethylcarbamoyl)benzylamide], pyrimidine-4,6-carboxylic acid 4-(3-methoxybenzylamide) 6-[4-(2-pyrrolidin-1-yl-ethylcarbamoyl)benzylamide], pyrimidine-4,6-carboxylic acid 4-[(2,3-dihydrobenzo[1,4]dioxin-6-ylmethyl)amide] 6-[(2'-sulfamoylbiphenyl-2-ylmethyl)amide];

pyrimidine-4,6-carboxylic acid 4-[(2,3-dihydrobenzofuran-5-ylmethyl)amide] 6-[(thiophen-2-ylmethyl)amide], pyrimidine-4,6-carboxylic acid 4-[(2,3-dihydrobenzofuran-5-ylmethyl)amide] 6-[(5-methylfuran-2-ylmethyl)amide], pyrimidine-4,6-carboxylic acid 4-[(2,3-dihydrobenzofuran-5-ylmethyl)amide] 6-[(5-methylfuran-2-ylmethyl)amide], pyrimidine-4,6-carboxylic acid 4-[(2,3-dihydrobenzofuran-5-ylmethyl)amide] 6-[(5-pyridin-2-ylthiophen-2-ylmethyl)amide], pyrimidine-4,6-carboxylic acid 4-[(2,3-dihydrobenzofuran-5-ylmethyl)amide] 6-[(pyridin-3-ylmethyl)amide];

pyrimidine-4,6-carboxylic acid 4-[(2,3-dihydrobenzo[1,4]dioxin-6-ylmethyl)amide] 6-[(pyridin-3-ylmethyl)amide];

pyrimidine-4,6-carboxylic acid 4-[(2,3-dihydrobenzo[1,4]dioxin-6-ylmethyl)amide] 6-[(5-methylfuran-2-ylmethyl)amide], pyrimidine-4,6-carboxylic acid 4-[(2,3-dihydrobenzo[1,4]dioxin-6-ylmethyl)amide] 6-[(thiophen-2-ylmethyl)amide];

pyrimidine-4,6-carboxylic acid 4-[(2,3-dihydrobenzofuran-5-ylmethyl)amide] 6-[(5-methylisoxazol-3-ylmethyl)amide], pyrimidine-4,6-carboxylic acid 4-[(2,3-dihydrobenzofuran-5-ylmethyl)amide] 6-[(1-methyl-1H-pyrazol-4-ylmethyl)amide], pyrimidine-4,6-carboxylic acid 4-[(2,3-dihydrobenzofuran-5-ylmethyl)amide] 6-[(2,5-dimethylfuran-3-ylmethyl)amide];

pyrimidine-4,6-carboxylic acid 4-[(6-aminopyridin-3-ylmethyl)amide] 6-[(2,3-dihydrobenzofuran-5-ylmethyl)amide];

pyrimidine-4,6-carboxylic acid 4-[(2,3-dihydrobenzofuran-5-ylmethyl)amide] 6-[(1-methyl-1H-pyrrol-2-ylmethyl)amide], pyrimidine-4,6-carboxylic acid 4-[(1H-benzoimidazol-2-ylmethyl)amide] 6-[(2,3-dihydrobenzofuran-5-ylmethyl)amide], pyrimidine-4,6-carboxylic acid 4-[(2,3-dihydrobenzofuran-5-ylmethyl)amide] 6-[(pyrazin-2-ylmethyl)amide], pyrimidine-4,6-carboxylic acid 4-[(2,2-difluorobenzo[1,3]dioxol-5-ylmethyl)amide] 6-[(pyridin-4-ylmethyl)amide], ({6-[(2,3-dihydrobenzo[1,4]dioxin-6-ylmethyl)carbamoyl]pyrimidine-4-carbonyl}amino)acetic acid methyl ester, pyrimidine-4,6-carboxylic acid 4-[(2,3-dihydrobenzofuran-5-ylmethyl)amide] 6-[(2-methyl-1H-imidazol-4-ylmethyl)amide], pyrimidine-4,6-carboxylic acid 4-[(2,3-dihydrobenzofuran-5-ylmethyl)amide] 6-[(2-pyridin-2-ylethyl)amide], pyrimidine-4,6-carboxylic acid 4-[(2,3-dihydrobenzofuran-5-ylmethyl)amide] 6-{[3-(4-fluorophenyl)-1H-pyrazol-4-ylmethyl]amide};

pyrimidine-4,6-carboxylic acid 4-[(2,3-dihydrobenzo[1,4]dioxin-6-ylmethyl)amide] 6-[4-(3-dimethylaminopropoxy)benzylamide], pyrimidine-4,6-carboxylic acid 4-[(2,3-dihydrobenzo[1,4]dioxin-6-ylmethyl)amide] 6-[4-(2-dimethylaminoethoxy)benzylamide], pyrimidine-4,6-carboxylic acid 4-[(2,3-dihydrobenzo[1,4]dioxin-6-ylmethyl)amide] 6-[3-(2-dimethylaminoethoxy)benzylamide], pyrimidine-4,6-carboxylic acid 4-[(2,3-dihydrobenzofuran-5-ylmethyl)amide] 6-[(pyridin-4-ylmethyl)amide], pyrimidine-4,6-dicarboxylic acid 4-(3-chloro-4-fluorobenzylamide) 6-(4-[3'-methylsulfonyl]ureidobenzylamide), pyrimidine-4,6-dicarboxylic acid 4-(3-methoxybenzylamide) 6-[4-(4-oxopiperidine-1-carbonyl)benzylamide], pyrimidine-4,6-dicarboxylic acid 4-(4-fluoro-3-methylbenzylamide) 6-[4-(4-oxopiperidine-1-carbonyl)benzylamide], pyrimidine-4,6-dicarboxylic acid 4-[(2,3-dihydrobenzofuran-5-ylmethyl)amide] 6-[4-(4-oxopiperidine-1-carbonyl)benzylamide], pyrimidine-4,6-dicarboxylic acid 4-[4-(4-hydroxypiperidine-1-carbonyl)benzylamide] 6-(3-methoxybenzylamide), pyrimidine-4,6-dicarboxylic acid 4-[(2,3-dihydrobenzofuran-5-ylmethyl)amide] 6-[4-(4-hydroxypiperidine-1-carbonyl)benzylamide], pyrimidine-4,6-dicarboxylic acid 4-(4-fluoro-3-methylbenzylamide) 6-[4-(4-hydroxypiperidine-1-carbonyl)benzylamide], pyrimidine-4,6-dicarboxylic acid 4-(4-fluoro-3-methylbenzylamide) 6-[4-(thiomorpholine-4-carbonyl)benzylamide], pyrimidine-4,6-dicarboxylic acid 4-(3-methoxybenzylamide) 6-[4-(thiomorpholine-4-carbonyl)benzylamide], pyrimidine-4,6-dicarboxylic acid 4-[(2,3-dihydrobenzofuran-5-ylmethyl)amide] 6-[4-(thiomorpholine-4-carbonyl)benzylamide], pyrimidine-4,6-dicarboxylic acid 4-(3-methoxybenzylamide) 6-[4-(3-oxopiperazine-1-carbonyl)benzylamide], pyrimidine-4,6-dicarboxylic acid 4-[(2,3-dihydrobenzofuran-5-ylmethyl)amide] 6-[4-(3-oxopiperazine-1-carbonyl)benzylamide], pyrimidine-4,6-dicarboxylic acid 4-(4-fluoro-3-methylbenzylamide) 6-[4-(3-oxopiperazine-1-carbonyl)benzylamide], pyrimidine-4,6-dicarboxylic acid 4-[(2,3-dihydrobenzofuran-5-ylmethyl)amide] 6-[4-(2-hydroxyethylcarbamoyl)benzylamide], pyrimidine-4,6-dicarboxylic acid 4-(4-fluoro-3-methylbenzylamide) 6-[4-(2-hydroxyethylcarbamoyl)benzylamide], pyrimidine-4,6-dicarboxylic acid 4-(4-fluoro-3-methylbenzylamide) 6-{4-[(pyridin-4-ylmethyl)carbamoyl]benzylamide}, pyrimidine-4,6-dicarboxylic acid 4-(4-cyanocarbamoylbenzylamide) 6-(4-fluoro-3-methylbenzylamide), pyrimidine-4,6-dicarboxylic acid 4-(3-methoxybenzylamide) 6-[4-(3-morpholin-4-ylpropylcarbamoyl)benzylamide], pyrimidine-4,6-dicarboxylic acid 4-[(2,3-dihydrobenzofuran-5-ylmethyl)amide] 6-[4-(3-morpholin-4-yl-propylcarbamoyl)benzylamide], pyrimidine-4,6-dicarboxylic acid 4-(4-fluoro-3-methylbenzylamide) 6-[4-(4-methylpiperazine-1-carbonyl)benzylamide], pyrimidine-4,6dicarboxylic acid 4-[(2,3-dihydrobenzofuran-5-ylmethyl)amide] 6-{4-[(pyridin-4-ylmethyl)carbamoyl]benzylamide}, pyrimidine-4,6-dicarboxylic acid 4-(4-fluoro-3-methylbenzylamide) 6-(4-[3'-methylsulfonyl]ureidobenzylamide), pyrimidine-4,6-dicarboxylic acid 4-[(2,3-dihydrobenzofuran-5-ylmethyl)amide] 6-(4-[3-methylsulfonyl]ureidobenzylamide), pyrimidine-4,6-dicarboxylic acid 4-(4-N-cyanocarbamoylbenzylamide) 6-[(2,3-dihydrobenzofuran-5-ylmethyl)amide], pyrimidine-4,6-dicarboxylic acid 4-(4-N-cyanocarbamoylbenzylamide) 6-(3-methoxybenzylamide), pyrimidine-4,6-dicarboxylic acid 4-(4-fluoro-3-methylbenzylamide) 6-[4-(morpholine-4-carbonyl)benzylamide], pyrimidine-4,6-dicarboxylic acid 4-(3-methoxybenzylamide) 6-(3-[3'-methylsulfonyl]ureidobenzylamide), pyrimidine-4,6-dicarboxylic acid 4-(4-hydroxycarbamoylbenzylamide) 6-(3-methoxybenzylamide), pyrimidine-4,6-dicarboxylic acid 4-[(2,3-dihydrobenzofuran-5-ylmethyl)amide] 6-[4-(hydroxycarbamoylmethylcarbamoyl)benzylamide], pyrimidine-4,6-dicarboxylic acid 4-[(2,3-dihydrobenzofuran-5-ylmethyl)amide] 6-[4-(1-methylpiperidin-3-yloxy)benzylamide], pyrimidine-4,6-dicarboxylic acid 4-(4-fluoro-3-methylbenzylamide) 6-[4-(2-piperazin-1-ylethylcarbamoyl)benzylamide],
pyrimidine-4,6-dicarboxylic acid 4-(4-fluoro-3-methylbenzylamide) 6-(4-hydroxycarbamoylbenzylamide),
pyrimidine-4,6-dicarboxylic acid 4-[(2,3-dihydrobenzofaran-5-ylmethyl)amide] 6-(4-hydroxycarbamoylbenzylamide),
pyrimidine-4,6-dicarboxylic acid 4-(4-fluoro-3-methylbenzylamide) 6-[4-(1-methylpiperidin-3-yloxy)benzylamide],
pyrimidine-4,6-dicarboxylic acid 4-(4-tert-butylcarbamoylbenzylamide) 6-(3-methoxybenzylamide),
pyrimidine-4,6-dicarboxylic acid 4-(3-methoxybenzylamide) 6-{4-[methyl-(1-methylpiperidin-4-yl)carbamoyl]benzylamide},
{4-[({6-[(2,3-dihydrobenzofuran-5-ylmethyl)carbamoyl]pyrimidine-4-carbonyl}amino)methyl]benzoylamino}acetic acid,
pyrimidine-4,6-dicarboxylic acid 4-(4-fluoro-3-methylbenzylamide) 6-[4-(2-pyrrolidin-1-yl-ethylcarbamoyl)benzylamide],
pyrimidine-4,6-dicarboxylic acid 4-{4-[4-(2-dimethylaminoethyl)piperazine-1-carbonyl]benzylamide} 6-(3-methoxybenzylamide),
pyrimidine-4,6-dicarboxylic acid 4-(3-methoxybenzylamide) 6-(4-[3'-methylsulfonyl]ureidobenzylamide),
pyrimidine-4,6-dicarboxylic acid 4-(3-methoxybenzylamide) 6-[3-(2-morpholin-4-ylethylcarbamoyl)benzylamide],
[4-({[6-(4-fluoro-3-methylbenzylcarbamoyl)pyrimidin-4-carbonyl]amino}methyl)benzoylamino]acetic acid,
pyrimidine-4,6-dicarboxylic acid 4-(3-methoxybenzylamide) 6-[4-(2-piperazin-1-ylacetylamino)benzylamide],
pyrimidine-4,6-dicarboxylic acid 4-(4-fluoro-3-methylbenzylamide) 6-[4-(2-morpholin-4-yl-ethylcarbamoyl)benzylamide],
[4-({[6-(4-fluoro-3-methylbenzylcarbamoyl)pyrimidin-4-carbonyl]amino}methyl)benzoylamino]acetic acid methyl ester,
pyrimidine-4,6-dicarboxylic acid 4-(3-methoxybenzylamide) 6-[3-(morpholine-4-carbonyl)benzylamide],
pyrimidine-4,6-dicarboxylic acid 4-(3-methoxybenzylamide) 6-{4-[(piperidin-4-ylmethyl)carbamoyl], benzylamide},
pyrimidine-4,6-dicarboxylic acid 4-(3-methoxybenzylamide) 6-[4-(piperidin-4-ylcarbamoyl)benzylamide],
pyrimidine-4,6-dicarboxylic acid 4-(4-fluoro-3-methylbenzylamide) 6-[4-(piperidin-4-ylcarbamoyl)benzylamide],
pyrimidine-4,6-dicarboxylic acid 4-(4-fluoro-3-methylbenzylamide) 6-{4-[methyl-(1-methylpiperidin-4-yl)carbamoyl]benzylamide},
pyrimidine-4,6-dicarboxylic acid 4-(4-fluoro-3-methylbenzylamide) 6-[(4-methyl-3,4-dihydro-2H-benzo[1,4]oxazin-7-ylmethyl)amide],
pyrimidine-4,6-dicarboxylic acid 4-(4-fluoro-3-methylbenzylamide) 6-{4-[(piperidin-4-ylmethyl)carbamoyl]benzylamide},
pyrimidine-4,6-dicarboxylic acid 4-(3-methoxybenzylamide) 6-[4-(4-methylpiperazine-1-carbonyl)benzylamide],
pyrimidine-4,6-dicarboxylic acid 4-(3-methoxybenzylamide) 6-[4-(4-pyridin-4-ylpiperazine-1-carbonyl)benzylamide],
pyrimidine-4,6-dicarboxylic acid 4-(3-methoxybenzylamide) 6-[4-(2-morpholin-4-ylacetylamino)benzylamide],
pyrimidine-4,6-dicarboxylic acid 4-[(2,3-dihydrobenzofuran-5-ylmethyl)amide] 6-[4-(morpholine-4-carbonyl)benzylamide],
pyrimidine-4,6-dicarboxylic acid 4-(3-methoxybenzylamide) 6-(4-[p-toluenesulfonyl]ureidobenzylamide),
pyrimidine-4,6-dicarboxylic acid 4-[(2,3-dihydrobenzofuran-5-ylmethyl)-amide] 6-[4-(4-methylpiperazine-1-carbonyl)benzylamide],
pyrimidine-4,6-dicarboxylic acid 4-[(2,3-dihydrobenzofuran-5-ylmethyl)amide] 6-[4-(2-pyrrolidin-1-yl-ethylcarbamoyl)benzylamide],
pyrimidine-4,6-dicarboxylic acid 4-(3-methoxybenzylamide) 6-(4-[3'-phenylsulfonyl]ureidobenzylamide),
pyrimidine-4,6-dicarboxylic acid 4-[(2,3-dihydrobenzofuran-5-ylmethyl)amide] 6-[4-(2-morpholin-4-yl-ethylcarbamoyl)benzylamide],
pyrimidine-4,6-dicarboxylic acid 4-[(2,3-dihydrobenzofuran-5-ylmethyl)amide] 6-[4-(2-pyrrolidin-1-ylethoxy)benzylamide],
pyrimidine-4,6-dicarboxylic acid 4-[4-(3-cyclohexanecarbonylureido)benzylamide]-6-(3-methoxybenzylamide),
pyrimidine-4,6-dicarboxylic acid 4-(3-methoxybenzylamide) 6-{4-[3-(pyridine-3-carbonyl)ureido]benzylamide},
pyrimidine-4,6-dicarboxylic acid 4-[4-(3-isobutyrylureido)benzylamide] 6-(3-methoxybenzylamide),
pyrimidine-4,6-dicarboxylic acid 4-(3-methoxybenzylamide) 6-[4-(2-pyrrolidin-1-ylacetylamino)benzylamide],
pyrimidine-4,6-dicarboxylic acid 4-[(4-chlorothiophen-2-ylmethyl)amide] 6-[(2,3-dihydrobenzofuran-5-ylmethyl)amide],
pyrimidine-4,6-dicarboxylic acid 4-(3-methoxybenzylamide) 6-{4-[2-(2-oxo-pyrrolidin-1-yl)acetylamino]benzylamide},
pyrimidine-4,6-dicarboxylic acid 4-[(2,3-dihydrobenzofuran-5-methyl)amide] 6-[(thiophen-3-ylmethyl)amide],
pyrimidine-4,6-dicarboxylic acid 4-[(2,3-dihydrobenzofuran-5-ylmethyl)amide] 6-[(3-methylthiophen-2-ylmethyl)amide],
pyrimidine-4,6-dicarboxylic acid 4-[(2,3-dihydrobenzofuran-5-ylmethyl)amide] 6-[(5-methylthiophen-2-ylmethyl)amide],
pyrimidine-4,6-dicarboxylic acid 4-[4-(2-dimethylaminoacetylamino)benzylamide] 6-(3-methoxybenzylamide),
pyrimidine-4,6-dicarboxylic acid 4-[(2,3-dihydrobenzofuran-5-ylmethyl)amide] 6-[4-(2-morpholin-4-ylethoxy)benzylamide],
pyrimidine-4,6-dicarboxylic acid 4-[4-(3-cyclohexylureido)benzylamide] 6-(3-methoxybenzylamide),
pyrimidine-4,6-dicarboxylic acid 4-{4-[3-(2,6-dichloropyridin-4-yl)ureido]benzylamide} 6-(3-methoxybenzylamide),
pyrimidine-4,6-dicarboxylic acid 4-[4-(3-tert-butylureido)benzylamide] 6-(3-methoxybenzylamide),
[4-({[6-(3-methoxybenzylcarbamoyl)pyrimidine-4-carbonyl]amino}methyl)phenyl]carboxyamino but-2-ynyl ester,
pyrimidine-4,6-dicarboxylic acid 4-(4-ethanesulfonylaminobenzylamide) 6-(3-methoxybenzylamide), pyrimidine-4,6-dicarboxylic acid 4-(3-methoxybenzylamide) 6-[4-(thiophene-2-sulfonylamino)benzylamide], pyrimidine-4,6-dicarboxylic acid 4-(3-methoxybenzylamide) 6-[4-(2,2,2-trifluoroethanesulfonylamino)benzylamide],

[4-({[6-(3-methoxybenzylcarbamoyl)pyrimidin-4-carbonyl]amino}methyl)phenyl]carboxyamino methyl ester,

[4-({[6-(3-methoxybenzylcarbamoyl)pyrimidine-4-carbonyl]amino}methyl)phenyl]carboxyamino prop-2-ynyl ester,

[4-({[6-(3-methoxybenzylcarbamoyl)pyrimidin-4-carbonyl]amino}methyl)phenyl]carboxyamino 2-methoxyethyl ester,

[4-({[6-(3-methoxybenzylcarbamoyl)pyrimidine-4-carbonyl]amino}methyl)phenyl]carboxyamino 4-fluorophenyl ester, pyrimidine-4,6-dicarboxylic acid 4-[4-(3-benzoylureido)benzylamide] 6-(3-methoxybenzylamide),

[3-({[6-(3-methoxybenzylcarbamoyl)pyrimidine-4-carbonyl]amino}methyl)phenyl]carboxyamino but-2-ynyl ester,

[3-({[6-(3-methoxybenzylcarbamoyl)pyrimidine-4-carbonyl]amino}methyl)phenyl]carboxyamino prop-2-ynyl ester,

[3-({[6-(3-methoxybenzylcarbamoyl)pyrimidine-4-carbonyl]amino}methyl)phenyl]carboxyamino isopropyl ester, pyrimidine-4,6-dicarboxylic acid 4-(3-chloro-4-fluorobenzylamide) 6-[4-(2-pyrrolidin-1-ylethylcarbamoyl)benzylamide], pyrimidine-4,6-dicarboxylic acid 4-(3-methoxybenzylamide) 6-[4-(morpholine-4-carbonyl)benzylamide], pyrimidine-4,6-dicarboxylic acid 4-(3-methoxybenzylamide) 6-{4-[(pyridin-4-ylmethyl)carbamoyl]benzylamide}, pyrimidine-4,6-dicarboxylic acid 4-(3-chloro-4-fluorobenzylamide) 6-(4-diethylcarbamoylbenzylamide), pyrimidine-4,6-dicarboxylic acid 4-(3-chloro-4-fluorobenzylamide) 6-[4-(morpholine-4-carbonyl)benzylamide], pyrimidine-4,6-dicarboxylic acid 4-(3-chloro-4-fluorobenzylamide) 6-[4-(2-morpholin-4-ylethylcarbamoyl)benzylamide], pyrimidine-4,6-dicarboxylic acid 4-{4-[2-(2,6-dimethylpiperidin-1-yl)-2-oxo-ethyl]benzylamide} 6-(4-fluoro-3-methylbenzylamide), pyrimidine-4,6-dicarboxylic acid 4-(3-methoxybenzylamide) 6-[4-(1-methylpiperidin-3-yloxy)benzylamide], pyrimidine-4,6-dicarboxylic acid 4-(4-diethylcarbamoylbenzylamide) 6-(3-methoxybenzylamide), pyrimidine-4,6-dicarboxylic acid 4-[(2-chloropyridin-4-ylmethyl)amide] 6-[(2,3-dihydrobenzofuran-5-ylmethyl)amide], pyrimidine-4,6-dicarboxylic acid 4-(3-chloro-4-fluorobenzylamide) 6-(4-methanesulfonylaminobenzylamide), or pyrimidine-4,6-dicarboxylic acid 4-(4-methanesulfonylbenzylamide) 6-(3-methoxybenzylamide).

5. A process for preparing a compound according to claim 1, comprising, a) reacting a compound of formula II

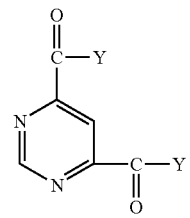

with a compound of formulas IIIa or IIIb

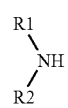

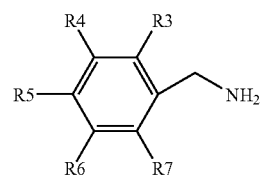

wherein, R1, R2, R3, R4, R5, R6 and R7 have the meanings given in formula I and Y is halogen, hydroxyl or $C_1$–$C_4$-alkoxy or forms, together with the carbonyl group, an active ester or a mixed anhydride, with a compound of the formula I being formed, and the reaction products are converted, where appropriate, into their physiologically tolerated salts, or b) reacting a compound of the formula II with a compound of the formulas IIIa or IIIb to give a compound of formulas IVa or IVb

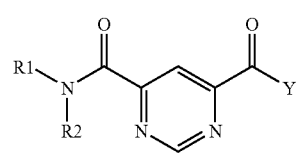

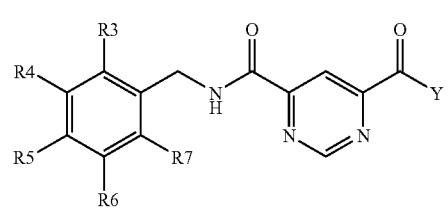

wherein, R1 to R7 have the meanings given in formula I and Y is halogen, hydroxyl or $C_1$–$C_4$-alkoxy, or forms, together with the carbonyl group, an active ester or a mixed anhydride, and the compound of the formulas IVa or IVb is purified, where appropriate, and then converted, with a compound of the formulas IIIa or IIIb, into a compound of the formula I.

6. A pharmaceutical composition comprising a pharmaceutically effective amount of the compound according to claim 1 and a pharmaceutically acceptable carrier.

7. A method for treatment of a disease associated with an increase in the activity of matrix metalloproteinase 13, wherein said disease is osteoarthrosis, in a patient in need thereof, comprising administering to such patient a pharmaceutically effective amount of a compound according to claim 1.

* * * * *